US012649062B2

(12) United States Patent
Edgerton et al.

(10) Patent No.: US 12,649,062 B2
(45) Date of Patent: *Jun. 9, 2026

(54) HIGH DENSITY EPIDURAL STIMULATION FOR FACILITATION OF LOCOMOTION, POSTURE, VOLUNTARY MOVEMENT, AND RECOVERY OF AUTONOMIC, SEXUAL, VASOMOTOR, AND COGNITIVE FUNCTION AFTER NEUROLOGICAL INJURY

(71) Applicants:California Institute of Technology, Pasadena, CA (US); University of Louisville Research Foundation, Inc., Louisville, KY (US); The Regents of the University of California, Oakland, CA (US)

(72) Inventors: Victor Reggie Edgerton, Los Angeles, CA (US); Roland R. Roy, Playa Vista, CA (US); Yury Gerasimenko, Los Angeles, CA (US); Joel W. Burdick, Pasadena, CA (US); Susan J. Harkema, Louisville, KY (US); Jonathan Hodes, Louisville, KY (US); Yu-Chong Tai, Pasadena, CA (US); Mandheerej S. Nandra, Pasadena, CA (US); Claudia A. Angeli, Louisville, KY (US); Thomas Anthony Desautels, Pasadena, CA (US)

(73) Assignees: California Institute of Technology, Pasadena, CA (US); University of Louisville Research Foundation, Inc., Louisville, KY (US); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/635,518

(22) Filed: Apr. 15, 2024

(65) Prior Publication Data
US 2024/0269468 A1      Aug. 15, 2024

Related U.S. Application Data

(63) Continuation of application No. 17/473,406, filed on Sep. 13, 2021, now Pat. No. 11,957,910, which is a
(Continued)

(51) Int. Cl.
  *A61N 1/00* (2006.01)
  *A61H 1/02* (2006.01)
  (Continued)

(52) U.S. Cl.
  CPC ....... *A61N 1/36103* (2013.01); *A61H 1/0237* (2013.01); *A61H 1/0274* (2013.01);
  (Continued)

(58) Field of Classification Search
  CPC ............. A61N 1/36103; A61N 1/0551; A61N 1/0553; A61N 1/0556; A61N 1/36003;
  (Continued)

(56) References Cited

U.S. PATENT DOCUMENTS

| | | | |
|---|---|---|---|
| 2,868,343 | A | 1/1959 | Sproul |
| 3,543,761 | A | 12/1970 | Bradley |

(Continued)

FOREIGN PATENT DOCUMENTS

| | | | |
|---|---|---|---|
| AU | 2012204526 B2 | 5/2016 | |
| CA | 2649663 A1 | 11/2007 | |

(Continued)

OTHER PUBLICATIONS

International Search Report and Written Opinion issued in counterpart PCT Application No. PCT/US2016/045898 mailed Dec. 5, 2016, 13 pages.

(Continued)

*Primary Examiner* — Scott M. Getzow
(74) *Attorney, Agent, or Firm* — K&L Gates LLP

(57) ABSTRACT

A system and methods are disclosed for enabling or improving control of cardiovascular and/or vasomotor autonomic functions in a patient having a neurologically derived paralysis or a nervous system disorder.

22 Claims, 25 Drawing Sheets

Related U.S. Application Data continuation of application No. 15/878,325, filed on Jan. 23, 2018, now Pat. No. 11,116,976, which is a continuation of application No. 14/790,729, filed on Jul. 2, 2015, now Pat. No. 9,907,958, which is a continuation of application No. 13/978,035, filed as application No. PCT/US2012/020112 on Jan. 3, 2012, now Pat. No. 9,101,769.

(60) Provisional application No. 61/469,555, filed on Mar. 30, 2011, provisional application No. 61/429,368, filed on Jan. 3, 2011, provisional application No. 61/437,418, filed on Jan. 28, 2011.

(51) Int. Cl.
| | |
|---|---|
| *A61N 1/05* | (2006.01) |
| *A61N 1/36* | (2006.01) |
| *A63B 21/00* | (2006.01) |
| *A63B 22/02* | (2006.01) |
| *A63B 69/00* | (2006.01) |

(52) U.S. Cl.
CPC ......... *A61N 1/0551* (2013.01); *A61N 1/0553* (2013.01); *A61N 1/0556* (2013.01); *A61N 1/36003* (2013.01); *A63B 21/00181* (2013.01); *A61N 1/3616* (2013.01); *A63B 22/0235* (2013.01); *A63B 69/0064* (2013.01); *A63B 2213/004* (2013.01); *A63B 2220/805* (2013.01); *A63B 2230/60* (2013.01); *F04C 2270/0421* (2013.01)

(58) Field of Classification Search
CPC .. A61N 1/3616; A61H 1/0237; A61H 1/0274; A63B 21/00181; A63B 22/0235; A63B 69/0064; A63B 2213/004; A63B 2220/805; A63B 2230/60; F04C 2270/0421; A61B 5/40–4094
See application file for complete search history.

(56) References Cited

U.S. PATENT DOCUMENTS

| | | | |
|---|---|---|---|
| 3,650,277 | A | 3/1972 | Sjostrand et al. |
| 3,653,518 | A | 4/1972 | Polen |
| 3,662,758 | A | 5/1972 | Glover |
| 3,724,467 | A | 4/1973 | Avery et al. |
| 4,044,774 | A | 8/1977 | Corbin et al. |
| 4,102,344 | A | 7/1978 | Conway et al. |
| 4,141,365 | A | 2/1979 | Fischell et al. |
| 4,285,347 | A | 8/1981 | Hess |
| 4,303,904 | A | 12/1981 | Chasek |
| 4,340,063 | A | 7/1982 | Maurer |
| 4,340,216 | A | 7/1982 | Murphy |
| 4,356,902 | A | 11/1982 | Murphy |
| 4,379,462 | A | 4/1983 | Borkan et al. |
| 4,398,537 | A | 8/1983 | Holmbo |
| 4,402,501 | A | 9/1983 | Lohman |
| 4,410,175 | A | 10/1983 | Shamp |
| 4,414,986 | A | 11/1983 | Dickhudt et al. |
| 4,538,624 | A | 9/1985 | Tarjan |
| 4,549,556 | A | 10/1985 | Tarjan et al. |
| 4,559,948 | A | 12/1985 | Liss et al. |
| 4,569,352 | A | 2/1986 | Petrofsky et al. |
| 4,573,481 | A | 3/1986 | Bullara |
| 4,574,789 | A | 3/1986 | Forster |
| 4,724,842 | A | 2/1988 | Charters |
| 4,742,054 | A | 5/1988 | Naftchi |
| 4,784,420 | A | 11/1988 | Makino et al. |
| 4,798,982 | A | 1/1989 | Voorman |
| 4,800,898 | A | 1/1989 | Hess et al. |
| 4,934,368 | A | 6/1990 | Lynch |
| 4,969,452 | A | 11/1990 | Petrofsky et al. |
| 5,002,053 | A | 3/1991 | Garcia-Rill et al. |
| 5,018,631 | A | 5/1991 | Reimer |
| 5,031,618 | A | 7/1991 | Mullett |
| 5,066,272 | A | 11/1991 | Eaton et al. |
| 5,081,989 | A | 1/1992 | Graupe et al. |
| 5,121,754 | A | 6/1992 | Mullett |
| 5,284,151 | A | 2/1994 | Onoda |
| 5,337,908 | A | 8/1994 | Beck, Jr. |
| 5,344,439 | A | 9/1994 | Otten |
| 5,348,544 | A | 9/1994 | Sweeney et al. |
| 5,354,320 | A | 10/1994 | Schaldach et al. |
| 5,366,813 | A | 11/1994 | Berlin |
| 5,374,285 | A | 12/1994 | Vaiani et al. |
| 5,417,719 | A | 5/1995 | Hull et al. |
| 5,421,783 | A | 6/1995 | Kockelman et al. |
| 5,441,465 | A | 8/1995 | Hefner et al. |
| 5,443,486 | A | 8/1995 | Hrdlicka et al. |
| 5,476,441 | A | 12/1995 | Durfee et al. |
| 5,553,270 | A | 9/1996 | Rosenbluth |
| 5,562,718 | A | 10/1996 | Palermo |
| 5,571,141 | A | 11/1996 | McNeil et al. |
| 5,584,818 | A | 12/1996 | Morrison |
| 5,601,527 | A | 2/1997 | Selkowitz |
| 5,626,540 | A | 5/1997 | Hall |
| 5,630,836 | A | 5/1997 | Prem et al. |
| 5,643,330 | A | 7/1997 | Holsheimer et al. |
| 5,643,332 | A | 7/1997 | Stein |
| 5,667,461 | A | 9/1997 | Hall |
| 5,733,322 | A | 3/1998 | Starkebaum |
| 5,788,606 | A | 8/1998 | Rich |
| 5,814,018 | A | 9/1998 | Elson et al. |
| 5,819,962 | A | 10/1998 | Okubo et al. |
| 5,876,425 | A | 3/1999 | Gord et al. |
| 5,877,183 | A | 3/1999 | Cincotta |
| 5,948,004 | A | 9/1999 | Weijand et al. |
| 5,958,933 | A | 9/1999 | Naftchi |
| 5,983,141 | A | 11/1999 | Sluijter et al. |
| 5,984,368 | A | 11/1999 | Cain |
| 6,052,624 | A | 4/2000 | Mann |
| 6,058,331 | A | 5/2000 | King |
| 6,066,163 | A | 5/2000 | John |
| 6,080,087 | A | 6/2000 | Bingham |
| 6,104,957 | A | 8/2000 | Alo et al. |
| 6,115,634 | A | 9/2000 | Donders et al. |
| 6,122,548 | A | 9/2000 | Starkebaum et al. |
| 6,139,475 | A | 10/2000 | Bessler et al. |
| 6,168,948 | B1 | 1/2001 | Anderson et al. |
| 6,182,843 | B1 | 2/2001 | Tax et al. |
| 6,188,927 | B1 | 2/2001 | Lu et al. |
| 6,236,892 | B1 | 5/2001 | Feler |
| 6,280,640 | B1 | 8/2001 | Hurwitz et al. |
| 6,281,207 | B1 | 8/2001 | Richter et al. |
| 6,308,103 | B1 | 10/2001 | Gielen |
| 6,309,401 | B1 | 10/2001 | Redko et al. |
| 6,319,241 | B1 | 11/2001 | King et al. |
| D454,139 | S | 3/2002 | Feldcamp |
| 6,463,327 | B1 | 10/2002 | Lurie et al. |
| 6,464,208 | B1 | 10/2002 | Smith |
| 6,470,213 | B1 | 10/2002 | Alley |
| 6,490,486 | B1 | 12/2002 | Bradley |
| 6,500,110 | B1 | 12/2002 | Davey et al. |
| 6,503,231 | B1 | 1/2003 | Prausnitz et al. |
| 6,505,074 | B2 | 1/2003 | Boveja et al. |
| 6,516,227 | B1 | 2/2003 | Meadows et al. |
| 6,551,849 | B1 | 4/2003 | Kenney |
| 6,587,724 | B2 | 7/2003 | Mann |
| 6,662,053 | B2 | 12/2003 | Borkan |
| 6,666,831 | B1 | 12/2003 | Edgerton et al. |
| 6,685,729 | B2 | 2/2004 | Gonzalez |
| 6,748,276 | B1 | 6/2004 | Daignault, Jr. et al. |
| 6,819,956 | B2 | 11/2004 | DiLorenzo |
| 6,839,594 | B2 | 1/2005 | Cohen et al. |
| 6,862,479 | B1 | 3/2005 | Whitehurst et al. |
| 6,871,099 | B1 | 3/2005 | Whitehurst et al. |
| 6,878,112 | B2 | 4/2005 | Linberg et al. |
| 6,892,098 | B2 | 5/2005 | Ayal et al. |
| 6,895,280 | B2 | 5/2005 | Meadows et al. |
| 6,895,283 | B2 | 5/2005 | Erickson et al. |
| 6,901,292 | B2 | 5/2005 | Hrdlicka et al. |

(56)     References Cited

U.S. PATENT DOCUMENTS

| | | | |
|---|---|---|---|
| 6,937,891 B2 | 8/2005 | Leinders et al. |
| 6,950,706 B2 | 9/2005 | Rodriguez et al. |
| 6,975,907 B2 | 12/2005 | Zanakis et al. |
| 6,978,181 B1 | 12/2005 | Snell |
| 6,988,006 B2 | 1/2006 | King et al. |
| 6,999,820 B2 | 2/2006 | Jordan |
| 7,010,749 B2 | 3/2006 | Hasha et al. |
| 7,020,521 B1 | 3/2006 | Brewer et al. |
| 7,024,247 B2 | 4/2006 | Gliner et al. |
| 7,035,690 B2 | 4/2006 | Goetz |
| 7,047,084 B2 | 5/2006 | Erickson et al. |
| 7,065,408 B2 | 6/2006 | Herman et al. |
| 7,096,070 B1 | 8/2006 | Jenkins et al. |
| 7,099,718 B1 | 8/2006 | Thacker et al. |
| 7,110,820 B2 | 9/2006 | Tcheng et al. |
| 7,125,388 B1 | 10/2006 | Reinkensmeyer et al. |
| 7,127,287 B2 | 10/2006 | Duncan et al. |
| 7,127,296 B2 | 10/2006 | Bradley |
| 7,127,297 B2 | 10/2006 | Law et al. |
| 7,135,497 B1 | 11/2006 | Zeman et al. |
| 7,146,221 B2 | 12/2006 | Krulevitch et al. |
| 7,149,773 B2 | 12/2006 | Haller et al. |
| 7,153,242 B2 | 12/2006 | Goffer |
| 7,184,837 B2 | 2/2007 | Goetz |
| 7,200,443 B2 | 4/2007 | Faul |
| 7,209,787 B2 | 4/2007 | DiLorenzo |
| 7,228,179 B2 | 6/2007 | Campen et al. |
| 7,239,920 B1 | 7/2007 | Thacker et al. |
| 7,251,529 B2 | 7/2007 | Greenwood-Van Meerveld |
| 7,252,090 B2 | 8/2007 | Goetz |
| 7,313,440 B2 | 12/2007 | Miesel |
| 7,324,853 B2 | 1/2008 | Ayal et al. |
| 7,330,760 B2 | 2/2008 | Heruth et al. |
| 7,330,762 B2 | 2/2008 | Boveja et al. |
| 7,337,005 B2 | 2/2008 | Kim et al. |
| 7,337,006 B2 | 2/2008 | Kim et al. |
| 7,340,298 B1 | 3/2008 | Barbut |
| 7,377,006 B2 | 5/2008 | Genoa et al. |
| 7,381,192 B2 | 6/2008 | Brodard et al. |
| 7,415,309 B2 | 8/2008 | McIntyre |
| 7,450,992 B1 | 11/2008 | Cameron |
| 7,463,927 B1 | 12/2008 | Chaouat |
| 7,463,928 B2 | 12/2008 | Lee et al. |
| 7,467,016 B2 | 12/2008 | Colborn |
| 7,493,170 B1 | 2/2009 | Segel et al. |
| 7,496,404 B2 | 2/2009 | Meadows et al. |
| 7,502,652 B2 | 3/2009 | Gaunt et al. |
| 7,536,226 B2 | 5/2009 | Williams et al. |
| D594,024 S | 6/2009 | King |
| D595,308 S | 6/2009 | King |
| 7,544,185 B2 | 6/2009 | Bengtsson |
| 7,565,195 B1 | 7/2009 | Kroll et al. |
| 7,584,000 B2 | 9/2009 | Erickson |
| 7,590,454 B2 | 9/2009 | Garabedian et al. |
| 7,603,178 B2 | 10/2009 | North et al. |
| 7,620,502 B2 | 11/2009 | Selifonov et al. |
| 7,628,750 B2 | 12/2009 | Cohen et al. |
| 7,647,115 B2 | 1/2010 | Levin et al. |
| 7,660,636 B2 | 2/2010 | Castel et al. |
| 7,697,995 B2 | 4/2010 | Cross, Jr. et al. |
| 7,725,193 B1 | 5/2010 | Chu |
| 7,729,781 B2 | 6/2010 | Swoyer et al. |
| 7,734,340 B2 | 6/2010 | De Ridder |
| 7,734,351 B2 | 6/2010 | Testerman et al. |
| 7,742,037 B2 | 6/2010 | Sako et al. |
| 7,769,463 B2 | 8/2010 | Katsnelson |
| 7,769,464 B2 | 8/2010 | Gerber et al. |
| 7,780,617 B2 | 8/2010 | Tornatore et al. |
| 7,797,057 B2 | 9/2010 | Harris |
| 7,801,600 B1 | 9/2010 | Carbunaru et al. |
| 7,801,601 B2 | 9/2010 | Maschino et al. |
| 7,813,803 B2 | 10/2010 | Heruth et al. |
| 7,813,809 B2 | 10/2010 | Strother et al. |
| 7,840,270 B2 | 11/2010 | Ignagni et al. |
| 7,856,264 B2 | 12/2010 | Firlik et al. |
| 7,861,872 B2 | 1/2011 | Ng et al. |
| 7,877,146 B2 | 1/2011 | Rezai et al. |
| 7,890,182 B2 | 2/2011 | Parramon et al. |
| D638,439 S | 5/2011 | Cavanaugh et al. |
| 7,949,395 B2 | 5/2011 | Kuzma |
| 7,949,403 B2 | 5/2011 | Palermo et al. |
| 7,987,000 B2 | 7/2011 | Moffitt et al. |
| 7,991,465 B2 | 8/2011 | Bartic et al. |
| 8,019,427 B2 | 9/2011 | Moffitt |
| 8,050,773 B2 | 11/2011 | Zhu |
| 8,063,087 B2 | 11/2011 | Chow et al. |
| 8,100,815 B2 | 1/2012 | Balaker et al. |
| 8,108,051 B2 | 1/2012 | Cross, Jr. et al. |
| 8,108,052 B2 | 1/2012 | Boling |
| D656,153 S | 3/2012 | Imamura et al. |
| 8,131,358 B2 | 3/2012 | Moffitt et al. |
| 8,135,473 B2 | 3/2012 | Miesel et al. |
| 8,155,750 B2 | 4/2012 | Jaax et al. |
| 8,168,481 B2 | 5/2012 | Hanaoka et al. |
| 8,170,660 B2 | 5/2012 | Dacey, Jr. et al. |
| 8,190,262 B2 | 5/2012 | Gerber et al. |
| 8,195,304 B2 | 6/2012 | Strother et al. |
| 8,214,048 B1 | 7/2012 | Whitehurst et al. |
| 8,224,453 B2 | 7/2012 | De Ridder |
| 8,229,565 B2 | 7/2012 | Kim et al. |
| 8,238,666 B2 | 8/2012 | Besley et al. |
| 8,239,038 B2 | 8/2012 | Wolf, II |
| 8,260,436 B2 | 9/2012 | Gerber et al. |
| 8,265,770 B2 | 9/2012 | Toy et al. |
| 8,271,099 B1 | 9/2012 | Swanson |
| 8,295,936 B2 | 10/2012 | Wahlstrand et al. |
| 8,311,644 B2 | 11/2012 | Moffitt et al. |
| 8,326,569 B2 | 12/2012 | Lee et al. |
| 8,332,029 B2 | 12/2012 | Glukhovsky et al. |
| 8,332,047 B2 | 12/2012 | Libbus et al. |
| 8,332,053 B1 | 12/2012 | Patterson et al. |
| 8,346,366 B2 | 1/2013 | Arle et al. |
| 8,352,036 B2 | 1/2013 | Dimarco et al. |
| 8,355,791 B2 | 1/2013 | Moffitt |
| 8,355,797 B2 | 1/2013 | Caparso et al. |
| 8,364,273 B2 | 1/2013 | De Ridder |
| 8,369,961 B2 | 2/2013 | Christman et al. |
| 8,374,696 B2 | 2/2013 | Sanchez et al. |
| D677,674 S | 3/2013 | Rampson et al. |
| 8,407,576 B1 | 3/2013 | Yin et al. |
| 8,412,345 B2 | 4/2013 | Moffitt |
| 8,428,728 B2 | 4/2013 | Sachs |
| 8,442,655 B2 | 5/2013 | Moffitt et al. |
| 8,452,406 B2 | 5/2013 | Arcot-Krishnamurthy et al. |
| D684,991 S | 6/2013 | Wenz et al. |
| D684,996 S | 6/2013 | Wenz et al. |
| 8,463,400 B2 | 6/2013 | Hegi et al. |
| D688,259 S | 8/2013 | Pearcy et al. |
| D689,086 S | 9/2013 | Philopoulos |
| 8,543,200 B2 | 9/2013 | Lane et al. |
| D691,154 S | 10/2013 | Talbot et al. |
| D691,172 S | 10/2013 | Wujcik et al. |
| 8,588,884 B2 | 11/2013 | Hegde et al. |
| D694,763 S | 12/2013 | Edwards et al. |
| 8,626,300 B2 | 1/2014 | Demarais et al. |
| 8,630,717 B2 | 1/2014 | Olson et al. |
| 8,700,145 B2 | 4/2014 | Kilgard et al. |
| 8,712,546 B2 | 4/2014 | Kim et al. |
| D705,241 S | 5/2014 | Chen et al. |
| D707,235 S | 6/2014 | Arnold et al. |
| 8,740,825 B2 | 6/2014 | Ehrenreich et al. |
| 8,750,957 B2 | 6/2014 | Tang et al. |
| RE45,030 E | 7/2014 | Stevenson et al. |
| 8,766,928 B2 | 7/2014 | Weeldreyer et al. |
| 8,768,472 B2 | 7/2014 | Fang et al. |
| 8,768,481 B2 | 7/2014 | Lane |
| 8,788,046 B2 | 7/2014 | Bennett et al. |
| 8,805,542 B2 | 8/2014 | Tai et al. |
| 8,836,368 B2 | 9/2014 | Afshar et al. |
| 8,847,548 B2 | 9/2014 | Kesler et al. |
| 8,849,410 B2 | 9/2014 | Walker et al. |
| 8,849,418 B2 | 9/2014 | Daglow |
| 8,897,870 B2 | 11/2014 | De Ridder |
| 8,903,502 B2 | 12/2014 | Perryman et al. |

(56) References Cited

U.S. PATENT DOCUMENTS

| | | | |
|---|---|---|---|
| D721,722 S | 1/2015 | Lee |
| 8,957,549 B2 | 2/2015 | Kesler et al. |
| D735,231 S | 7/2015 | Omiya |
| 9,072,891 B1 | 7/2015 | Rao |
| 9,079,039 B2 | 7/2015 | Carlson et al. |
| 9,101,769 B2 | 8/2015 | Edgerton et al. |
| D737,840 S | 9/2015 | Omiya |
| 9,192,768 B2 | 11/2015 | Yokoi et al. |
| 9,205,259 B2 | 12/2015 | Kim et al. |
| 9,205,260 B2 | 12/2015 | Kim et al. |
| 9,205,261 B2 | 12/2015 | Kim et al. |
| 9,248,291 B2 | 2/2016 | Mashiach |
| D750,664 S | 3/2016 | Chen et al. |
| 9,272,139 B2 | 3/2016 | Hamilton et al. |
| 9,272,143 B2 | 3/2016 | Libbus et al. |
| 9,283,391 B2 | 3/2016 | Ahmed |
| 9,314,630 B2 | 4/2016 | Levin et al. |
| D758,398 S | 6/2016 | Yu et al. |
| 9,358,384 B2 | 6/2016 | Dubuclet |
| D760,753 S | 7/2016 | Cheng et al. |
| D762,234 S | 7/2016 | Li et al. |
| 9,393,409 B2 | 7/2016 | Edgerton et al. |
| D763,273 S | 8/2016 | Hwang et al. |
| 9,409,023 B2 | 8/2016 | Burdick et al. |
| 9,409,030 B2 | 8/2016 | Perryman et al. |
| 9,415,218 B2 | 8/2016 | Edgerton et al. |
| 9,421,365 B2 | 8/2016 | Sumners et al. |
| D769,302 S | 10/2016 | Rodriguez |
| D770,468 S | 11/2016 | Carlson et al. |
| D770,470 S | 11/2016 | Jin |
| 9,520,887 B1 | 12/2016 | Zhuang et al. |
| D780,768 S | 3/2017 | Carlson et al. |
| 9,592,358 B2 | 3/2017 | Miller et al. |
| 9,592,385 B2 | 3/2017 | Kaula et al. |
| 9,597,517 B2 | 3/2017 | Moffitt |
| D783,032 S | 4/2017 | Cashner et al. |
| 9,610,442 B2 | 4/2017 | Yoo et al. |
| D788,134 S | 5/2017 | Wong et al. |
| 9,639,982 B2 | 5/2017 | Craik et al. |
| 9,656,076 B2 | 5/2017 | Trier et al. |
| D789,963 S | 6/2017 | Agashiwala et al. |
| D794,667 S | 8/2017 | Havaldar et al. |
| 9,717,908 B2 | 8/2017 | Karunasiri |
| 9,724,513 B2 | 8/2017 | Lane et al. |
| 9,802,052 B2 | 10/2017 | Marnfeldt |
| 9,812,875 B2 | 11/2017 | Nejatali et al. |
| D806,717 S | 1/2018 | Bae et al. |
| 9,895,545 B2 | 2/2018 | Rao et al. |
| D816,708 S | 5/2018 | Riedel et al. |
| D819,681 S | 6/2018 | Fung et al. |
| 9,993,642 B2 | 6/2018 | Gerasimenko et al. |
| 10,092,750 B2 | 10/2018 | Edgerton et al. |
| D834,601 S | 11/2018 | Felt |
| 10,124,166 B2 | 11/2018 | Edgerton et al. |
| 10,137,299 B2 | 11/2018 | Lu et al. |
| D839,278 S | 1/2019 | Carlson et al. |
| D839,914 S | 2/2019 | Lee et al. |
| D841,017 S | 2/2019 | Bathla |
| D843,388 S | 3/2019 | Protzman et al. |
| 10,406,366 B2 | 9/2019 | Westlund et al. |
| 10,449,371 B2 | 10/2019 | Serrano Carmona |
| D874,491 S | 2/2020 | Kuo et al. |
| D874,507 S | 2/2020 | Martell et al. |
| D875,108 S | 2/2020 | Chitalia et al. |
| D875,752 S | 2/2020 | Nelson et al. |
| D877,753 S | 3/2020 | Chitalia et al. |
| 10,751,533 B2 | 8/2020 | Edgerton et al. |
| 10,758,732 B1 | 9/2020 | Heldman |
| 10,773,074 B2 | 9/2020 | Liu et al. |
| 10,799,701 B2 | 10/2020 | Lee |
| 10,806,927 B2 | 10/2020 | Edgerton et al. |
| 10,806,935 B2 | 10/2020 | Rao et al. |
| D904,437 S | 12/2020 | Chitalia et al. |
| D905,701 S | 12/2020 | Feng et al. |
| 10,881,853 B2 | 1/2021 | Edgerton et al. |
| 10,898,719 B2 | 1/2021 | Pivonka et al. |
| D912,074 S | 3/2021 | Giannino et al. |
| D926,784 S | 8/2021 | Carlson et al. |
| D928,188 S | 8/2021 | Giannino et al. |
| 11,097,122 B2 | 8/2021 | Lu |
| 11,123,312 B2 | 9/2021 | Lu et al. |
| 11,129,983 B2 | 9/2021 | Lo et al. |
| D939,549 S | 12/2021 | Miyai et al. |
| D947,216 S | 3/2022 | Leininger |
| 11,266,850 B2 | 3/2022 | Prouza et al. |
| 11,298,533 B2 | 4/2022 | Edgerton et al. |
| D962,245 S | 8/2022 | Thompson et al. |
| 11,400,284 B2 | 8/2022 | Gerasimenko et al. |
| 11,491,336 B2 | 11/2022 | Scheltienne et al. |
| 11,511,116 B2 | 11/2022 | Wagner et al. |
| 11,515,733 B2 | 11/2022 | Babakhani et al. |
| 11,638,820 B2 | 5/2023 | Edgerton et al. |
| 11,684,774 B2 | 6/2023 | Crosby et al. |
| 11,691,015 B2 | 7/2023 | Minassian et al. |
| D1,008,290 S | 12/2023 | Stapfer |
| D1,008,291 S | 12/2023 | Stapfer |
| D1,010,666 S | 1/2024 | Cai et al. |
| 11,911,621 B2 | 2/2024 | Ganty et al. |
| 11,944,814 B2 | 4/2024 | Lo et al. |
| 11,957,910 B2 | 4/2024 | Edgerton et al. |
| 11,986,653 B2 | 5/2024 | Lo et al. |
| 11,992,684 B2 | 5/2024 | Minassian et al. |
| 12,018,135 B2 | 6/2024 | Scher et al. |
| 12,023,492 B2 | 7/2024 | Edgerton et al. |
| 12,076,301 B2 | 9/2024 | Lu et al. |
| D1,044,827 S | 10/2024 | Tabrizi et al. |
| 12,201,833 B2 | 1/2025 | Edgerton et al. |
| 12,214,198 B2 | 2/2025 | Bennett et al. |
| 12,268,878 B2 | 4/2025 | Phillips et al. |
| 12,415,079 B2 | 9/2025 | Scheltienne et al. |
| 2001/0016266 A1 | 8/2001 | Okazaki et al. |
| 2001/0032992 A1 | 10/2001 | Wendt |
| 2002/0042814 A1 | 4/2002 | Fukasawa et al. |
| 2002/0050456 A1 | 5/2002 | Sheppard, Jr. et al. |
| 2002/0052539 A1 | 5/2002 | Haller et al. |
| 2002/0055779 A1 | 5/2002 | Andrews |
| 2002/0083240 A1 | 6/2002 | Hoese et al. |
| 2002/0111661 A1 | 8/2002 | Cross et al. |
| 2002/0115945 A1 | 8/2002 | Herman et al. |
| 2002/0123672 A1 | 9/2002 | Christophersom et al. |
| 2002/0138512 A1 | 9/2002 | Buresh et al. |
| 2002/0173505 A1 | 11/2002 | Skogvall |
| 2002/0175931 A1 | 11/2002 | Holtz et al. |
| 2002/0187260 A1 | 12/2002 | Sheppard, Jr. et al. |
| 2002/0188332 A1 | 12/2002 | Lurie et al. |
| 2002/0193843 A1 | 12/2002 | Hill et al. |
| 2003/0032992 A1 | 2/2003 | Thacker et al. |
| 2003/0078633 A1 | 4/2003 | Firlik et al. |
| 2003/0093021 A1 | 5/2003 | Goffer |
| 2003/0093131 A1 | 5/2003 | Loeb et al. |
| 2003/0097166 A1 | 5/2003 | Krulevitch et al. |
| 2003/0100933 A1 | 5/2003 | Ayal et al. |
| 2003/0113725 A1 | 6/2003 | Small et al. |
| 2003/0114894 A1 | 6/2003 | Dar et al. |
| 2003/0114899 A1 | 6/2003 | Woods et al. |
| 2003/0135253 A1 | 7/2003 | Kokones et al. |
| 2003/0139422 A1 | 7/2003 | Teng |
| 2003/0145759 A1 | 8/2003 | Rodnunsky |
| 2003/0158583 A1 | 8/2003 | Burnett et al. |
| 2003/0199116 A1 | 10/2003 | Tai et al. |
| 2003/0200323 A1 | 10/2003 | Dold et al. |
| 2003/0208248 A1 | 11/2003 | Carter et al. |
| 2003/0220679 A1 | 11/2003 | Han |
| 2003/0233137 A1 | 12/2003 | Paul, Jr. |
| 2004/0039425 A1 | 2/2004 | Greenwood-Van Meerveld |
| 2004/0044380 A1 | 3/2004 | Bruninga et al. |
| 2004/0082979 A1 | 4/2004 | Tong et al. |
| 2004/0087286 A1 | 5/2004 | Inoue et al. |
| 2004/0088015 A1 | 5/2004 | Casavant et al. |
| 2004/0111118 A1 | 6/2004 | Hill et al. |
| 2004/0111126 A1 | 6/2004 | Tanagho et al. |
| 2004/0121528 A1 | 6/2004 | Krulevitch et al. |
| 2004/0122483 A1 | 6/2004 | Nathan et al. |
| 2004/0127954 A1 | 7/2004 | McDonald |

(56) References Cited

U.S. PATENT DOCUMENTS

| | | |
|---|---|---|
| 2004/0133248 A1 | 7/2004 | Frei et al. |
| 2004/0138518 A1 | 7/2004 | Rise et al. |
| 2004/0147975 A1 | 7/2004 | Popovic et al. |
| 2004/0172027 A1 | 9/2004 | Speitling et al. |
| 2004/0172097 A1 | 9/2004 | Brodard et al. |
| 2004/0181263 A1 | 9/2004 | Balzer et al. |
| 2004/0192082 A1 | 9/2004 | Wagner et al. |
| 2004/0192834 A1 | 9/2004 | Nakayoshi et al. |
| 2004/0243204 A1 | 12/2004 | Maghribi et al. |
| 2004/0267320 A1 | 12/2004 | Taylor et al. |
| 2005/0004622 A1 | 1/2005 | Cullen et al. |
| 2005/0043775 A1 | 2/2005 | John et al. |
| 2005/0061315 A1 | 3/2005 | Lee et al. |
| 2005/0070982 A1 | 3/2005 | Heruth et al. |
| 2005/0075662 A1 | 4/2005 | Pedersen et al. |
| 2005/0075669 A1 | 4/2005 | King |
| 2005/0075678 A1 | 4/2005 | Faul |
| 2005/0075693 A1 | 4/2005 | Toy et al. |
| 2005/0080460 A1 | 4/2005 | Wang et al. |
| 2005/0090756 A1 | 4/2005 | Wolf et al. |
| 2005/0101827 A1 | 5/2005 | Delisle |
| 2005/0102007 A1 | 5/2005 | Ayal et al. |
| 2005/0113878 A1 | 5/2005 | Gerber |
| 2005/0113882 A1 | 5/2005 | Cameron et al. |
| 2005/0119713 A1 | 6/2005 | Whitehurst et al. |
| 2005/0125045 A1 | 6/2005 | Brighton et al. |
| 2005/0203588 A1 | 9/2005 | King |
| 2005/0205961 A1 | 9/2005 | Doong |
| 2005/0209655 A1 | 9/2005 | Bradley et al. |
| 2005/0231186 A1 | 10/2005 | Saavedra Barrera et al. |
| 2005/0239612 A1 | 10/2005 | Keiser |
| 2005/0246004 A1 | 11/2005 | Cameron et al. |
| 2005/0253273 A1 | 11/2005 | Tai et al. |
| 2005/0277999 A1 | 12/2005 | Strother et al. |
| 2005/0278000 A1 | 12/2005 | Strother et al. |
| 2006/0003090 A1 | 1/2006 | Rodger et al. |
| 2006/0007983 A1 | 1/2006 | Tai et al. |
| 2006/0015153 A1 | 1/2006 | Gliner et al. |
| 2006/0015470 A1 | 1/2006 | Lauer et al. |
| 2006/0016266 A1 | 1/2006 | Weise et al. |
| 2006/0018360 A1 | 1/2006 | Tai et al. |
| 2006/0041225 A1 | 2/2006 | Wallace et al. |
| 2006/0041295 A1 | 2/2006 | Osypka |
| 2006/0047325 A1 | 3/2006 | Thimineur et al. |
| 2006/0075339 A1 | 4/2006 | Tomita et al. |
| 2006/0082626 A1 | 4/2006 | Oikawa et al. |
| 2006/0089696 A1 | 4/2006 | Olsen et al. |
| 2006/0095088 A1 | 5/2006 | De Ridder |
| 2006/0100671 A1 | 5/2006 | De Ridder |
| 2006/0111754 A1 | 5/2006 | Rezai et al. |
| 2006/0122678 A1 | 6/2006 | Olsen et al. |
| 2006/0142337 A1 | 6/2006 | Ikeura et al. |
| 2006/0142816 A1 | 6/2006 | Fruitman et al. |
| 2006/0142822 A1 | 6/2006 | Tulgar |
| 2006/0149333 A1 | 7/2006 | Tanagho et al. |
| 2006/0149337 A1 | 7/2006 | John |
| 2006/0189453 A1 | 8/2006 | Leblond |
| 2006/0189839 A1 | 8/2006 | Laniado et al. |
| 2006/0195153 A1 | 8/2006 | Diubaldi et al. |
| 2006/0239482 A1 | 10/2006 | Hatoum |
| 2006/0241356 A1 | 10/2006 | Flaherty |
| 2006/0282127 A1 | 12/2006 | Zealear |
| 2007/0004567 A1 | 1/2007 | Shetty et al. |
| 2007/0009968 A1 | 1/2007 | Cunningham et al. |
| 2007/0016097 A1 | 1/2007 | Farquhar et al. |
| 2007/0016266 A1 | 1/2007 | Paul, Jr. |
| 2007/0016268 A1 | 1/2007 | Carter et al. |
| 2007/0016329 A1 | 1/2007 | Herr et al. |
| 2007/0021513 A1 | 1/2007 | Agee et al. |
| 2007/0027495 A1 | 2/2007 | Gerber |
| 2007/0047852 A1 | 3/2007 | Sharp et al. |
| 2007/0049814 A1 | 3/2007 | Muccio |
| 2007/0055318 A1 | 3/2007 | Forsberg et al. |
| 2007/0055337 A1 | 3/2007 | Tanrisever |
| 2007/0060954 A1 | 3/2007 | Cameron et al. |
| 2007/0060980 A1 | 3/2007 | Strother et al. |
| 2007/0067003 A1 | 3/2007 | Sanchez et al. |
| 2007/0073357 A1 | 3/2007 | Rooney et al. |
| 2007/0083240 A1 | 4/2007 | Peterson et al. |
| 2007/0100389 A1 | 5/2007 | Jaax et al. |
| 2007/0121702 A1 | 5/2007 | Laguardia et al. |
| 2007/0121709 A1 | 5/2007 | Ittogi |
| 2007/0129769 A1 | 6/2007 | Bourget et al. |
| 2007/0142874 A1 | 6/2007 | John |
| 2007/0142878 A1 | 6/2007 | Krulevitch et al. |
| 2007/0150023 A1 | 6/2007 | Ignagni et al. |
| 2007/0150034 A1 | 6/2007 | Rooney et al. |
| 2007/0156172 A1 | 7/2007 | Alvarado |
| 2007/0156179 A1 | 7/2007 | Karashurov |
| 2007/0156200 A1 | 7/2007 | Kornet et al. |
| 2007/0168008 A1 | 7/2007 | Olsen |
| 2007/0179534 A1 | 8/2007 | Firlik et al. |
| 2007/0179579 A1 | 8/2007 | Feler et al. |
| 2007/0191709 A1 | 8/2007 | Swanson |
| 2007/0208381 A1 | 9/2007 | Hill et al. |
| 2007/0233204 A1 | 10/2007 | Lima et al. |
| 2007/0250119 A1 | 10/2007 | Tyler et al. |
| 2007/0255372 A1 | 11/2007 | Metzler et al. |
| 2007/0265621 A1 | 11/2007 | Matthis et al. |
| 2007/0265679 A1 | 11/2007 | Bradley et al. |
| 2007/0265691 A1 | 11/2007 | Swanson |
| 2007/0276449 A1 | 11/2007 | Gunter et al. |
| 2007/0276450 A1 | 11/2007 | Meadows et al. |
| 2007/0282378 A1 | 12/2007 | Huang et al. |
| 2007/0293910 A1 | 12/2007 | Strother et al. |
| 2008/0002227 A1 | 1/2008 | Tsujimoto |
| 2008/0004674 A1 | 1/2008 | King et al. |
| 2008/0009927 A1 | 1/2008 | Vilims |
| 2008/0021513 A1 | 1/2008 | Thacker et al. |
| 2008/0027346 A1 | 1/2008 | Litt et al. |
| 2008/0046049 A1 | 2/2008 | Skubitz et al. |
| 2008/0051851 A1 | 2/2008 | Lin |
| 2008/0071325 A1 | 3/2008 | Bradley |
| 2008/0077192 A1 | 3/2008 | Harry et al. |
| 2008/0092911 A1 | 4/2008 | Schulman et al. |
| 2008/0103579 A1 | 5/2008 | Gerber |
| 2008/0105185 A1 | 5/2008 | Kuhlman |
| 2008/0127031 A1 | 5/2008 | Olsson et al. |
| 2008/0140152 A1 | 6/2008 | Imran et al. |
| 2008/0140162 A1 | 6/2008 | Goetz et al. |
| 2008/0140169 A1 | 6/2008 | Imran |
| 2008/0147143 A1 | 6/2008 | Popovic et al. |
| 2008/0154329 A1 | 6/2008 | Pyles et al. |
| 2008/0183097 A1 | 7/2008 | Leyde et al. |
| 2008/0183224 A1 | 7/2008 | Barolat |
| 2008/0200749 A1 | 8/2008 | Zheng et al. |
| 2008/0202940 A1 | 8/2008 | Jiang et al. |
| 2008/0207985 A1 | 8/2008 | Farone |
| 2008/0208287 A1 | 8/2008 | Palermo et al. |
| 2008/0215113 A1 | 9/2008 | Pawlowicz |
| 2008/0221653 A1 | 9/2008 | Agrawal et al. |
| 2008/0224226 A1 | 9/2008 | Suzuki et al. |
| 2008/0228241 A1 | 9/2008 | Sachs |
| 2008/0228250 A1 | 9/2008 | Mironer |
| 2008/0234121 A1 | 9/2008 | Kim et al. |
| 2008/0234791 A1 | 9/2008 | Arle et al. |
| 2008/0255582 A1 | 10/2008 | Harris |
| 2008/0269854 A1 | 10/2008 | Hegland et al. |
| 2008/0275129 A1 | 11/2008 | Lundstedt et al. |
| 2008/0279896 A1 | 11/2008 | Heinen et al. |
| 2008/0287268 A1 | 11/2008 | Hidler |
| 2008/0294211 A1 | 11/2008 | Moffitt |
| 2008/0294226 A1 | 11/2008 | Moffitt et al. |
| 2008/0318733 A1 | 12/2008 | Osler-Weppenaar |
| 2009/0005844 A1 | 1/2009 | Swoyer et al. |
| 2009/0012436 A1 | 1/2009 | Lanfermann et al. |
| 2009/0024186 A1 | 1/2009 | Brockway |
| 2009/0024997 A1 | 1/2009 | Kobayashi |
| 2009/0093854 A1 | 4/2009 | Leung et al. |
| 2009/0112281 A1 | 4/2009 | Miyazawa et al. |
| 2009/0118365 A1 | 5/2009 | Benson, III et al. |
| 2009/0131995 A1 | 5/2009 | Sloan et al. |
| 2009/0157141 A1 | 6/2009 | Chiao et al. |
| 2009/0198305 A1 | 8/2009 | Naroditsky et al. |

(56)          References Cited

U.S. PATENT DOCUMENTS

| | | |
|---|---|---|
| 2009/0204173 A1 | 8/2009 | Fang et al. |
| 2009/0227925 A1 | 9/2009 | Mcbean et al. |
| 2009/0229166 A1 | 9/2009 | Sawrie |
| 2009/0254151 A1 | 10/2009 | Anderson et al. |
| 2009/0270960 A1 | 10/2009 | Zhao et al. |
| 2009/0281529 A1 | 11/2009 | Carriazo |
| 2009/0281599 A1 | 11/2009 | Thacker et al. |
| 2009/0293270 A1 | 12/2009 | Brindley et al. |
| 2009/0299166 A1 | 12/2009 | Nishida et al. |
| 2009/0299167 A1 | 12/2009 | Seymour |
| 2009/0306491 A1 | 12/2009 | Haggers |
| 2009/0312165 A1 | 12/2009 | Rempe |
| 2010/0004715 A1 | 1/2010 | Fahey |
| 2010/0006737 A1 | 1/2010 | Colombo et al. |
| 2010/0008782 A1 | 1/2010 | Danescu et al. |
| 2010/0010646 A1 | 1/2010 | Drew et al. |
| 2010/0016732 A1 | 1/2010 | Wells et al. |
| 2010/0023069 A1 | 1/2010 | Moffitt et al. |
| 2010/0023070 A1 | 1/2010 | Moffitt et al. |
| 2010/0023103 A1 | 1/2010 | Elborno |
| 2010/0029040 A1 | 2/2010 | Nomoto |
| 2010/0042193 A1 | 2/2010 | Slavin |
| 2010/0048358 A1 | 2/2010 | Tchao et al. |
| 2010/0057177 A1 | 3/2010 | Moffitt et al. |
| 2010/0063568 A1 | 3/2010 | Staunton et al. |
| 2010/0070007 A1 | 3/2010 | Parker et al. |
| 2010/0070010 A1 | 3/2010 | Simpson |
| 2010/0087782 A1 | 4/2010 | Ghaffari et al. |
| 2010/0094800 A1 | 4/2010 | Sharp |
| 2010/0114205 A1 | 5/2010 | Donofrio et al. |
| 2010/0114239 A1 | 5/2010 | Mcdonald, III |
| 2010/0116526 A1 | 5/2010 | Arora et al. |
| 2010/0125313 A1 | 5/2010 | Lee et al. |
| 2010/0137238 A1 | 6/2010 | Gan et al. |
| 2010/0137938 A1 | 6/2010 | Kishawi et al. |
| 2010/0137943 A1 | 6/2010 | Zhu |
| 2010/0145428 A1 | 6/2010 | Cameron et al. |
| 2010/0152811 A1 | 6/2010 | Flaherty |
| 2010/0166546 A1 | 7/2010 | Mahan et al. |
| 2010/0168820 A1 | 7/2010 | Maniak et al. |
| 2010/0179562 A1 | 7/2010 | Linker et al. |
| 2010/0185253 A1 | 7/2010 | Dimarco et al. |
| 2010/0191307 A1 | 7/2010 | Fang et al. |
| 2010/0198298 A1 | 8/2010 | Glukhovsky et al. |
| 2010/0217355 A1 | 8/2010 | Tass et al. |
| 2010/0217418 A1 | 8/2010 | Fontanot |
| 2010/0228310 A1 | 9/2010 | Shuros et al. |
| 2010/0241121 A1 | 9/2010 | Logan et al. |
| 2010/0241191 A1 | 9/2010 | Testerman et al. |
| 2010/0268299 A1 | 10/2010 | Farone |
| 2010/0274312 A1 | 10/2010 | Alataris et al. |
| 2010/0279606 A1 | 11/2010 | Hillan et al. |
| 2010/0280570 A1 | 11/2010 | Sturm et al. |
| 2010/0298905 A1 | 11/2010 | Simon |
| 2010/0298910 A1 | 11/2010 | Carbunaru et al. |
| 2010/0305660 A1 | 12/2010 | Hegi et al. |
| 2010/0312304 A1 | 12/2010 | York et al. |
| 2010/0318168 A1 | 12/2010 | Bighetti |
| 2010/0324699 A1 | 12/2010 | Herr et al. |
| 2010/0331925 A1 | 12/2010 | Peterson |
| 2011/0006793 A1 | 1/2011 | Peschke et al. |
| 2011/0009919 A1 | 1/2011 | Carbunaru et al. |
| 2011/0016081 A1 | 1/2011 | Basak et al. |
| 2011/0029040 A1 | 2/2011 | Walker et al. |
| 2011/0029044 A1 | 2/2011 | Hyde et al. |
| 2011/0034277 A1 | 2/2011 | Brandes |
| 2011/0034912 A1 | 2/2011 | De Graff et al. |
| 2011/0034977 A1 | 2/2011 | Janik et al. |
| 2011/0040349 A1 | 2/2011 | Graupe |
| 2011/0054567 A1 | 3/2011 | Lane et al. |
| 2011/0054568 A1 | 3/2011 | Lane et al. |
| 2011/0054570 A1 | 3/2011 | Lane |
| 2011/0054579 A1 | 3/2011 | Kumar et al. |
| 2011/0060461 A1 | 3/2011 | Velliste et al. |
| 2011/0077660 A1 | 3/2011 | Janik et al. |
| 2011/0082515 A1 | 4/2011 | Libbus et al. |
| 2011/0084489 A1 | 4/2011 | Kaplan |
| 2011/0093043 A1 | 4/2011 | Torgerson et al. |
| 2011/0112601 A1 | 5/2011 | Meadows et al. |
| 2011/0112611 A1 | 5/2011 | Aghassian |
| 2011/0118815 A1 | 5/2011 | Kuzma et al. |
| 2011/0125203 A1 | 5/2011 | Simon et al. |
| 2011/0130804 A1 | 6/2011 | Lin et al. |
| 2011/0152967 A1 | 6/2011 | Simon et al. |
| 2011/0160810 A1 | 6/2011 | Griffith |
| 2011/0166546 A1 | 7/2011 | Jaax et al. |
| 2011/0184482 A1 | 7/2011 | Eberman et al. |
| 2011/0184488 A1 | 7/2011 | De Ridder |
| 2011/0184489 A1 | 7/2011 | Nicolelis et al. |
| 2011/0201944 A1 | 8/2011 | Higgins et al. |
| 2011/0202107 A1 | 8/2011 | Sunagawa et al. |
| 2011/0208265 A1 | 8/2011 | Erickson et al. |
| 2011/0213266 A1 | 9/2011 | Williams et al. |
| 2011/0218590 A1 | 9/2011 | Degiorgio et al. |
| 2011/0218594 A1 | 9/2011 | Doron et al. |
| 2011/0224153 A1 | 9/2011 | Levitt et al. |
| 2011/0224665 A1 | 9/2011 | Crosby et al. |
| 2011/0224752 A1 | 9/2011 | Rolston et al. |
| 2011/0224753 A1 | 9/2011 | Palermo et al. |
| 2011/0224755 A1 | 9/2011 | Arie et al. |
| 2011/0224757 A1 | 9/2011 | Zdeblick et al. |
| 2011/0230101 A1 | 9/2011 | Tang et al. |
| 2011/0230701 A1 | 9/2011 | Simon et al. |
| 2011/0230702 A1 | 9/2011 | Honour |
| 2011/0230747 A1 | 9/2011 | Rogers et al. |
| 2011/0230808 A1 | 9/2011 | Lisowski |
| 2011/0231326 A1 | 9/2011 | Marino |
| 2011/0237221 A1 | 9/2011 | Prakash et al. |
| 2011/0237921 A1 | 9/2011 | Askin et al. |
| 2011/0245734 A1 | 10/2011 | Wagner et al. |
| 2011/0260126 A1 | 10/2011 | Willis |
| 2011/0270360 A1 | 11/2011 | Harris et al. |
| 2011/0276107 A1 | 11/2011 | Simon et al. |
| 2011/0288609 A1 | 11/2011 | Tehrani et al. |
| 2011/0295100 A1 | 12/2011 | Hegde et al. |
| 2012/0006793 A1 | 1/2012 | Swanson |
| 2012/0011222 A1 | 1/2012 | Yasukawa et al. |
| 2012/0011950 A1 | 1/2012 | Kracke |
| 2012/0013041 A1 | 1/2012 | Cao et al. |
| 2012/0013126 A1 | 1/2012 | Molloy |
| 2012/0016448 A1 | 1/2012 | Lee |
| 2012/0016453 A1 | 1/2012 | Feler et al. |
| 2012/0018249 A1 | 1/2012 | Mehr |
| 2012/0022371 A1 | 1/2012 | Summerton |
| 2012/0022551 A1 | 1/2012 | Staunton et al. |
| 2012/0029528 A1 | 2/2012 | Macdonald et al. |
| 2012/0035684 A1 | 2/2012 | Thompson et al. |
| 2012/0036552 A1 | 2/2012 | Dare et al. |
| 2012/0041518 A1 | 2/2012 | Kim et al. |
| 2012/0052432 A1 | 3/2012 | Matsuura |
| 2012/0053645 A1 | 3/2012 | Ayanoor-Vitikkate et al. |
| 2012/0059432 A1 | 3/2012 | Emborg et al. |
| 2012/0071250 A1 | 3/2012 | O'Neil et al. |
| 2012/0071950 A1 | 3/2012 | Archer |
| 2012/0083709 A1 | 4/2012 | Parker et al. |
| 2012/0101326 A1 | 4/2012 | Simon et al. |
| 2012/0109251 A1 | 5/2012 | Lebedev et al. |
| 2012/0109295 A1 | 5/2012 | Fan |
| 2012/0116476 A1 | 5/2012 | Kothandaraman |
| 2012/0116478 A1 | 5/2012 | Buhlmann et al. |
| 2012/0123223 A1 | 5/2012 | Freeman et al. |
| 2012/0123293 A1 | 5/2012 | Shah et al. |
| 2012/0126392 A1 | 5/2012 | Kalvesten et al. |
| 2012/0136408 A1 | 5/2012 | Grill et al. |
| 2012/0143281 A1 | 6/2012 | Birkill et al. |
| 2012/0161531 A1 | 6/2012 | Kim |
| 2012/0161721 A1 | 6/2012 | Neethimanickam |
| 2012/0165899 A1 | 6/2012 | Gliner |
| 2012/0168397 A1 | 7/2012 | Lim et al. |
| 2012/0172222 A1 | 7/2012 | Artigas Puerto |
| 2012/0172246 A1 | 7/2012 | Nguyen et al. |
| 2012/0172510 A1 | 7/2012 | Esseghir et al. |
| 2012/0172946 A1 | 7/2012 | Alataris et al. |
| 2012/0179222 A1 | 7/2012 | Jaax et al. |

(56) References Cited

U.S. PATENT DOCUMENTS

| | | |
|---|---|---|
| 2012/0185020 A1 | 7/2012 | Simon et al. |
| 2012/0197338 A1 | 8/2012 | Su et al. |
| 2012/0203055 A1 | 8/2012 | Pletnev |
| 2012/0203131 A1 | 8/2012 | Dilorenzo |
| 2012/0203246 A1 | 8/2012 | Staunton et al. |
| 2012/0221073 A1 | 8/2012 | Southwell et al. |
| 2012/0232615 A1 | 9/2012 | Barolat et al. |
| 2012/0252380 A1 | 10/2012 | Kawakita |
| 2012/0252874 A1 | 10/2012 | Feinstein et al. |
| 2012/0259380 A1 | 10/2012 | Pyles |
| 2012/0265269 A1 | 10/2012 | Lui |
| 2012/0271315 A1 | 10/2012 | Pianca et al. |
| 2012/0271372 A1 | 10/2012 | Osorio |
| 2012/0277824 A1 | 11/2012 | Li |
| 2012/0277834 A1 | 11/2012 | Mercanzini et al. |
| 2012/0283697 A1 | 11/2012 | Kim et al. |
| 2012/0283797 A1 | 11/2012 | De Ridder |
| 2012/0302821 A1 | 11/2012 | Burnett |
| 2012/0310302 A1 | 12/2012 | Bennett et al. |
| 2012/0310305 A1 | 12/2012 | Kaula et al. |
| 2012/0310315 A1 | 12/2012 | Savage et al. |
| 2012/0330321 A1 | 12/2012 | Johnson et al. |
| 2012/0330391 A1 | 12/2012 | Bradley et al. |
| 2013/0006322 A1 | 1/2013 | Tai |
| 2013/0006793 A1 | 1/2013 | O'Sullivan et al. |
| 2013/0012853 A1 | 1/2013 | Brown |
| 2013/0013041 A1 | 1/2013 | Glukhovsky et al. |
| 2013/0023972 A1 | 1/2013 | Kuzma et al. |
| 2013/0026640 A1 | 1/2013 | Ito et al. |
| 2013/0030312 A1 | 1/2013 | Keel et al. |
| 2013/0030319 A1 | 1/2013 | Hettrick et al. |
| 2013/0030501 A1 | 1/2013 | Feler et al. |
| 2013/0032508 A1 | 2/2013 | Azuma |
| 2013/0035745 A1 | 2/2013 | Ahmed et al. |
| 2013/0041235 A1 | 2/2013 | Rogers et al. |
| 2013/0053734 A1 | 2/2013 | Barriskill et al. |
| 2013/0053922 A1 | 2/2013 | Ahmed et al. |
| 2013/0066392 A1 | 3/2013 | Simon et al. |
| 2013/0066411 A1 | 3/2013 | Thacker et al. |
| 2013/0085317 A1 | 4/2013 | Feinstein |
| 2013/0085361 A1 | 4/2013 | Mercanzini et al. |
| 2013/0096640 A1 | 4/2013 | Passover |
| 2013/0096661 A1 | 4/2013 | Greenberg et al. |
| 2013/0096662 A1 | 4/2013 | Swanson |
| 2013/0110196 A1 | 5/2013 | Alataris et al. |
| 2013/0116604 A1 | 5/2013 | Marilla et al. |
| 2013/0116751 A1 | 5/2013 | Moffitt et al. |
| 2013/0123568 A1 | 5/2013 | Hamilton et al. |
| 2013/0123659 A1 | 5/2013 | Bartol et al. |
| 2013/0138167 A1 | 5/2013 | Bradley et al. |
| 2013/0150915 A1 | 6/2013 | Kane et al. |
| 2013/0154373 A1 | 6/2013 | Lisuwandi et al. |
| 2013/0158444 A1 | 6/2013 | Herr et al. |
| 2013/0165991 A1 | 6/2013 | Kim et al. |
| 2013/0190143 A1 | 7/2013 | Greenhill et al. |
| 2013/0197408 A1 | 8/2013 | Goldfarb et al. |
| 2013/0204324 A1 | 8/2013 | Thacker et al. |
| 2013/0211477 A1 | 8/2013 | Cullen et al. |
| 2013/0226263 A1 | 8/2013 | Kelly et al. |
| 2013/0237948 A1 | 9/2013 | Donders et al. |
| 2013/0245712 A1 | 9/2013 | Simon et al. |
| 2013/0253222 A1 | 9/2013 | Nakao |
| 2013/0253229 A1 | 9/2013 | Sawant et al. |
| 2013/0253299 A1 | 9/2013 | Weber et al. |
| 2013/0253611 A1 | 9/2013 | Lee et al. |
| 2013/0268016 A1 | 10/2013 | Xi et al. |
| 2013/0268020 A1 | 10/2013 | Rosenberg et al. |
| 2013/0268021 A1 | 10/2013 | Moffitt |
| 2013/0268041 A1 | 10/2013 | Schulte et al. |
| 2013/0281890 A1 | 10/2013 | Mishelevich |
| 2013/0289446 A1 | 10/2013 | Stone et al. |
| 2013/0289650 A1 | 10/2013 | Karlsson et al. |
| 2013/0289664 A1 | 10/2013 | Johanek |
| 2013/0289667 A1 | 10/2013 | Wacnik et al. |
| 2013/0296965 A1 | 11/2013 | Mokelke et al. |
| 2013/0303873 A1 | 11/2013 | Voros et al. |
| 2013/0304159 A1 | 11/2013 | Simon et al. |
| 2013/0310211 A1 | 11/2013 | Wilton et al. |
| 2013/0310911 A1 | 11/2013 | Tai et al. |
| 2013/0325081 A1 | 12/2013 | Karst et al. |
| 2013/0325083 A1 | 12/2013 | Bharmi et al. |
| 2013/0345780 A1 | 12/2013 | Tabada et al. |
| 2014/0005753 A1 | 1/2014 | Carbunaru |
| 2014/0031893 A1 | 1/2014 | Walker et al. |
| 2014/0031895 A1 | 1/2014 | Rahimi et al. |
| 2014/0046407 A1 | 2/2014 | Ben-Ezra et al. |
| 2014/0053401 A1 | 2/2014 | Kuzma et al. |
| 2014/0058292 A1 | 2/2014 | Alford et al. |
| 2014/0058490 A1 | 2/2014 | Dimarco |
| 2014/0059499 A1 | 2/2014 | Kim et al. |
| 2014/0066950 A1 | 3/2014 | Macdonald et al. |
| 2014/0067007 A1 | 3/2014 | Drees et al. |
| 2014/0067013 A1 | 3/2014 | Kaula et al. |
| 2014/0067354 A1 | 3/2014 | Kaula et al. |
| 2014/0074190 A1 | 3/2014 | Griffith |
| 2014/0081011 A1 | 3/2014 | Vaught et al. |
| 2014/0081071 A1 | 3/2014 | Simon et al. |
| 2014/0081345 A1 | 3/2014 | Hershey |
| 2014/0087922 A1 | 3/2014 | Bayerlein et al. |
| 2014/0088674 A1 | 3/2014 | Bradley |
| 2014/0100491 A1 | 4/2014 | Hu et al. |
| 2014/0100633 A1 | 4/2014 | Mann et al. |
| 2014/0107397 A1 | 4/2014 | Simon et al. |
| 2014/0107398 A1 | 4/2014 | Simon et al. |
| 2014/0114374 A1 | 4/2014 | Rooney et al. |
| 2014/0114385 A1 | 4/2014 | Nijhuis et al. |
| 2014/0124713 A1 | 5/2014 | Majumdar et al. |
| 2014/0142652 A1 | 5/2014 | Francois et al. |
| 2014/0163640 A1 | 6/2014 | Edgerton et al. |
| 2014/0171961 A1 | 6/2014 | Lacey et al. |
| 2014/0172045 A1 | 6/2014 | Yip et al. |
| 2014/0172055 A1 | 6/2014 | Venancio |
| 2014/0180361 A1 | 6/2014 | Burdick et al. |
| 2014/0200387 A1 | 7/2014 | Ahmed |
| 2014/0201905 A1 | 7/2014 | Glukhovsky |
| 2014/0213842 A1 | 7/2014 | Simon et al. |
| 2014/0213844 A1 | 7/2014 | Pilla et al. |
| 2014/0228905 A1 | 8/2014 | Bolea |
| 2014/0236257 A1 | 8/2014 | Parker et al. |
| 2014/0243923 A1 | 8/2014 | Doan et al. |
| 2014/0257016 A1 | 9/2014 | Ahmed |
| 2014/0277271 A1 | 9/2014 | Chan et al. |
| 2014/0296752 A1 | 10/2014 | Edgerton et al. |
| 2014/0303685 A1 | 10/2014 | Rosenberg et al. |
| 2014/0303901 A1 | 10/2014 | Sadeh |
| 2014/0316484 A1 | 10/2014 | Edgerton et al. |
| 2014/0316503 A1 | 10/2014 | Tai et al. |
| 2014/0324118 A1 | 10/2014 | Simon et al. |
| 2014/0330067 A1 | 11/2014 | Jordan |
| 2014/0330335 A1 | 11/2014 | Errico et al. |
| 2014/0336722 A1 | 11/2014 | Rocon De Lima et al. |
| 2014/0339909 A1 | 11/2014 | Sugawara |
| 2014/0343623 A1 | 11/2014 | Alves et al. |
| 2014/0344740 A1 | 11/2014 | Kaula et al. |
| 2014/0357936 A1 | 12/2014 | Simon et al. |
| 2014/0359521 A1 | 12/2014 | Lin et al. |
| 2014/0371830 A1 | 12/2014 | Howard et al. |
| 2015/0005167 A1 | 1/2015 | Jung et al. |
| 2015/0005840 A1 | 1/2015 | Pal et al. |
| 2015/0012061 A1 | 1/2015 | Chen |
| 2015/0022143 A1 | 1/2015 | Kim |
| 2015/0032187 A1 | 1/2015 | Ranu et al. |
| 2015/0051674 A1 | 2/2015 | Barner et al. |
| 2015/0057717 A1 | 2/2015 | Wu et al. |
| 2015/0065559 A1 | 3/2015 | Feinstein et al. |
| 2015/0066111 A1 | 3/2015 | Blum et al. |
| 2015/0074997 A1 | 3/2015 | Kuzma et al. |
| 2015/0088212 A1 | 3/2015 | De Ridder |
| 2015/0094734 A1 | 4/2015 | Staunton et al. |
| 2015/0094791 A1 | 4/2015 | Edgell et al. |
| 2015/0120634 A1 | 4/2015 | Tateno |
| 2015/0126120 A1 | 5/2015 | Chen |
| 2015/0148878 A1 | 5/2015 | Yoo et al. |
| 2015/0151114 A1 | 6/2015 | Black et al. |

(56) References Cited

U.S. PATENT DOCUMENTS

| | | |
|---|---|---|
| 2015/0151126 A1 | 6/2015 | Kishawi et al. |
| 2015/0165226 A1 | 6/2015 | Simon et al. |
| 2015/0174411 A1 | 6/2015 | Ranu |
| 2015/0182784 A1 | 7/2015 | Barriskill et al. |
| 2015/0188592 A1 | 7/2015 | Solondz |
| 2015/0190200 A1 | 7/2015 | Courtine et al. |
| 2015/0190634 A1 | 7/2015 | Rezai et al. |
| 2015/0196231 A1 | 7/2015 | Ziaie et al. |
| 2015/0196241 A1 | 7/2015 | Yekutieli |
| 2015/0200561 A1 | 7/2015 | Lee et al. |
| 2015/0217120 A1 | 8/2015 | Nandra et al. |
| 2015/0224326 A1 | 8/2015 | Toth et al. |
| 2015/0231326 A1 | 8/2015 | Milner et al. |
| 2015/0231396 A1 | 8/2015 | Burdick et al. |
| 2015/0246216 A1 | 9/2015 | Barker |
| 2015/0265830 A1 | 9/2015 | Simon et al. |
| 2015/0268845 A1 | 9/2015 | Endo |
| 2015/0320632 A1 | 11/2015 | Vallery et al. |
| 2015/0328462 A1 | 11/2015 | Griffith |
| 2015/0343199 A1 | 12/2015 | Wechter et al. |
| 2015/0343205 A1 | 12/2015 | Howard et al. |
| 2016/0001096 A1 | 1/2016 | Mishelevich |
| 2016/0005538 A1 | 1/2016 | Koyanagi et al. |
| 2016/0030737 A1 | 2/2016 | Gerasimenko et al. |
| 2016/0030748 A1 | 2/2016 | Edgerton et al. |
| 2016/0030750 A1 | 2/2016 | Bokil et al. |
| 2016/0045727 A1 | 2/2016 | Rezai et al. |
| 2016/0045731 A1 | 2/2016 | Simon et al. |
| 2016/0067477 A1 | 3/2016 | Dubuclet |
| 2016/0074663 A1 | 3/2016 | De Ridder |
| 2016/0082261 A1 | 3/2016 | Moffitt et al. |
| 2016/0121109 A1 | 5/2016 | Edgerton et al. |
| 2016/0121114 A1 | 5/2016 | Simon et al. |
| 2016/0121116 A1 | 5/2016 | Simon et al. |
| 2016/0121121 A1 | 5/2016 | Mashiach |
| 2016/0136477 A1 | 5/2016 | Bucher et al. |
| 2016/0143588 A1 | 5/2016 | Hoitink et al. |
| 2016/0144167 A1 | 5/2016 | Bakker et al. |
| 2016/0144184 A1 | 5/2016 | Marnfeldt |
| 2016/0157389 A1 | 6/2016 | Hwang |
| 2016/0166828 A1 | 6/2016 | Yu |
| 2016/0175586 A1 | 6/2016 | Edgerton et al. |
| 2016/0197488 A1 | 7/2016 | Hada et al. |
| 2016/0213918 A1 | 7/2016 | Howard et al. |
| 2016/0220813 A1 | 8/2016 | Edgerton et al. |
| 2016/0228706 A1 | 8/2016 | Hershey et al. |
| 2016/0235977 A1 | 8/2016 | Lu et al. |
| 2016/0250461 A1 | 9/2016 | Dubuclet |
| 2016/0263376 A1 | 9/2016 | Yoo et al. |
| 2016/0271413 A1 | 9/2016 | Vallejo et al. |
| 2016/0279418 A1 | 9/2016 | Courtine et al. |
| 2016/0279429 A1 | 9/2016 | Hershey et al. |
| 2016/0291848 A1 | 10/2016 | Hall et al. |
| 2016/0310739 A1 | 10/2016 | Burdick et al. |
| 2016/0339239 A1 | 11/2016 | Yoo et al. |
| 2016/0367827 A1 | 12/2016 | Tahmasian |
| 2017/0007320 A1 | 1/2017 | Levin et al. |
| 2017/0007831 A1 | 1/2017 | Edgerton et al. |
| 2017/0014620 A9 | 1/2017 | Staunton et al. |
| 2017/0014622 A1 | 1/2017 | Bozung et al. |
| 2017/0065814 A1 | 3/2017 | Howard et al. |
| 2017/0079598 A1 | 3/2017 | Stolen et al. |
| 2017/0098951 A1 | 4/2017 | Olgun et al. |
| 2017/0098962 A1 | 4/2017 | Desrosiers |
| 2017/0118722 A1 | 4/2017 | Hong et al. |
| 2017/0128729 A1 | 5/2017 | Netoff et al. |
| 2017/0156662 A1 | 6/2017 | Goodall et al. |
| 2017/0157389 A1 | 6/2017 | Tai et al. |
| 2017/0157396 A1 | 6/2017 | Dixon et al. |
| 2017/0161454 A1 | 6/2017 | Grill et al. |
| 2017/0165497 A1 | 6/2017 | Lu |
| 2017/0173326 A1 | 6/2017 | Bloch et al. |
| 2017/0189686 A1 | 7/2017 | Steinke et al. |
| 2017/0239486 A1 | 8/2017 | Suryavanshi |
| 2017/0246450 A1 | 8/2017 | Liu et al. |
| 2017/0246452 A1 | 8/2017 | Liu et al. |
| 2017/0266455 A1 | 9/2017 | Steinke |
| 2017/0274209 A1 | 9/2017 | Edgerton et al. |
| 2017/0291023 A1 | 10/2017 | Kuzma et al. |
| 2017/0296837 A1 | 10/2017 | Jin |
| 2017/0338570 A1 | 11/2017 | Myers |
| 2017/0348523 A1 | 12/2017 | Rubehn et al. |
| 2017/0348532 A1 | 12/2017 | Moffitt et al. |
| 2017/0354819 A1 | 12/2017 | Bloch et al. |
| 2017/0361093 A1 | 12/2017 | Yoo et al. |
| 2017/0361115 A1 | 12/2017 | Aghassian et al. |
| 2018/0008826 A1 | 1/2018 | Dimarco |
| 2018/0028812 A1 | 2/2018 | Vallejo et al. |
| 2018/0056078 A1 | 3/2018 | Kashyap et al. |
| 2018/0083473 A1 | 3/2018 | Menegoli et al. |
| 2018/0085582 A1 | 3/2018 | Calle et al. |
| 2018/0085583 A1 | 3/2018 | Zhang et al. |
| 2018/0093093 A1 | 4/2018 | Courtine et al. |
| 2018/0104479 A1 | 4/2018 | Grill et al. |
| 2018/0110992 A1 | 4/2018 | Parramon et al. |
| 2018/0117334 A1 | 5/2018 | Jung |
| 2018/0125416 A1 | 5/2018 | Schwarz et al. |
| 2018/0125419 A1 | 5/2018 | Yun et al. |
| 2018/0126154 A1 | 5/2018 | Dubuclet |
| 2018/0126155 A1 | 5/2018 | Mclaughlin et al. |
| 2018/0133480 A1 | 5/2018 | Annoni et al. |
| 2018/0133481 A1 | 5/2018 | Von Zitzewitz et al. |
| 2018/0153474 A1 | 6/2018 | Aeschlimann et al. |
| 2018/0178008 A1 | 6/2018 | Bouton et al. |
| 2018/0185632 A1 | 7/2018 | Staunton et al. |
| 2018/0185642 A1 | 7/2018 | Lu |
| 2018/0185648 A1 | 7/2018 | Nandra et al. |
| 2018/0193655 A1 | 7/2018 | Zhang et al. |
| 2018/0214694 A1 | 8/2018 | Parramon |
| 2018/0221620 A1 | 8/2018 | Metzger |
| 2018/0221651 A1 | 8/2018 | Chang et al. |
| 2018/0228421 A1 | 8/2018 | Saab |
| 2018/0229037 A1 | 8/2018 | Edgerton et al. |
| 2018/0229038 A1 | 8/2018 | Burdick et al. |
| 2018/0236240 A1 | 8/2018 | Harkema et al. |
| 2018/0256906 A1 | 9/2018 | Pivonka et al. |
| 2018/0272125 A1 | 9/2018 | Sandhu |
| 2018/0272132 A1 | 9/2018 | Subbaroyan et al. |
| 2018/0280693 A1 | 10/2018 | Edgerton et al. |
| 2018/0280706 A1 | 10/2018 | Maile et al. |
| 2018/0289971 A1 | 10/2018 | Yeh et al. |
| 2018/0294547 A1 | 10/2018 | Park et al. |
| 2018/0318576 A1 | 11/2018 | Bozung et al. |
| 2018/0326220 A1 | 11/2018 | Kaula et al. |
| 2018/0337547 A1 | 11/2018 | Menegoli et al. |
| 2018/0353755 A1 | 12/2018 | Edgerton et al. |
| 2018/0361146 A1 | 12/2018 | Gerasimenko et al. |
| 2018/0367187 A1 | 12/2018 | Mcfarthing |
| 2018/0369574 A1 | 12/2018 | Dubuclet et al. |
| 2018/0369575 A1 | 12/2018 | Dubuclet et al. |
| 2018/0369576 A1 | 12/2018 | Dubuclet et al. |
| 2019/0001122 A1 | 1/2019 | Ganty et al. |
| 2019/0001139 A1 | 1/2019 | Mishra et al. |
| 2019/0009094 A1 | 1/2019 | Zhang et al. |
| 2019/0017983 A1 | 1/2019 | Smith |
| 2019/0022371 A1 | 1/2019 | Chang et al. |
| 2019/0027257 A1 | 1/2019 | Ghogawala |
| 2019/0033622 A1 | 1/2019 | Olgun et al. |
| 2019/0160294 A1 | 5/2019 | Peterson et al. |
| 2019/0167980 A1 | 6/2019 | Peterson |
| 2019/0167987 A1 | 6/2019 | Lu et al. |
| 2019/0192852 A1 | 6/2019 | De Ridder |
| 2019/0192864 A1 | 6/2019 | Koop et al. |
| 2019/0240468 A1 | 8/2019 | Yun et al. |
| 2019/0247650 A1 | 8/2019 | Tran |
| 2019/0262609 A1 | 8/2019 | Brill et al. |
| 2019/0269917 A1 | 9/2019 | Courtine et al. |
| 2019/0299006 A1 | 10/2019 | Marnfeldt |
| 2019/0321639 A1 | 10/2019 | Rao et al. |
| 2019/0336760 A1 | 11/2019 | Shah |
| 2019/0344070 A1 | 11/2019 | Molnar et al. |
| 2019/0344075 A1 | 11/2019 | Bloch et al. |
| 2019/0358454 A1 | 11/2019 | Lin et al. |
| 2019/0374776 A1 | 12/2019 | Mishra et al. |

(56)　　References Cited

U.S. PATENT DOCUMENTS

| | | | |
|---|---|---|---|
| 2019/0374777 A1 | 12/2019 | Burdick et al. | |
| 2019/0381313 A1 | 12/2019 | Lu | |
| 2019/0381328 A1 | 12/2019 | Wechter et al. | |
| 2019/0381382 A1 | 12/2019 | Wu | |
| 2020/0009385 A1 | 1/2020 | Shah | |
| 2020/0060602 A1 | 2/2020 | Wagner et al. | |
| 2020/0061378 A1 | 2/2020 | Ganguly et al. | |
| 2020/0086116 A1* | 3/2020 | Formento | A61N 1/0551 |
| 2020/0121544 A1 | 4/2020 | George et al. | |
| 2020/0144846 A1 | 5/2020 | Shin | |
| 2020/0147382 A1 | 5/2020 | Caban et al. | |
| 2020/0155019 A1 | 5/2020 | Esteller et al. | |
| 2020/0155865 A1 | 5/2020 | Lu | |
| 2020/0228901 A1 | 7/2020 | Baek | |
| 2020/0360697 A1 | 11/2020 | Paoles et al. | |
| 2020/0398068 A1 | 12/2020 | Agnihotri et al. | |
| 2021/0069052 A1 | 3/2021 | Burke | |
| 2021/0093865 A1 | 4/2021 | Vallejo et al. | |
| 2021/0121692 A1 | 4/2021 | Edgerton et al. | |
| 2021/0153942 A1 | 5/2021 | Scheltienne et al. | |
| 2021/0154481 A1 | 5/2021 | Scheltienne et al. | |
| 2021/0170177 A1 | 6/2021 | Minassian et al. | |
| 2021/0170178 A1 | 6/2021 | Wagner et al. | |
| 2021/0187278 A1 | 6/2021 | Lu | |
| 2021/0213292 A1 | 7/2021 | Minassian et al. | |
| 2021/0236837 A1 | 8/2021 | Lu | |
| 2021/0275810 A1 | 9/2021 | Caban | |
| 2021/0290955 A1 | 9/2021 | Brouns et al. | |
| 2021/0299441 A1 | 9/2021 | Edgerton et al. | |
| 2021/0378991 A1 | 12/2021 | Lu | |
| 2021/0402186 A1 | 12/2021 | Edgerton et al. | |
| 2022/0016420 A1 | 1/2022 | Lo et al. | |
| 2022/0111208 A1 | 4/2022 | Phillips et al. | |
| 2022/0125374 A1 | 4/2022 | Courtine et al. | |
| 2022/0134108 A1 | 5/2022 | Dinsmoor et al. | |
| 2022/0143407 A1 | 5/2022 | Zhuang et al. | |
| 2022/0161042 A1 | 5/2022 | Lu et al. | |
| 2022/0176130 A1 | 6/2022 | Wu et al. | |
| 2022/0184386 A1 | 6/2022 | Courtine et al. | |
| 2022/0233848 A1 | 7/2022 | Gad et al. | |
| 2022/0313993 A1 | 10/2022 | Gerasimenko et al. | |
| 2022/0409899 A1 | 12/2022 | Ganty et al. | |
| 2023/0045403 A1 | 2/2023 | Robison et al. | |
| 2023/0053053 A1 | 2/2023 | Delattre et al. | |
| 2023/0186201 A1 | 6/2023 | Cella et al. | |
| 2023/0281527 A1 | 9/2023 | Cella et al. | |
| 2024/0001116 A1 | 1/2024 | Edgerton et al. | |
| 2024/0050746 A1* | 2/2024 | Angeli | A61N 1/36185 |
| 2024/0335666 A1 | 10/2024 | Murphy | |
| 2024/0374541 A1 | 11/2024 | Lu et al. | |
| 2024/0424291 A1 | 12/2024 | Ganty et al. | |
| 2024/0424302 A1 | 12/2024 | Dumeny | |
| 2025/0025689 A1 | 1/2025 | Lo et al. | |
| 2025/0032799 A1 | 1/2025 | Weijand et al. | |

FOREIGN PATENT DOCUMENTS

| | | | |
|---|---|---|---|
| CA | 2823592 A1 | 7/2012 | |
| CA | 2856202 A1 | 5/2013 | |
| CA | 2864473 A1 | 5/2013 | |
| CA | 3034123 A1 | 2/2018 | |
| CN | 101227940 A | 7/2008 | |
| CN | 101822223 A | 9/2010 | |
| CN | 103263727 A | 8/2013 | |
| CN | 104307098 A | 1/2015 | |
| DE | 3830429 A1 | 3/1990 | |
| DE | 202007015508 U1 | 3/2008 | |
| EP | 0034145 A1 | 8/1981 | |
| EP | 0236976 A1 | 9/1987 | |
| EP | 0630987 A1 | 12/1994 | |
| EP | 1127907 A2 | 8/2001 | |
| EP | 1303332 A1 | 4/2003 | |
| EP | 1575665 A1 | 9/2005 | |
| EP | 1675648 A1 | 7/2006 | |
| EP | 1680182 A1 | 7/2006 | |
| EP | 2130326 A1 | 12/2009 | |
| EP | 2141851 A2 | 1/2010 | |
| EP | 2160127 A1 | 3/2010 | |
| EP | 2178319 A1 | 4/2010 | |
| EP | 2192897 A1 | 6/2010 | |
| EP | 2226114 A1 | 9/2010 | |
| EP | 2243510 A2 | 10/2010 | |
| EP | 2258496 A1 | 12/2010 | |
| EP | 2361631 A1 | 8/2011 | |
| EP | 2368401 A1 | 9/2011 | |
| EP | 2387467 A1 | 11/2011 | |
| EP | 2396995 A1 | 12/2011 | |
| EP | 2397788 A1 | 12/2011 | |
| EP | 2445990 A2 | 5/2012 | |
| EP | 2471518 A2 | 7/2012 | |
| EP | 2475283 A1 | 7/2012 | |
| EP | 2486897 A2 | 8/2012 | |
| EP | 2626051 A1 | 8/2013 | |
| EP | 2628502 A1 | 8/2013 | |
| EP | 2661307 A2 | 11/2013 | |
| EP | 2665514 A2 | 11/2013 | |
| EP | 2688642 A2 | 1/2014 | |
| EP | 2810689 A1 | 12/2014 | |
| EP | 2810690 A1 | 12/2014 | |
| EP | 2868323 A1 | 5/2015 | |
| EP | 2868343 A1 | 5/2015 | |
| EP | 2966422 A1 | 1/2016 | |
| EP | 2968940 A1 | 1/2016 | |
| EP | 3184145 A1 | 6/2017 | |
| EP | 3269424 A1 | 1/2018 | |
| EP | 3323468 A1 | 5/2018 | |
| EP | 3328481 A1 | 6/2018 | |
| EP | 3381506 A1 | 10/2018 | |
| EP | 3421081 A1 | 1/2019 | |
| EP | 3285855 | 6/2019 | |
| EP | 3495019 A1 | 6/2019 | |
| EP | 3527258 A1 | 8/2019 | |
| EP | 3969100 B1 | 7/2023 | |
| JP | H0326620 A | 2/1991 | |
| JP | 3184145 B2 | 7/2001 | |
| JP | 2002517283 A | 6/2002 | |
| JP | 2002200178 A | 7/2002 | |
| JP | 2004065529 A | 3/2004 | |
| JP | 2007526798 A | 9/2007 | |
| JP | 2008067917 A | 3/2008 | |
| JP | 2008543429 A | 12/2008 | |
| JP | 2009512516 A | 3/2009 | |
| JP | 2011502586 A | 1/2011 | |
| JP | 2011504112 A | 2/2011 | |
| JP | 2012515060 A | 7/2012 | |
| JP | 2013508119 A | 3/2013 | |
| JP | 2014513562 A | 6/2014 | |
| JP | 2014514043 A | 6/2014 | |
| JP | 2016506255 A | 3/2016 | |
| JP | 6132856 B2 | 5/2017 | |
| JP | 2017104685 A | 6/2017 | |
| JP | 2017523868 A | 8/2017 | |
| JP | 2017525509 A | 9/2017 | |
| JP | 2018524113 A | 8/2018 | |
| KR | 101573840 B1 | 12/2015 | |
| RU | 2130326 C1 | 5/1999 | |
| RU | 2141851 C1 | 11/1999 | |
| RU | 2160127 C1 | 12/2000 | |
| RU | 2178319 C2 | 1/2002 | |
| RU | 2192897 C2 | 11/2002 | |
| RU | 2193441 C2 | 11/2002 | |
| RU | 2001102533 A | 11/2002 | |
| RU | 2226114 C1 | 3/2004 | |
| RU | 2258496 C2 | 8/2005 | |
| RU | 2361631 C2 | 7/2009 | |
| RU | 2368401 C1 | 9/2009 | |
| RU | 2387467 C1 | 4/2010 | |
| RU | 2396995 C2 | 8/2010 | |
| RU | 2397788 C2 | 8/2010 | |
| RU | 2445990 C1 | 3/2012 | |
| RU | 2471518 C2 | 1/2013 | |
| RU | 2475283 C2 | 2/2013 | |
| RU | 2661307 C1 | 7/2018 | |
| WO | 8100458 A1 | 2/1981 | |

(56) References Cited

FOREIGN PATENT DOCUMENTS

| | | | |
|---|---|---|---|
| WO | 9409808 | A1 | 5/1994 |
| WO | 9747357 | A1 | 12/1997 |
| WO | 9908749 | A1 | 2/1999 |
| WO | 0019912 | A1 | 4/2000 |
| WO | 0209808 | A1 | 2/2002 |
| WO | 0234331 | A2 | 5/2002 |
| WO | 02092165 | A1 | 11/2002 |
| WO | 03005887 | A2 | 1/2003 |
| WO | 03026735 | A2 | 4/2003 |
| WO | 03092795 | A1 | 11/2003 |
| WO | 2003094749 | A1 | 11/2003 |
| WO | 2004087116 | A2 | 10/2004 |
| WO | 2005002663 | A2 | 1/2005 |
| WO | 2005051306 | A2 | 6/2005 |
| WO | 2005065768 | A1 | 7/2005 |
| WO | 2005087307 | A2 | 9/2005 |
| WO | 2006026850 | A1 | 3/2006 |
| WO | 2006135751 | A2 | 12/2006 |
| WO | 2006138069 | A1 | 12/2006 |
| WO | 2007007057 | A1 | 1/2007 |
| WO | 2007007058 | A1 | 1/2007 |
| WO | 2007012114 | A1 | 2/2007 |
| WO | 2007047852 | A2 | 4/2007 |
| WO | 2007057508 | A2 | 5/2007 |
| WO | 2007081764 | A2 | 7/2007 |
| WO | 2007107831 | A2 | 9/2007 |
| WO | 2008075294 | A1 | 6/2008 |
| WO | 2008092785 | A1 | 8/2008 |
| WO | 2008070807 | A3 | 9/2008 |
| WO | 2008109862 | A2 | 9/2008 |
| WO | 2008121891 | A1 | 10/2008 |
| WO | 2009042217 | A1 | 4/2009 |
| WO | 2009111142 | A2 | 9/2009 |
| WO | 2010021977 | A1 | 2/2010 |
| WO | 2010055421 | A1 | 5/2010 |
| WO | 2010083308 | A1 | 7/2010 |
| WO | 2010114998 | A1 | 10/2010 |
| WO | 2010124128 | A1 | 10/2010 |
| WO | 2011005607 | A1 | 1/2011 |
| WO | 2011008459 | A2 | 1/2011 |
| WO | 2011136875 | A1 | 11/2011 |
| WO | 2012050200 | A1 | 4/2012 |
| WO | 2012075195 | A1 | 6/2012 |
| WO | 2012080964 | A1 | 6/2012 |
| WO | 2012094346 | A2 | 7/2012 |
| WO | 2012100260 | A2 | 7/2012 |
| WO | 2012103519 | A2 | 8/2012 |
| WO | 2012129574 | A2 | 9/2012 |
| WO | 2013049658 | A1 | 4/2013 |
| WO | 2013069004 | A1 | 5/2013 |
| WO | 2013071307 | A1 | 5/2013 |
| WO | 2013071309 | A1 | 5/2013 |
| WO | 2013117750 | A1 | 8/2013 |
| WO | 2013152124 | A1 | 10/2013 |
| WO | 2013179230 | A1 | 12/2013 |
| WO | 2013188965 | A1 | 12/2013 |
| WO | 2014005075 | A1 | 1/2014 |
| WO | 2014031142 | A1 | 2/2014 |
| WO | 2014089299 | A2 | 6/2014 |
| WO | 2014144785 | A1 | 9/2014 |
| WO | 2014149895 | A1 | 9/2014 |
| WO | 2014205356 | A2 | 12/2014 |
| WO | 2014209877 | A1 | 12/2014 |
| WO | 2015000800 | A1 | 1/2015 |
| WO | 2015048563 | A2 | 4/2015 |
| WO | 2015063127 | A1 | 5/2015 |
| WO | 2015106286 | A1 | 7/2015 |
| WO | 2015172894 | A1 | 11/2015 |
| WO | 2016005367 | A1 | 1/2016 |
| WO | 2016025913 | A1 | 2/2016 |
| WO | 2016029159 | A2 | 2/2016 |
| WO | 2016033369 | A1 | 3/2016 |
| WO | 2016033372 | A1 | 3/2016 |
| WO | 2016064761 | A1 | 4/2016 |
| WO | 2016110804 | A1 | 7/2016 |
| WO | 2016112398 | A1 | 7/2016 |
| WO | 2016172239 | A1 | 10/2016 |
| WO | 2017005661 | A1 | 1/2017 |
| WO | 2017011410 | A1 | 1/2017 |
| WO | 2017024276 | A1 | 2/2017 |
| WO | 2017035512 | A1 | 3/2017 |
| WO | 2017044904 | A1 | 3/2017 |
| WO | 2017058913 | A1 | 4/2017 |
| WO | 2017062508 | A1 | 4/2017 |
| WO | 2017117450 | A1 | 7/2017 |
| WO | 2017146659 | A1 | 8/2017 |
| WO | 2017188965 | A1 | 11/2017 |
| WO | 2018033591 | A2 | 2/2018 |
| WO | 2018039296 | A2 | 3/2018 |
| WO | 2018039458 | A1 | 3/2018 |
| WO | 2018063879 | A1 | 4/2018 |
| WO | 2018093765 | A1 | 5/2018 |
| WO | 2018106843 | A1 | 6/2018 |
| WO | 2018140531 | A1 | 8/2018 |
| WO | 2018148844 | A1 | 8/2018 |
| WO | 2018217791 | A1 | 11/2018 |
| WO | 2019211314 | A1 | 11/2019 |
| WO | 2020028088 | A1 | 2/2020 |
| WO | 2020041502 | A1 | 2/2020 |
| WO | 2020041633 | A1 | 2/2020 |
| WO | 2020236946 | A1 | 11/2020 |
| WO | 2022221442 | | 10/2022 |

OTHER PUBLICATIONS

International Search Report and Written Opinion issued in counterpart PCT Application No. PCT/US2016/049129 mailed Dec. 5, 2016, 13 pages.

International Search Report and Written Opinion issued in counterpart PCT Application No. PCT/US2017/015435, mailed May 8, 2017, 9 pages.

International Search Report and Written Opinion issued in counterpart PCT Application No. PCT/US2018/015098 mailed Mar. 12, 2018, 9 pages.

International Search Report and Written Opinion issued in counterpart PCT Application No. PCT/US2018/033942 mailed Aug. 31, 2018, 8 pages.

International Search Report and Written Opinion issued in counterpart PCT Application No. PCT/US2019/047551 mailed Nov. 21, 2019, 9 pages.

International Search Report and Written Opinion issued in counterpart PCT Application No. PCT/US2019/047777 mailed Nov. 14, 2019, 15 pages.

International Search Report and Written Opinion issued in counterpart PCT Application No. PCT/US2020/033830 mailed Oct. 14, 2020, 10 pages.

International Search Report and Written Opinion issued in counterpart PCT Application No. PCT/US2022/024673 mailed Jun. 28, 2022, 8 pages.

International Search Report issued in counterpart PCT Application No. PCT/US2012/020112 mailed Jul. 30, 2012, 4 pages.

International Search Report issued in counterpart PCT Application No. PCT/US2012/022257 mailed Sep. 3, 2012, 4 pages.

International Search Report issued in counterpart PCT Application No. PCT/US2012/030624 mailed Oct. 31, 2012, 3 pages.

International Search Report issued in counterpart PCT Application No. PCT/US2012/064874 mailed Mar. 19, 2013, 4 pages.

Ivanenko, Y. P. et al., "Temporal Components of the Motor Patterns Expressed by the Human Spinal Cord Reflect Foot Kinematics", Journal of Neurophysiology, (2003), vol. 90, No. 5, pp. 3555-3565.

Iyer, P. C. et al., "Characterization of stimulus response curves obtained with transcranial magnetic stimulation from bilateral tibialis anterior muscles post stroke", Neuroscience Letters, (2019), vol. 713, pp. 1-15.

Jaman, R., "A retrospective cross-sectional survey of lumbo-sacral recorded at the D.U.T. Chiropractic Day Clinic (1995-2005)", (2014). Durban University of Technology, Master's Degree in Technology dissertation. Retrieved from the Internet: <URL: https://doi.org/10.51415/10321/221>, 94 pages.

(56) References Cited

OTHER PUBLICATIONS

Japanese Patent Office Action in counterpart Japanese Patent Application No. 2017198155 mailed Aug. 20, 2019, 4 pages.
Japanese Patent Office Action in counterpart Japanese Patent Application No. 2017198155 mailed Sep. 11, 2018, 8 pages.
Japanese Patent Office Action in counterpart Japanese Patent Application No. 2018501208 mailed Jul. 13, 2020, 10 pages.
Japanese Patent Office Action in counterpart Japanese Patent Application No. 2018501208 mailed Mar. 22, 2021, 6 pages.
Japanese Patent Office Action in counterpart Japanese Patent Application No. 2019539960 mailed Feb. 17, 2023, 10 pages.
Japanese Patent Office Action in counterpart Japanese Patent Application No. 2019539960 mailed Nov. 29, 2021, 14 pages.
Japanese Patent Office Action in counterpart Japanese Patent Application No. 2019539960 mailed Sep. 26, 2022, 8 pages.
Japanese Patent Office Action in counterpart Japanese Patent Application No. 2021188658 mailed Nov. 21, 2022, 16 pages.
Japanese Patent Office Action in counterpart Japanese Patent Application No. 2021188658 mailed Sep. 4, 2023, 7 pages.
Japanese Patent Office Action in counterpart Japanese Patent Application No. 2021509772 mailed Jul. 18, 2023, 17 pages.
Japanese Patent Office Action in counterpart Japanese Patent Application No. 2021510130 mailed Augush 21, 2023, 20 pages.
Jarosiewicz, B. et al., "Supplementary Materials for Virtual typing by people with tetraplegia using a self-calibrating intracortical brain-computer interface", Science Translational Medicine, (2015), vol. 7, No. 313, pp. 1-26.
Jarosiewicz, B. et al., "Virtual typing by people with tetraplegia using a self-calibrating intracortical brain-computer interface", Science Translational Medicine, (2015), vol. 7, No. 313, pp. 1-11.
Jenny, A. B. et al., "Principles of Motor Organization of the Monkey Cervical Spinal Cord", The Journal of Neuroscience, (1983), vol. 3, No. 3, pp. 567-575.
Jilge, B. et al., "Initiating extension of the lower limbs in subjects with complete spinal cord injury by epidural lumbar cord stimulation", Experimental Brain Research, (2004), vol. 154, pp. 308-326.
Johnson, W. et al., "Application of a Rat Hindlimb Model: A Prediction of Force Spaces Reachable Through Stimulation of Nerve Fascicles", IEEE Transactions on Bio-Medical Engineering, (2011), vol. 58, No. 12, pp. 3328-3338.
Jones, D. R. et al., "Efficient Global Optimization of Expensive Black-Box Functions", Journal of Global Optimization, (1998), vol. 13, pp. 455-492.
Jones, K. et al., "Computer Simulation of the Responses of Human Motoneurons to Composite 1A EPSPS: Effects of Background Firing Rate", The Journal of Physiology, (1997), vol. 77, No. 1, pp. 405-420.
Jonic, S. et al., "Three machine learning techniques for automatic determination of rules to control locomotion", IEEE Transactions on Biomedical Engineering, (1999), vol. 46, No. 3, pp. 300-310.
Kakulas, A. B., "A Review of the Neuropathology of Human Spinal Cord Injury with Emphasis on Special Features", Proceedings of the Donald Munro Memorial Lecture at the American Paraplegia Society 44th Annual Conference, Las Vegas, NV, Spinal Cord, (1999), vol. 22, No. 2, pp. 119-124.
Kapetanakis, S. et al., "Cauda Equina Syndrome Due to Lumbar Disc Herniation: a Review of Literature", Folia Medica, (2017), vol. 59, No. 4, pp. 377-386.
Kim, W. S. et al., "Ultra-sensitive Flexible Pressure Sensor with Stamped Polyurethane Rubber", 2011 11th IEEE Conference on Nanotechnology, (2011), pp. 1607-1610.
Kim, Y. et al., "Electrical behavior of defibrillation and pacing electrodes", Proceedings of the IEEE, (2002), vol. 84, No. 3, pp. 446-456.
Kirazh, O. et al., "Anatomy of the spinal dorsal root entry zone: its clinical significance", Acta Neurochirurgica, (2014), vol. 156, pp. 2351-2358.
Kirkwood, P., "Neuronal Control of Locomotion: From Mollusc to Man", G.N. Orlovsky, T.G. Deliagina and S. Grillner. Oxford University Press, Oxford, 1999. ISBN 0198524056 (Hbk), 322 pp., Clinical Neurophysiology, vol. 111, (2000): 1524-1525.
Kitano, K. et al., "Spinal reflex in human lower leg muscles evolved by transcutaneous spinal cord stimulation", Journal of Neuroscience Methods, (2009), vol. 180, No. 1, pp. 111-115.
Kleinberg, R. et al., "Multi-armed bandits in metric spaces", In STOC, Computer and Automation Research Institute of the Hungarian Academy of Sciences, Budapest, Hungary, (2008), pp. 1-26.
Kocsis, L. et al., "Bandit Based Monte-Carlo Planning", European Conference on Machine Learning, Springer, Berlin, Heidelberg, (2006), pp. 282-293.
Kondo, T. et al., "Laser monitoring of chest wall displacement", European Respiratory Journal, (1997), vol. 10, No. 8, pp. 1865-1869.
Krassioukov, A. et al., "A Systematic Review of the Management of Autonomic Dysreflexia Following Spinal Cord Injury", Archives of Physical Medicine and Rehabilitation, (2009), vol. 90, No. 4, pp. 682-695.
Krassioukov, A. et al., "A Systematic Review of the Management of Orthostatic Hypotension Following Spinal Cord Injury", Archives of Physical Medicine and Rehabilitation, (2009), vol. 90, No. 5, pp. 876-885.
Krause, A. et al., "Contextual Gaussian Process Bandit Optimization", In Advances in Neural Information Processing Systems (NIPS), (2011), pp. 1-9.
Krause, A. et al., "Near-optimal Nonmyopic Value of Information in Graphical Models", In UAI, (2005), pp. 1-8.
Krause, A. et al., "Near-Optimal Sensor Placements in Gaussian Processes: Theory, Efficient Algorithms and Empirical Studies", Journal of Machine Learning Research, (2008), vol. 9, pp. 235-284.
Krenn, M. et al., "Selectivity of transcutaneous stimulation of lumbar posterior roots at different spinal levels in humans", Biomedical Technology, (2013), vol. 58 (Suppl. 1), pp. 1-2.
Kwakkel, G. et al., "Effects of Robot-assisted therapy on upper limb recovery after stroke: A Systematic Review", Neurorehabilitation and Neural Repair, (2008), vol. 22, No. 2, pp. 111-121.
Lacour, S. et al., "Flexible and stretchable micro-electrodes for in vitro and in vivo neural interfaces", Medical & Biological Engineering & Computing, (2010), vol. 48, pp. 945-954.
Lacour, S. et al., "Stretchable gold conductors on elastomeric substrates", Applied Physics Letters, (2003), vol. 82, No. 15, pp. 2404-2406.
Ladenbauer, J. et al., "Stimulation of the human lumbar spinal cord with implanted and surface electrodes: a computer simulation study", IEEE Transactions on Neural Systems and Rehabilitation Engineering, (2010), vol. 18, No. 6, pp. 637-645.
Lavrov, I. et al., "Epidural Stimulation Induced Modulation of Spinal Locomotor Networks in Adult Spinal Rats", Journal of Neuroscience, (2008), vol. 28, No. 23, pp. 6022-6029.
Levine, A. et al., "Identification of cellular node for motor control pathways", Nature Neuroscience, (2014), vol. 17, No. 4, pp. 586-593.
Liu, J. et al., "Stimulation of the parapyramidal region of the neonatal rat brain stem produces locomotor-like activity involving spinal 5-HT7 and 5-HT2A receptors", Journal of Neurophysiology, (2005), vol. 94, No. 2, pp. 1392-1404.
Lizotte, D. et al., "Automatic gait optimization with Gaussian process regression", In IJCAI, (2007), vol. 7, pp. 944-949.
Lovely, R. et al., "Effects of Training on the Recovery of Full-Weight-Bearing Stepping in the Adult Spinal Cat", Experimental Neurology, (1986), vol. 92, No. 2, pp. 421-435.
Lozano, A. et al., "Probing and Regulating Dysfunctional Circuits Using Deep Brain Stimulation", Neuron, (2013), vol. 77, No. 3, pp. 406-424.
Lu, D. et al., "Engaging cervical spinal cord networks to re-enable volitional control of hand function in tetraplegic patients", Neurorehabilitation and Neural Repair, (2016), vol. 30, No. 10, pp. 951-962.
McIntyre, C. et al., "Modeling the Excitability of Mammalian Nerve Fibers: Influence of Afterpotentials on the Recovery Cycle", Journal of Neurophysiology, (2002), vol. 87, No. 2, pp. 995-1006.

(56) References Cited

OTHER PUBLICATIONS

Meacham, K. W. et al., "A lithographically-patterned, elastic multi-electrode array for surface stimulation of the spinal cord", Biomed Microdevices, (2008), vol. 10, pp. 259-269.

Metzger, C. et al., "Flexible-foam-based capacitive sensor arrays for object detection at law cost", Applied Physics Letters, American Institute of Physics, (2008), vol. 92, No. 1, pp. 13506-1-13506-3.

Minassian, K. et al., "Human lumbar cord circuitries can be activated by extrinsic tonic input to generate locomotor-like activity", Human Movement Science, (2007), vol. 26, No. 2, pp. 275-295.

Minassian, K. et al., "Human Lumbar Cord Model of the Locomotor Central Pattern Generator", Second Congress International Society of Intraoperative Neurophysiology (ISIN), (2009), pp. 11-13.

Minassian, K. et al., "Mechanisms of rhythm generation of the human lumbar spinal cord in repose to tonic stimulation without and with step-related sensory feedback", Biomedical Technology, (2013), vol. 58, (Suppl. 1), pp. 1-3.

Minassian, K. et al., "Neuromodulation of lower limb motor control in restorative neurology", Clinical Neurology and Neurosurgery, (2012), vol. 114, No. 5, pp. 489-497.

Minassian, K. et al., "Neurophysiology of the human lumbar locomotor pattern generator", Proceedings 10th Vienna International Workshop on Functional Electrical Stimulation, Center for Medical Physics and Biomedical Engineering, (2010), pp. 259-261.

Minassian, K. et al., "Peripheral and Central Afferent Input to the Lumbar Cord", Biocybernetics and Biomedical Engineering, (2005), vol. 25, No. 3, pp. 11-29.

Minassian, K. et al., "Posterior root-muscle reflex", Second Congress International Society of Intraoperative Neurophysiology (ISIN), Dubrovnik, Croatia, (2009), pp. 77-80.

Minassian, K. et al., "Posterior root-muscle reflexes elicited by transcutaneous stimulation of the human lumbosacral cord", Muscle and Nerve, (2007), vol. 35, No. 3, pp. 327-336.

Minassian, K. et al., "Stepping-like movements in humans with complete spinal cord injury induced by epidural stimulation of the lumbar cord: electromyographic study of compound muscle action potentials", Spinal Cord, (2004), vol. 42, No. 7, pp. 401-416.

Minassian, K. et al., "Transcutaneous spinal cord stimulation", International Society for Restoration Neurology, (2011), pp. 1-6.

Minassian, K. et al., "Transcutaneous stimulation of the human lumbar spinal cord: Facilitating locomotor output in spinal cord injury", Society for Neuroscience, Conference Proceedings, Neuroscience 2010, San Diego, CA, Abstract Viewer/ Itinerary Planner No. 286.19, Abstract & Poster attached, (2010), 2 pages.

Minev, I. R. et al., "Electronic dura mater for long-term multimodal neural interfaces—with supplementary materials", Science, (2015), vol. 347, No. 6218, pp. 1-64.

Minev, I. R. et al., "Evaluation of an Elastomer Based Gold Microelectrode Array for Neural Recording Applications", Proceedings of the 5th International IEEE/EMBS Conference on Neural Engineering, Cancun, Mexico, (2011), pp. 482-485.

Minev, I. R. et al., "High sensitivity recording of afferent nerve activity using ultra-compliant microchannel electrodes: an acute in vivo validation", Journal of Neural Engineering, (2012), vol. 9, No. 2, pp. 1-7.

Minoux, M., "Accelerated greedy algorithms for maximizing submodular set functions", Optimization Techniques, LNCS, (1978), pp. 234-243.

Moraud, E. et al., "Mechanisms Underlying the Neuromodulation of Spinal Circuits for Correcting Gait and Balance Deficits after Spinal Cord Injury", Neuron, (2016), vol. 89, No. 4, pp. 814-828.

Murg, M. et al., "Epidural electric stimulation of posterior structures of the human lumbar spinal cord: 1. Muscle twitches—a functional method to define the site of stimulation", Spinal Cord, (2000), vol. 38, No. 7, pp. 394-402.

Musienko, P. et al., "Combinatory Electrical and Pharmacological Neuroprosthetic Interfaces to Regain Motor Function After Spinal Cord Injury", IEEE Transactions on Biomedical Engineering, (2009), vol. 56, No. 11, pp. 2707-2711.

Musienko, P. et al., "Controlling specific locomotor behaviors through multidimensional monoaminergic modulation of spinal circuitries", The Journal of Neuroscience, (2011), vol. 31, No. 25, pp. 9264-9278.

Musienko, P. et al., "Multi-system neurorehabilitative strategies to restore motor functions following severe spinal cord injury", Experimental Neurology, (2012), vol. 235, No. 1, pp. 100-109.

Musselman, K. et al., "Spinal Cord Injury Functional Ambulation Profile: A New Measure of Walking Ability", Neurorehabilitation and Neural Repair, (2011), vol. 25, No. 3, pp. 285-293.

Nandra, M. et al., "Microelectrode Implants for Spinal Cord Stimulation in Rats", Doctor of Philosophy Thesis, California Institute of Technology, (2014), pp. 1-104.

Nandra, M. S. et al., "A parylene-based microelectrode array implant for spinal cord stimulation in rats", Conference Proceedings IEEE Engineering in Medicine and Biology Society, (2011), pp. 1007-1010.

Nandra, M. S. et al., "A wireless microelectrode implant for spinal cord stimulation and recording in rats", Presentation Abstract, (2013), pp. 1-104.

Needle, A. R. et al., "Brain Regulation of muscle tone in healthy and functionally unstable ankles", Journal of Sport Rehabilitation, (2013), vol. 22, No. 3, pp. 202-211.

Nessler, J. et al., "A Robotic Device for Studying Rodent Locomotion After Spinal Cord Injury", IEEE Transactions on Neural Systems and Rehabilitation Engineering, (2005), vol. 13, No. 4, pp. 497-506.

Niu, T. et al., "A Proof-of-Concept Study of Transcutaneous Magnetic Spinal Cord Stimulation for Neurogenic Bladder", Scientific Reports, (2018), vol. 8, No. 1, pp. 1-12.

Notice of Allowance in U.S. Appl. No. 14/355,812, mailed Apr. 13, 2016, 7 pages.

Notice of Allowance in U.S. Appl. No. 14/775,618, mailed Jan. 18, 2018, 11 pages.

Notice of Allowance in U.S. Appl. No. 15/025,201, mailed Aug. 1, 2018, 10 pages.

Notice of Allowance in U.S. Appl. No. 15/208,529, mailed Jun. 17, 2020, 7 pages.

Notice of Allowance in U.S. Appl. No. 15/344,381, mailed Apr. 27, 2021, 12 pages.

Notice of Allowance in U.S. Appl. No. 15/505,053, mailed Jun. 4, 2020, 8 pages.

Notice of Allowance in U.S. Appl. No. 15/505,053, mailed Jun. 4, 2020, 9 pages.

Notice of Allowance in U.S. Appl. No. 15/506,696, mailed May 4, 2020, 8 pages.

Graz, I. et al., "Silicone substrate with in situ strain relief for stretchable thin-film transistors", Applied Physics Letters, AIP, American Institute of Physics, (2011), vol. 98, No. 12, pp. 124101-1-124101-3.

Guyatt, G. et al., "The 6-minute walk: a new measure of exercise capacity in patients with chronic heart failure", Canadian Medical Association Journal, (1985), vol. 132, No. 8, pp. 919-923.

Hagglund, M. et al., "Activation of groups of excitatory neurons in the mammalian spinal cord or hindbrain evokes locomotion", Nature Neuroscience, (2010), vol. 13, No. 2, pp. 246-252.

Harkema, S. et al., "Effect of Epidural stimulation of the lumbosacral spinal cord on voluntary movement, standing, and assisted stepping after motor complete paraplegia: a case study", Lancet, (2011), vol. 377, No. 9781, pp. 1938-1947.

Harkema, S. et al., "Human Lumbosacral Spinal Cord Interprets Loading During Stepping", Journal of Neurophysiology, (1997), vol. 77, No. 2, pp. 797-811.

Harkema, S. et al., "Normalization of Blood Pressure with Spinal Cord Epidural Stimulation After Severe Spinal Cord Injury", Frontiers in Human Neuroscience, (2018), vol. 12, pp. 1-11.

Harrison, P. et al., "Individual Excitatory Post-Synaptic Potentials Due to Muscle Spindle la Afferents in Cat Triceps Surae Motoneurones", The Journal Physiology, (1981), vol. 312, No. 1, pp. 455-470.

Hashtrudi-Zaad, K. et al., "On the Use of Local Force Feedback for Transparent Teleoperation", Proceedings of the 1999 IEEE International Conference on Robotics and Automation, (1999), vol. 3, pp. 1863-1869.

(56) References Cited

OTHER PUBLICATIONS

Health Journalism Glossary: Bidirectional, Definition [online], Association of Health Care Journalists, 2024. Retrieved from the Internet: <URL:https://healthjournalism.org/glossary-terms/bidirectional/>, 3 pages.
Hennig, P. et al., "Entropy search for information-efficient global optimization", Journal of Machine Learning Research (JMLR), (2012), vol. 13, No. 1, pp. 1809-1837.
Herman, R. et al., "Spinal cord stimulation facilitates functional walking in a chronic, incomplete spinal cord injured", Spinal Cord, (2002), vol. 40, No. 2, pp. 65-68.
Hidler, J. et al., "ZeroG: Overground gait and balance training system", Journal of Rehabilitation Research & Development, (2011), vol. 48, No. 4, pp. 287-298.
Hines, M. et al., "The Neuron Simulation Environment", Neural Computation, (1997), vol. 9, No. 6, pp. 1179-1209.
Hofstoetter, U. S. et al., "Modification of spasticity by transcutaneous spinal cord stimulation in individuals with incomplete spinal cord injury", The Journal of Spinal Cord Medicine, (2014), vol. 37, No. 2, pp. 202-211.
Hofstoetter, U.S. et al., "Effects of transcutaneous spinal cord stimulation on voluntary locomotor activity in an incomplete spinal cord injured individual", Biomedical Technology, (2013), vol. 58 (Suppl. 1), pp. 1-3.
Hofstoetter, U.S. et al., "Modification of Reflex Responses to Lumbar Posterior Root Stimulation by Motor Tasks in Healthy Subjects", Artificial Organs, (2008), vol. 32, No. 8, pp. 644-648.
Hofstotter, U.S. et al., "Model of spinal cord reflex circuits in humans: Stimulation frequency-dependence of segmental activities and their interactions", Second Congress International Society of Intraoperative Neurophysiology (ISIN), Dubrovnik, Croatia, (2009), pp. 1-149.
Hohenschurz-Schmidt, D. J. et al., "Linking Pain Sensation to the Autonomic Nervous System: The Role of the Anterior Cingulate and Periaqueductal Gray Resting-State Networks", Front Neuroscience, (2020), vol. 14, No. 147, pp. 1-15.
Hovey, C. et al., "The New Guide to Magnet Stimulation", The Magstim Company Ltd., (2006), pp. 1-45.
Hung, C. C. et al., "Transparent microprobe array fabricated by MEMS hot embossing technology for photodynamic therapy application", IEICE Electronics Express, (2010), vol. 7, No. 9, pp. 569-576.
Ichiyama, R. M. et al., "Hindlimb stepping movements in complete spinal rats induced by epidural spinal cord stimulation", Neuroscience Letters, (2005), vol. 383, No. 3, pp. 339-344.
International Preliminary Report on Patentability issued in counterpart PCT Application No. PCT/US2012/020112 mailed Jul. 10, 2013, 5 pages.
International Preliminary Report on Patentability issued in counterpart PCT Application No. PCT/US2012/064878 mailed May 22, 2014, 8 pages.
International Preliminary Report on Patentability issued in counterpart PCT Application No. PCT/US2014/029340 mailed Sep. 24, 2015, 8 pages.
International Preliminary Report on Patentability issued in counterpart PCT Application No. PCT/US2014/057886, mailed Apr. 7, 2016, 6 pages.
International Preliminary Report on Patentability issued in counterpart PCT Application No. PCT/US2015/046378 mailed Feb. 21, 2017, 5 pages.
International Preliminary Report on Patentability issued in counterpart PCT Application No. PCT/US2015/047268 mailed Feb. 28, 2017, 12 pages.
International Preliminary Report on Patentability issued in counterpart PCT Application No. PCT/US2015/047272 mailed Feb. 28, 2017, 8 pages.
International Preliminary Report on Patentability issued in counterpart PCT Application No. PCT/US2016/041802 mailed Jan. 25, 2018, 12 pages.

International Preliminary Report on Patentability issued in counterpart PCT Application No. PCT/US2016/045898 mailed Feb. 15, 2018, 8 pages.
International Preliminary Report on Patentability issued in counterpart PCT Application No. PCT/US2016/049129 mailed Mar. 8, 2018, 9 pages.
International Preliminary Report on Patentability issued in counterpart PCT Application No. PCT/US2018/015098 mailed Jul. 30, 2019, 7 pages.
International Preliminary Report on Patentability issued in counterpart PCT Application No. PCT/US2018/033942 mailed Nov. 26, 2019, 6 pages.
International Preliminary Report on Patentability issued in counterpart PCT Application No. PCT/US2019/047551 mailed Feb. 23, 2021, 7 pages.
International Preliminary Report on Patentability issued in counterpart PCT Application No. PCT/US2019/047777 mailed Feb. 23, 2021, 12 pages.
International Preliminary Report on Patentability issued in counterpart PCT Application No. PCT/US2020/033830 mailed Dec. 2, 2021, 7 pages.
International Search Report and Written Opinion issued in counterpart PCT Application No. EP2020/063564, mailed Sep. 11, 2020, 12 pages.
International Search Report and Written Opinion issued in counterpart PCT Application No. PCT/EP2017/083478, mailed May 3, 2018, 10 pages.
International Search Report and Written Opinion issued in counterpart PCT Application No. PCT/EP2018/082939, mailed Feb. 14, 2019, 11 pages.
International Search Report and Written Opinion issued in counterpart PCT Application No. PCT/EP2018/082942, mailed Feb. 14, 2019, 11 pages.
International Search Report and Written Opinion issued in counterpart PCT Application No. PCT/EP2020/053381, mailed May 12, 2020, 8 pages.
International Search Report and Written Opinion issued in counterpart PCT Application No. PCT/EP2020/063563, mailed Jul. 30, 2020, 14 pages.
International Search Report and Written Opinion issued in counterpart PCT Application No. PCT/US2012/064878 mailed Mar. 19, 2013, 11 pages.
International Search Report and Written Opinion issued in counterpart PCT Application No. PCT/US2014/029340 mailed Aug. 6, 2014, 11 pages.
International Search Report and Written Opinion issued in counterpart PCT Application No. PCT/US2014/057886 mailed Dec. 24, 2014, 6 pages.
International Search Report and Written Opinion issued in counterpart PCT Application No. PCT/US2015/011263 mailed May 19, 2015, 12 pages.
International Search Report and Written Opinion issued in counterpart PCT Application No. PCT/US2015/046378 mailed Dec. 1, 2015, 5 pages.
International Search Report and Written Opinion issued in counterpart PCT Application No. PCT/US2015/047268 mailed Dec. 8, 2015, 17 pages.
International Search Report and Written Opinion issued in counterpart PCT Application No. PCT/US2015/047272 mailed Dec. 3, 2015, 11 pages.
International Search Report and Written Opinion issued in counterpart PCT Application No. PCT/US2016/041802 mailed Sep. 12, 2016, 17 pages.
Park, K. J. et al., "Continuous "Over and Over" Suture for Tricuspid Ring Annuloplasty", Korean Journal of Thoracic and Cardiovascular Surgery, (2012), vol. 45, No. 1, pp. 19-23.
Peachpit, "Working with Basic Shapes in Adobe Illustrator CC (2014 release)," PeachPit, Nov. 3, 2014 [retrieved on Feb. 6, 2024]. Retrieved from the Internet: <URL: https://www.peachpit.com/articles/article.aspx?p=2253413&seqNum=3>.
Pearson, K. G., "Generating the walking gait: role of sensory feedback", Progress in Brain Research, (2004), vol. 143, Chapter 12, pp. 123-129.

(56)
References Cited

OTHER PUBLICATIONS

Pellinen, D.S. et al., "Multifunctional Flexible Parylene-Based Intracortical Microelectrodes", Proceedings of the 2005 IEEE: Engineering in Medicine and Biology 27th Annual Conference, (2005), pp. 5272-5275.

Pflug, H. et al., "Parallel Resonant Inductive Wireless Power Transfer", IEEE, Proceedings of Wireless Power Week 2019, London, United Kingdom (2019), pp. 182-187.

Phillips, A. A. et al., "Contemporary Cardiovascular Concerns after Spinal Cord Injury: Mechanisms, Maladaptations, and Management", Journal of Neurotrama, (2015), vol. 32, No. 24, pp. 1927-1942.

Phillips, A. et al., "Perturbed and spontaneous regional cerebral blood flow responses to changes in blood pressure secondary high-level spinal cord injury: the effect of midodrine", Journal of Applied Physiology, (2014), vol. 116, No. 6, pp. 645-653.

Phillips, A. et al., "Regional neurovascular coupling and cognitive performance in those with low blood pressure secondary to high-level spinal cord injury: improved by alpha-1 agonist midodrine hydrochloride", Journal of Cerebral Blood Flow & Metabolism, (2014), vol. 34, No. 5, pp. 794-801.

Pratt, G. et al., "Stiffness Isn't Everything", Proceedings of the Fourth International Symposium on Experimental Robotics, (1995), pp. 1-6.

Pratt, J. et al., "Series elastic actuators for high fidelity force control", Industrial Robot: An International Journal, (2002), vol. 29, No. 3, pp. 234-241.

Prochazka, A. et al., "Ensemble firing of muscle afferents recorded during normal locomotion in cats", The Journal of Physiology, (1998), vol. 507, No. 1, pp. 293-304.

Prochazka, A. et al., "Models of ensemble firing of muscle spindle afferents recorded during normal locomotion in cats", The Journal of Physiology, (1998), vol. 507, No. 1, pp. 277-291.

Pudo, D. et al., "Estimating Intensity Fluctuations in High Repetition Rate Pulse Trains Generated Using the Temporal Talbot Effect", IEEE Photonics Technology Letters, (2006), vol. 18, No. 5, pp. 658-660.

Purves, D. et al., "Autonomic Regulation of the Bladder", Neuroscience, 2nd edition, Chapter Twenty-One, Sunderland, (MA), (2022), pp. 1-5.

Rasmussen, C. E. et al., "Gaussian Processes for Machine Learning (GPML) Toolbox", The Journal of Machine Learning Research, (2010), vol. 11, pp. 3011-3015.

Rasmussen, C. E. et al., "Gaussian Processes for Machine Learning", The MIT Press, Cambridge, Massachusetts, (2006), pp. 1-266.

Rasmussen, C. E., "Gaussian Processes in Machine Learning", LNAI, (2003), vol. 3176, pp. 63-71.

Rattay, F. et al., "Epidural electrical stimulation of posterior structures of the human lumbosacral cord: 2. Quantitative analysis by computer modeling", Spinal Cord, (2000), vol. 38, No. 8, pp. 473-489.

Reinkensmeyer, D. et al., "Tools for understanding and optimizing robotic gait training", Journal of Rehabilitation Research & Development, (2006), vol. 43, No. 5, pp. 657-670.

Rejc, E. et al., "Effects of Lumbosacral Spinal Cord Epidural Stimulation for Standing after Chronic Complete Paralysis in Humans", PLoS One, (2015), vol. 10, No. 7, pp. 1-20.

Restriction Requirement in U.S. Appl. No. 16/479,201, mailed Apr. 19, 2022, 9 pages.

Restriction Requirement in U.S. Appl. No. 17/270,402, mailed Dec. 1, 2022, 25 pages.

Robbins, H., "Some Aspects of the Sequential Design of Experiments", Bulletin of the American Mathematical Society, (1952), vol. 58, pp. 527-535.

Robinson, A. et al., "Hybrid stretchable circuits on silicone substrate", Journal of Applied Physics, (2014), vol. 115, No. 14, pp. 143511-1-143511-5.

Rodger, D. C. et al., "High Density Flexible Parylene-Based Multielectrode Arrays for Retinal and Spinal Cord Stimulation", Proc. of the 14th International Conference on Solid-State Sensors, Actuators and Microsystems, (2007), pp. 1385-1888.

Rosenzweig, E. et al., "Extensive Spontaneous Plasticity of Corticospinal Projections After Primate Spinal Cord Injury—with supplementary materials", Nature Neuroscience, (2010), vol. 13, No. 12, pp. 1505-1510.

Roy, F. D. et al., "Effect of percutaneous stimulation at different spinal levels on the activation of sensory and motor roots", Experimental Brain Research, (2012), vol. 223, pp. 281-289.

Rubinstein et al., "Current Density Profiles of Surface Mounted and Recessed Electrodes for Neural Prostheses", Biomedical Engineering, IEEE Transactions on BME, (1987), vol. 34, No. 11, pp. 864-875.

Ryzhov, I. O. et al., "The knowledge gradient algorithm for a general class of online learning problems", Operations Research, (2012), vol. 60, No. 1, pp. 1-47.

Sayenko, D. et al., "Neuromodulation of evoked muscle potentials induced by epidural spinal-cord stimulation in paralyzed individuals", Journal of Neurophysiology, (2014), vol. 111, No. 5, pp. 1088-1099.

Sayenko, D. G. et al., "Spinal segment-specific transcutaneous stimulation differentially shapes activation pattern among motor pools in humans", Journal of Applied Physiology, (2015), vol. 118, No. 11, pp. 1364-1374.

Schmidlin, E. et al., "Behavioral Assessment of Manual Dexterity in Non-Human Primates", Journal of Visualized Experiments, (2011), vol. 57, No. e3258, pp. 1-11.

Seifert, H. M. et al., "Restoration of Movement Using Functional Electrical Stimulation and Bayes' Theorem", The Journal of Neuroscience, (2002), vol. 22, No. 21, pp. 9465-9474.

Shafik, A. et al., "Extrapelvic cavernous nerve stimulation in erectile dysfunction. Human Study", Andrologia, (1996), vol. 28, No. 3, pp. 151-156.

Shafik, A. et al., "Magnetic stimulation of the cavernous nerve for the treatment of erectile dysfunction in humans", International Journal of Impotence Research, (2000), vol. 12, No. 3, pp. 137-141.

Shamir, R. et al., "Machine learning approach to optimizing combined stimulation and medication therapies for Parkinson's disease—with supplementary materials", Brain Stimulation, (2015), vol. 8, No. 6, pp. 1025-1032.

Sharpe, A. et al., "Upper-limb muscles responses to epidural, subdural and intraspinal stimulation of the cervical spinal cord", Journal of Neural Engineering, (2014), vol. 11, No. 1, pp. 1-16.

Sherman, J. et al., "Measurements of the normal cervical spinal cord on MR Imaging", American Journal of Neuroradiology, (1990), vol. 11, No. 2, pp. 369-372.

Srinivas, N. et al., "Gaussian process optimization in the bandit setting: No regret and experimental design", In Proceedings of the 27th International Conference on Machine Learning, (2010), pp. 1-17.

Steward, O. et al., "False Resurrections: Distinguishing Regenerated from Spared Axons in the Injured Central Nervous System", The Journal of Comparative Neurology, (2003), vol. 459, No. 1, pp. 1-8.

Stienen, A. et al., "Analysis of reflex modulation with a biologically realistic neural network", Journal of Computer Neuroscience, (2007), vol. 23, pp. 333-348.

Sun, F. et al., "Sustained axon regeneration induced by co-deletion of PTEN and SOCS3—with supplementary material", Nature, (2011), vol. 480, No. 7377, pp. 372-375.

Suzuki, T. et al., "A 3D flexible parylene probe array for multichannel neural recording", IEEE Neural Engineering, (2003), pp. 154-156.

Szava, Z. et al., "Transcutaneous electrical spinal cord stimulation: Biophysics of a new rehabilitation method after spinal cord injury", VDM Publishing, Saarbrucken, Germany, (2011), pp. 1-95.

Takeoka, A. et al., "Muscle Spindle Feedback Directs Locomotor Recovery and Circuit Reorganization after Spinal Cord Injury", Cell, (2014), vol. 159, No. 7, pp. 1626-1639.

Takeuchi, S. et al., "3D flexible multichannel neural probe array", Journal of Micromechanics and Microengineering, (2004), vol. 14, No. 1, pp. 104-107.

(56)        References Cited

OTHER PUBLICATIONS

Tanabe, S. et al., "Effects of transcutaneous electrical stimulation combined with locomotion-like movement in the treatment of post-stroke gait disorder: a single-case study", (2008), vol. 30, No. 5, pp. 411-416.

Temel, Y. et al., "Case Report—Deep brain stimulation of the thalamus can influence penile erection", International Journal of Impotence Research, (2004), vol. 16, No. 1, pp. 91-94.

Tenne, Y. et al., "Computational Intelligence in Expensive Optimization Problems", Adaptation, Learning, and Optimization, Springer, Berlin Heidelberg, (2010), vol. 2, pp. 131-162.

The State Intellectual Property Office of People's Republic of China Office Action in counterpart Chinese Patent Application No. 201610987062.5 mailed Sep. 30, 2018, 20 pages.

Office Action in U.S. Appl. No. 17/399,780, mailed Jun. 12, 2025, 12 pages.

The State Intellectual Property Office of People's Republic of China Office Action in counterpart Chinese Patent Application No. 201680058067.8 mailed Jan. 6, 2021, 1 page.

The State Intellectual Property Office of People's Republic of China Office Action in counterpart Chinese Patent Application No. 201780080305.X mailed Aug. 31, 2023, 9 pages.

Timoszyk, W. et al., "Hindlimb loading determines stepping quantity and quality following spinal cord transection", Brain Research, (2005), vol. 1050, No. 1-2, pp. 180-189.

Troni, W. et al., "A methodological reappraisal of non invasive high voltage electrical stimulation of lumbosacral nerve roots", Clinical Neurophysiology, (2011), vol. 122, No. 10, pp. 2071-2080.

Tungjitkusolmun, S. et al., "Finite element analyses of uniform current density electrodes for radio-frequency cardiac ablation", IEEE Transactions on Biomedical Engineering, (2000), vol. 47, No. 1, pp. 32-40.

U.S. Appl. No. 15/821,076, filed Nov. 22, 2017, 52 pages.

U.S. Appl. No. 16/153,472, filed Oct. 5, 2018, 51 pages.

U.S. Appl. No. 16/189,655, filed Nov. 13, 2018, 37 pages.

U.S. Appl. No. 61/802,034, filed Mar. 15, 2013, 29 pages.

U.S. Appl. No. 62/171,427, filed Jun. 5, 2015, 55 pages.

U.S. Appl. No. 62/171,436, filed Jun. 5, 2015, 44 pages.

U.S. Appl. No. 62/201,973, filed Aug. 6, 2015, 54 pages.

Valchinov, E. S. et al., "An active electrode for biopotential recording from small localized bio-sources", BioMedical Engineering OnLine, (2004), vol. 3, No. 25, pp. 1-14.

Vallery, H. et al., "Compliant Actuation of Rehabilitation Robots", IEEE Robotics & Automation Magazine, (2008), vol. 15, No. 3, pp. 60-69.

Van Den Brand, R. et al., "Restoring Voluntary Control of Locomotion after Paralyzing Spinal Cord Injury", Science Magazine, (2012), vol. 336, No. 6085, pp. 1182-1185.

Wan, D. et al., "Life-threatening outcomes associated with autonomic dysreflexia: A clinical review", Journal of Spinal Cord Medicine, (2014), vol. 37, No. 1, pp. 2-10.

Wang, J. M. et al., "Gaussian process dynamical models for human motion", IEEE Transactions on Pattern Analysis and Machine Intelligence, (2007), vol. 30, No. 2, pp. 283-298.

Wang, T. et al., "Incidence of C5 nerve root palsy after cervical surgery—A meta-analysis for decade", Medicine, (2017), vol. 96, No. 45, pp. 1-14.

Ward, A. R. et al., "Sensory, motor, and pain thresholds for stimulation with medium frequency alternating current", Archives of Physical Medicine and Rehabilitation, (1998), vol. 79, No. 3, pp. 273-278.

Ward, A. R., "Electrical Stimulation Using Kilohertz-Frequency Alternating Current", Physical Therapy, (2009), vol. 89, No. 2, pp. 181-190.

Wei, P. et al., "Stretchable microelectrode array using room-temperature liquid alloy interconnects", Journal of Micromechanics and Microengineering, (2011), vol. 21, No. 054015, pp. 1-8.

Wenger, N. et al., "Closed-loop neuromodulation of spinal sensorimotor circuits controls refined locomotion after complete spinal cord injury", Science Translational Medicine, (2014), vol. 6, Issue 255, pp. 1-11.

Wenger, N. et al., "Spatiotemporal neuromodulation therapies engaging muscle synergies improve motor control after spinal cord injury—with supplementary material", Natural Medicine, (2016), vol. 22, No. 2, pp. 138-145.

Wenger, N. et al., "Supplementary Materials for Closed-loop neuromodulation of spinal sensorimotor circuits controls refined locomotion after complete spinal cord injury", Science Translational Medicine, (2014), vol. 6, Iss. 255, pp. 1-14.

Wernig, A. et al., "Laufband locomotion with body weight support improved walking in persons with severe spinal cord injuries", International Medical Society of Paraplegia, (1992), vol. 30, No. 4, pp. 229-238.

Wernig, A., "Ineffectiveness of Automated Locomotor Training", Archives of Physical Medicine and Rehabilitation, (2005), vol. 86, No. 12, pp. 2385-2386.

Wessels, M. et al., "Body Weight-Supported Gait Training for Restoration of Walking in People With an Incomplete Spinal Cord Injury: A Systematic Review", Journal of Rehabilitation Medicine, (2010), vol. 42, No. 6, pp. 513-519.

Widmer, C. et al., "Inferring latent task structure for multitask learning by multiple kernel learning", BMC Bioinformatics, (2010), vol. 11, pp. 1-8.

Wiley, J. D. et al., "Analysis and Control of the Current Distribution under Circular Dispersive Electrodes", Biomedical Engineering, IEEE Transactions on BME, (1982), vol. 29, No. 5, pp. 381-385.

Winter, D. et al., "An integrated EMG/biomechanical model of upper body balance and posture during human gait", Progress in Brain Research, (1993), vol. 97, Ch. 32, pp. 359-367.

Wirz, M. et al., "Effectiveness of automated locomotor training in patients with chronic incomplete spinal cord injury: a multicenter trial", Archives of Physical Medicine and Rehabilitation, (2005), vol. 86, No. 4, pp. 672-680.

Yakovenko, S. et al., "Spatiotemporal Activation of Lumbosacral Motoneurons in the Locomotor Step Cycle", Journal of Neurophysiology, (2002), vol. 87, No. 3, pp. 1542-1553.

YouTube video entitled: "How to Round Corners in Illustrator," uploaded Sep. 6, 2017 by user "Mohamed Achraf" [retrieved on Jul. 7, 2022]. Retrieved from the Internet: <URL:https://www.youtube.com/watch?v=q8Cyd0sqY6A>, 3 pages.

Zhang, T. C. et al., "Mechanisms and models of spinal cord stimulation for the treatment of neuropathic pain", Brain Research, (2014), vol. 1569, pp. 19-31.

Zorner, B. et al., "Profiling locomotor recovery: comprehensive quantification of impairments after CNS damage in rodents", Nature Methods, (2010), vol. 7, No. 9, pp. 701-708.

Abernethy, J. et al., "Competing in the dark: An efficient algorithm for bandit linear optimization", Conference on Learning Theory, (2009), No. 110, pp. 1-13.

Ada, L. et al., "Mechanically assisted walking with body weight support results in more independent walking than assisted overground walking in non-ambulatory patients early after stroke: a systematic review", Journal of Physiotherapy, (2010), vol. 56, No. 3, pp. 153-161.

Alto, L. et al., "Chemotropic guidance facilitates axonal regeneration and synapse formation after spinal cord injury", Nature Neuroscience, (2009), vol. 12, No. 9, pp. 1106-1113.

Anderson, K., "Targeting recovery: priorities of the spinal cord-injured population", Journal of Neurotrauma, (2004), vol. 21, No. 10, pp. 1371-1383.

Andersson, K. E. et al., "CNS Involvement in Overactive Bladder—Pathophysiology and Opportunities for Pharmacological Intervention", Drugs, (2003), vol. 63, No. 23, pp. 2595-2611.

Angeli, C. et al., "Altering spinal cord excitability enables voluntary movements after chronic complete paralysis in humans", Brain: A Journal of Neurology, (2014), vol. 137, No. 5, pp. 1394-1409.

Anonymous, "Re: Round corners (fillet) in Illustrator CS6", in: Stack Exchange [online], Graphic Design, Jan. 22, 2018; 17:52 [retrieved on Feb. 6, 2024]. Retrieved from the Internet: <URL:https://

(56) References Cited

OTHER PUBLICATIONS graphicdesign.stackexchange.com/questions/104349/round-corners-fillet-in-illustrator-cs6>, 10 pages.

Anonymous, Lumbar Decompression Surgery: When it's used, Datasheet [online], National Health Service, 2022. Retrieved from the Internet: <URL:https://www.nhs.uk/conditions/lumbar-decompression-surgery/why-its-done/#:-:text=Cauda%equina%20syndrome%20a.is%20severe%20or%20getting%20worse, 2 pages.

Anonymous, Vital Signs, Datasheet [online], Cleveland Clinic [retrieved on Nov. 22, 2021]. Retrieved from the Internet: <URL:https://my.clevelandclinic.org/health/articles/10881-vital-signs, 19 pages.

Ateh, D. D. et al., "Polypyrrole-based conducting polymers and interactions with biological tissues", Journal of the Royal Society Interface, (2006), vol. 3, No. 11, pp. 741-752.

Auer, P. et al., "Finite-time analysis of the multiarmed bandit problem", Machine Learning, (2002), vol. 47, No. 2, pp. 235-256.

Auer, P., "Using confidence bounds for exploitation-exploration trade-offs", Journal of Machine Learning Research, (2002), vol. 3, pp. 397-422.

Australian Examination Report No. 1 in counterpart Australian Patent Application No. 2012334926 mailed Jul. 11, 2016, 3 pages.

Australian Examination Report No. 1 in counterpart Australian Patent Application No. 2014228794 mailed May 11, 2018, 4 pages.

Australian Examination Report No. 1 in counterpart Australian Patent Application No. 2014324660 mailed Jan. 11, 2019, 5 pages.

Australian Examination Report No. 1 in counterpart Australian Patent Application No. 2015305237 mailed Jun. 14, 2019, 4 pages.

Australian Examination Report No. 1 in counterpart Australian Patent Application No. 2015308779 mailed Jul. 18, 2019, 3 pages.

Australian Examination Report No. 1 in counterpart Australian Patent Application No. 2017202237 mailed Apr. 6, 2018, 3 pages.

Australian Examination Report No. 1 in counterpart Australian Patent Application No. 2017203132 mailed Oct. 13, 2017, 4 pages.

Australian Examination Report No. 1 in counterpart Australian Patent Application No. 2017221868 mailed Jan. 23, 2018, 3 pages.

Australian Examination Report No. 1 in counterpart Australian Patent Application No. 2019206059 mailed Jan. 6, 2020, 4 pages.

Australian Examination Report No. 1 in counterpart Australian Patent Application No. 2020200152 mailed Dec. 21, 2020, 4 pages.

Australian Examination Report No. 2 in counterpart Australian Patent Application No. 2014324660 mailed Nov. 7, 2019, 4 pages.

Australian Examination Report No. 2 in counterpart Australian Patent Application No. 2015305237 mailed Apr. 17, 2020, 4 pages.

Australian Examination Report No. 2 in counterpart Australian Patent Application No. 2015308779 mailed May 20, 2020, 3 pages.

Australian Examination Report No. 3 in counterpart Australian Patent Application No. 2014324660 mailed Jan. 6, 2020, 4 pages.

Axisa, F. et al., "Elastic and Conformable Electronic Circuits and Assemblies using MID in polymer", 6th International Conference on Polymers and Adhesives in Microelectronics and Photonics, IEEE Polytronic 2007 Conference, (2007), pp. 280-286.

Azimi, J. et al., "Batch Active Learning via Coordinated Matching", In Proceedings of the 29th International Conference on Machine Learning, (2012), pp. 1-8.

Azimi, J. et al., "Batch Bayesian Optimization via Simulation Matching", In Advances in Neural Information Processing Systems (NIPS), (2010), pp. 1-9.

Azimi, J. et al., "Hybrid Batch Bayesian Optimization", In Proceedings of the 29th International Conference on Machine Learning, (2012), pp. 1-12.

Barbeau, H. et al., "Recovery of locomotion after chronic spinalization in the adult cat", Brain Research, (1987), vol. 412, No. 1, pp. 84-95.

Bareyre, F. et al., "The injured spinal cord spontaneously forms a new intraspinal circuit in adult rats", Nature Neuroscience, (2004), vol. 7, No. 3, pp. 269-277.

Basso, D. et al., "MASCIS Evaluation of Open Field Locomotor Scores: Effects of Experience and Teamwork on Reliability", Journal of Neurotrauma, (1996), vol. 13, No. 7, pp. 343-359.

Bizzi, E. et al., "Modular organization of motor behavior", Zeitschrift fr Naturforschung, (1998), vol. 53, No. 7-8, pp. 510-517.

Brochu, et al., "A Tutorial on Bayesian Optimization of Expensive Cost Functions, with Application to Active User Modeling and Hierarchical Reinforcement Learning", In TR-2009-23, UBC, (2009), pp. 1-49.

Brosamle, C. et al., "Cells of Origin, Course, and Termination Patterns of the Ventral, Uncrossed Component of the Mature Rat Corticospinal Tract", The Journal of Comparative Neurology, (1997), vol. 386, No. 2, pp. 293-303.

Bruckenstein, S. et al., "An experimental study of nonuniform current distribution at rotating disk electrodes", Journal of the Electrochemical Society, (1970), vol. 117, No. 8, pp. 1044-1048.

Bubeck, S. et al., "Online Optimization in X-Armed Bandits", Advances in Neural Information Processing Systems (NIPS), (2008), pp. 1-8.

Bubeck, S. et al., "Pure Exploration in Finitely-Armed and Continuous-Armed Bandits problems", In ALT, (2009), pp. 1-35.

Burke, R., "Group la Synaptic Input to Fast and Slow Twitch Motor Units of Cat Triceps Surae", The Journal of Physiology, (1968), vol. 196, No. 3, pp. 605-630.

Cai, L. et al., "Implications of Assist-As-Needed Robotic Step Training after a Complete Spinal Cord Injury on Intrinsic Strategies of Motor Learning", The Journal of Neuroscience, (2006), vol. 26, No. 41, pp. 10564-10568.

Canadian Office Action in counterpart Canadian Patent Application No. 2823592 mailed Oct. 5, 2017, 4 pages.

Canadian Office Action in counterpart Canadian Patent Application No. 2824782 mailed Nov. 29, 2017, 4 pages.

Canadian Office Action in counterpart Canadian Patent Application No. 2825550 mailed Jan. 24, 2018, 4 pages.

Canadian Office Action in counterpart Canadian Patent Application No. 2856202 mailed Jun. 19, 2018, 4 pages.

Canadian Office Action in counterpart Canadian Patent Application No. 2864473 mailed Aug. 31, 2018, 5 pages.

Canadian Office Action in counterpart Canadian Patent Application No. 2864473 mailed Aug. 14, 2020, 4 pages.

Canadian Office Action in counterpart Canadian Patent Application No. 2864473 mailed Jul. 30, 2019, 5 pages.

Canadian Office Action in counterpart Canadian Patent Application No. 2906779 mailed Apr. 9, 2021, 4 pages.

Canadian Office Action in counterpart Canadian Patent Application No. 2906779 mailed May 7, 2020, 5 pages.

Canadian Office Action in counterpart Canadian Patent Application No. 2925754 mailed Nov. 27, 2020, 5 pages.

Canadian Office Action in counterpart Canadian Patent Application No. 2925754 mailed Sep. 28, 2021, 4 pages.

Canadian Office Action in counterpart Canadian Patent Application No. 2958924 mailed Jul. 14, 2022, 4 pages.

Canadian Office Action in counterpart Canadian Patent Application No. 2958924 mailed Oct. 21, 2021, 5 pages.

Canadian Office Action in counterpart Canadian Patent Application No. 3030615 mailed Jun. 19, 2023, 5 pages.

Canadian Office Action in counterpart Canadian Patent Application No. 3030615 mailed Sep. 6, 2022, 5 pages.

Capogrosso, M. et al., "A Brain-Spinal Interface Alleviating Gait Deficits after Spinal Cord Injury in Primates", Nature, (2016), vol. 539, No. 7628, pp. 284-288.

Capogrosso, M. et al., "A Computational Model for Epidural Electrical Stimulation of Spinal Sensorimotor Circuits", Journal of Neuroscience, (2013), vol. 33, No. 49, pp. 19326-19340.

Carhart, M. et al., "Epidural Spinal-Cord Stimulation Facilitates Recovery of Functional Walking Following Incomplete Spinal-Cord Injury", IEEE Transactions on Neural Systems and Rehabilitation Engineering, (2004), vol. 12, No. 1, pp. 32-42.

Chatagny, P. et al., "Distinction between hand dominance and hand preference in primates: a behavioral investigation of manual dexterity in nonhuman primates (macaques) and human subjects", Brain and Behavior, (2013), vol. 3, No. 5, pp. 575-595.

Colgate, E. et al., "An Analysis of Contact Instability in Terms of Passive Physical Equivalents", Proceedings of the 1989 IEEE International Conference on Robotics and Automation, Scottsdale, Arizona, (1989), pp. 404-409.

(56)　　　　　References Cited

OTHER PUBLICATIONS

Communication Pursuant to Article 94(3) EPC in counterpart European Application No. 19209911.7 mailed Jul. 20, 2023, 5 pages.
Communication Pursuant to Article 94(3) EPC in counterpart European Application No. 19209911.7 mailed Mar. 1, 2023, 2 pages.
Communication Pursuant to Article 94(3) EPC in counterpart European Patent Application No. 12760696.0 mailed Nov. 9, 2017, 5 pages.
Communication Pursuant to Article 94(3) EPC in counterpart European Patent Application No. 12847885.6 mailed Apr. 15, 2016, 5 pages.
Communication Pursuant to Article 94(3) EPC in counterpart European Patent Application No. 12847885.6 mailed Feb. 16, 2017, 5 pages.
Communication Pursuant to Article 94(3) EPC in counterpart European Patent Application No. 12848368.2 mailed May 9, 2018, 5 pages.
Communication Pursuant to Article 94(3) EPC in counterpart European Patent Application No. 14765477.6 mailed Nov. 14, 2018, 5 pages.
Communication Pursuant to Article 94(3) EPC in counterpart European Patent Application No. 14765477.6 mailed Sep. 27, 2019, 6 pages.
Communication Pursuant to Article 94(3) EPC in counterpart European Patent Application No. 14849355.4 mailed Jul. 20, 2018, 6 pages.
Communication Pursuant to Article 94(3) EPC in counterpart European Patent Application No. 15834593.4 mailed Jul. 17, 2019, 4 pages.
Communication Pursuant to Article 94(3) EPC in counterpart European Patent Application No. 15834593.4 mailed Jul. 30, 2020, 5 pages.
Communication Pursuant to Article 94(3) EPC in counterpart European Patent Application No. 17826212.7 mailed Dec. 21, 2020, 7 pages.
Communication Pursuant to Article 94(3) EPC in counterpart European Patent Application No. 18807366.2 mailed Mar. 22, 2023, 4 pages.
Communication Pursuant to Article 94(3) EPC in counterpart European Patent Application No. 20160841.1 mailed Mar. 6, 2024, 5 pages.
Communication Pursuant to Article 94(3) EPC in counterpart European Patent Application No. 20726108.2 mailed Mar. 20, 2024, 4 pages.
Communication Pursuant to Article 94(3) EPC in counterpart European Patent Application No. 211660801.7 mailed Mar. 7, 2024, 6 pages.
Communication Pursuant to Article 94(3) EPC in counterpart European Patent Application No. 21166801.7 mailed Mar. 7, 2024, 6 pages.
Communication Pursuant to Article 94(3) EPC in counterpart European Patent Application No. 24153829.7 mailed Apr. 4, 2025, 5 pages.
Communication Pursuant to Rule 114(2) EPC in counterpart European Patent Application No. 12847885.6 mailed Mar. 27, 2015, 28 pages.
Communication Regarding Extended European Search Report in counterpart European Patent Application No. 24153829.7 mailed May 22, 2024, 8 pages.
Cotton, D. P. J. et al., "A Multifunctional Capacitive Sensor for Stretchable Electronic Skins", IEEE Sensors Journal, IEEE Service Center, New York, NY, US, (2009), vol. 9, No. 12, pp. 2008-2009.
Coursera, "What is Machine Learning? Definition, Types, and Examples," Coursera, May 20, 2025. Retrieved from the Internet: <URL:https://www.coursera.org/articles/what-is-machine-learning>, 12 pages.
Courtine, G. et al., "Can experiments in nonhuman primates expedite the translation of treatments for spinal cord injury in humans?", Nature Medicine, (2007), vol. 13, No. 5, pp. 561-566.

Courtine, G. et al., "Modulation of multisegmental monosynaptic responses in a variety of leg muscles during walking and running in humans", Journal of Physiology, (2007), vol. 582, No. 3, pp. 1125-1139.
Courtine, G. et al., "Recovery of supraspinal control of stepping via indirect propriospinal relay connections after spinal cord injury", Nature Medicine, (2008), vol. 14, No. 1, pp. 69-74.
Courtine, G. et al., "Transformation of nonfunctional spinal circuits into functional states after the loss of brain input", Nature Neuroscience, (2009), vol. 12, No. 10, pp. 1333-1342.
Cowley, K. et al., "Propriospinal neurons are sufficient for bulbospinal transmission of the locomotor command signal in the neonatal rat spinal cord", The Journal of Physiology, (2008), vol. 586, No. 6, pp. 1623-1635.
Cyganowski, A et al., "Stretchable electrodes for neuroprosthetic interfaces", Sensors, 2012 IEEE, Taipei, (2012), pp. 1-4.
Dani, V. et al., "Stochastic Linear Optimization Under Bandit Feedback", In Proceedings of the 21st Annual Conference on Learning Theory (COLT), (2008), No. 101, pp. 1-15.
Danner, S. et al., "Human Spinal locomotor control is based on flexibly organized burst generators", Brain: A Journal of Neurology, (2015), vol. 138, No. 3, pp. 577-588.
Danner, S. M. et al., "Body Position Influences Which neural structures are recruited by lumbar transcutaneous spinal cord stimulation", PLoS One, (2016), vol. 11, No. 1, pp. 1-13.
Danner, S. M. et al., "Can the Human Lumbar Posterior Columns be Stimulated by Transcutaneous Spinal Cord Stimulation? A modeling study", Europe PMC funders author manuscripts, Artificial Organs, (2011), vol. 35, No. 3, pp. 257-262.
Decision to Refuse a European Patent Application in counterpart European Patent Application No. 15834593.4 mailed Oct. 28, 2021, 24 pages.
Definition of "Insert", Dictionary [online], Oxford English Dictionary, 2020 [retrieved on Dec. 15, 2022], 2 pages.
Desantana, J. M. et al., "Effectiveness of Transcutaneous Electrical Nerve Stimulation for Treatment of Hyperalgesia and Pain", Current Rheumatology Reports, (2008), vol. 10, pp. 492-499.
Dimitrijevic, M. M. et al. "Evidence for a Spinal Central Pattern Generator in Humans", Annals New York Academy Sciences, (1998), vol. 860, No. 1, pp. 360-376.
Dimitrijevic, M. M. et al., "Clinical Elements for the Neuromuscular Stimulation and Functional Electrical Stimulation protocols in the Practice of Neurorehabilitation", Artificial Organs, vol. 26, No. 4, (2002), pp. 256-259.
Dimitrijevic, M. R. et al., "Electrophysiological characteristics of H-reflexes elicited by percutaneous stimulation of the cauda equina", Abstract No. 4927, 34th Annual Meeting of the Society for Neuroscience, San Diego, CA (2004), 1 page.
Dominici, N. et al. "Versatile robotic interface to evaluate, enable and train locomotion and balance after neuromotor disorders", Nature Medicine, (2012), vol. 18, No. 7, pp. 1-8.
Notice of Allowance in U.S. Appl. No. 15/753,963, mailed Dec. 13, 2021, 8 pages.
Notice of Allowance in U.S. Appl. No. 15/975,678, mailed Mar. 4, 2022, 9 pages.
Notice of Allowance in U.S. Appl. No. 16/200,467, mailed May 19, 2021, 8 pages.
Office Action in U.S. Appl. No. 14/355,812, mailed Apr. 8, 2015, 9 pages.
Office Action in U.S. Appl. No. 14/355,812, mailed Sep. 21, 2015, 10 pages.
Office Action in U.S. Appl. No. 14/775,618, mailed Jul. 13, 2016, 17 pages.
Office Action in U.S. Appl. No. 14/775,618, mailed Apr. 25, 2017, 19 pages.
Office Action in U.S. Appl. No. 14/925,791, mailed Jul. 20, 2017, 12 pages.
Office Action in U.S. Appl. No. 15/025,201, mailed Oct. 3, 2017, 10 pages.
Office Action in U.S. Appl. No. 15/096,014, mailed Sep. 14, 2017, 13 pages.
Office Action in U.S. Appl. No. 15/208,529, mailed Oct. 18, 2016, 9 pages.

(56)　　　　　References Cited

OTHER PUBLICATIONS

Office Action in U.S. Appl. No. 15/208,529, mailed Jul. 27, 2018, 8 pages.
Office Action in U.S. Appl. No. 15/208,529, mailed Apr. 19, 2019, 12 pages.
Office Action in U.S. Appl. No. 15/208,529, mailed Oct. 28, 2019, 7 pages.
Office Action in U.S. Appl. No. 15/344,381, mailed Apr. 17, 2019, 26 pages.
Office Action in U.S. Appl. No. 15/344,381, mailed Dec. 30, 2019, 40 pages.
Office Action in U.S. Appl. No. 15/344,381, mailed Aug. 4, 2020, 41 pages.
Office Action in U.S. Appl. No. 15/505,053, mailed Jun. 4, 2019, 10 pages.
Office Action in U.S. Appl. No. 15/506,696, mailed Jul. 22, 2019, 9 pages.
Office Action in U.S. Appl. No. 15/713,456, mailed Oct. 24, 2018, 13 pages.
Office Action in U.S. Appl. No. 15/740,323, mailed Apr. 7, 2020, 12 pages.
Office Action in U.S. Appl. No. 15/740,323, mailed Nov. 20, 2020, 12 pages.
Office Action in U.S. Appl. No. 15/740,323, mailed Mar. 29, 2021, 11 pages.
Office Action in U.S. Appl. No. 15/740,323, mailed Nov. 26, 2021, 14 pages.
Office Action in U.S. Appl. No. 15/740,323, mailed May 11, 2022, 14 pages.
Office Action in U.S. Appl. No. 15/740,323, mailed Feb. 15, 2023, 16 pages.
Office Action in U.S. Appl. No. 15/750,499, mailed Oct. 31, 2019, 24 pages.
Office Action in U.S. Appl. No. 15/750,499, mailed Aug. 6, 2020, 28 pages.
Office Action in U.S. Appl. No. 15/750,499, mailed Aug. 6, 2021, 30 pages.
Office Action in U.S. Appl. No. 15/753,963, mailed Nov. 13, 2020, 13 pages.
Office Action in U.S. Appl. No. 15/753,963, mailed Jul. 16, 2021, 9 pages.
Office Action in U.S. Appl. No. 15/821,076, mailed Oct. 10, 2018, 13 pages.
Office Action in U.S. Appl. No. 15/975,678, mailed Jan. 8, 2020, 14 pages.
Office Action in U.S. Appl. No. 15/975,678, mailed Jul. 29, 2020, 17 pages.
Office Action in U.S. Appl. No. 15/975,678, mailed Feb. 10, 2021, 12 pages.
Office Action in U.S. Appl. No. 15/975,678, mailed Jul. 20, 2021, 21 pages.
Office Action in U.S. Appl. No. 16/200,467, mailed Apr. 10, 2020, 10 pages.
Office Action in U.S. Appl. No. 16/200,467, mailed Nov. 24, 2020, 7 pages.
Office Action in U.S. Appl. No. 16/479,201, mailed Aug. 25, 2022, 24 pages.
Office Action in U.S. Appl. No. 16/479,201, mailed Jun. 1, 2023, 18 pages.
Office Action in U.S. Appl. No. 16/615,765, mailed May 12, 2021, 13 pages.
Office Action in U.S. Appl. No. 16/615,765, mailed Dec. 6, 2021, 15 pages.
Office Action in U.S. Appl. No. 16/615,765, mailed Jun. 20, 2022, 18 pages.
Office Action in U.S. Appl. No. 16/615,765, mailed Apr. 6, 2023, 18 pages.
Office Action in U.S. Appl. No. 17/269,970, mailed Jan. 5, 2022, 16 pages.

Office Action in U.S. Appl. No. 17/269,970, mailed Oct. 13, 2022, 21 pages.
Office Action in U.S. Appl. No. 17/269,970, mailed Aug. 16, 2023, 7 pages.
Office Action in U.S. Appl. No. 17/270,402, mailed Apr. 28, 2023, 9 pages.
Office Action in U.S. Appl. No. 17/407,043, mailed Sep. 13, 2023, 7 pages.
Office Action in U.S. Appl. No. 15/208,529, mailed Jul. 13, 2017, 9 pages.
Drew, T. et al., "Cortical mechanisms involved in visuomotor coordination during precision walking", Brain Research Reviews, (2008), vol. 57, No. 1, pp. 199-211.
Drummond, G. B. et al., "Thoracic impedance used for measuring chest wall movement in postoperative patients", British Journal of Anaesthesia, (1996), vol. 77, No. 3, pp. 327-332.
Dubinsky, R. M. et al., "Assessment: Efficacy of transcutaneous electric nerve stimulation in the treatment of pain in neurologic disorders (an evidenced-based review)", Report of the Therapeutics and Technology Assessment Subcommittee of the American Academy of Neurology, Neurology, (2010), vol. 74, No. 2, pp. 173-176.
Dunne, L. et al., "Initial development and testing of a novel foam-based pressure sensor for wearable sensing", Journal of NeuroEngineering and Rehabilitation, (2005), vol. 2, No. 4, pp. 1-7.
Duschau-Wicke, A. et al., "Patient-cooperative control increases active participation of individuals with SCI during robot-aided gait training", Journal of NeuroEngineering and Rehabilitation, (2010), vol. 7, No. 43, pp. 1-13.
Edgerton, V. et al., "Robotic Training and Spinal Cord Plasticity", Brain Research Bulletin, (2009), vol. 78, No. 1, pp. 4-12.
Edgerton, V. et al., "Training Locomotor Networks", Brain Research Reviews, (2008), vol. 57, No. 1, pp. 241-254.
Edgerton, V. R. et al., "Epidural stimulation of the spinal cord in spinal cord injury: current status and future challenges", Expert Review of Neurotherapeutics, (2011), vol. 11, No. 10, pp. 1351-1353.
EPO Communication and Supplementary European Search Report in counterpart European Patent Application No. 17745012.9 mailed Aug. 13, 2019, 8 pages.
European Opposition filed in counterpart European Patent Application No. 17826212.7 mailed Dec. 2, 2022, 56 pages.
European Reply to Communication in counterpart European Patent Application No. 12847885.6 mailed Oct. 24, 2016, 4 pages.
Extended European Search Report in counterpart European Patent Application No. 14765477.6 mailed Nov. 8, 2016, 10 pages.
Extended European Search Report in counterpart European Patent Application No. 14849355.4 mailed May 10, 2017, 7 pages.
Extended European Search Report in counterpart European Patent Application No. 15834593.4 mailed Apr. 4, 2018, 7 pages.
Extended European Search Report in counterpart European Patent Application No. 15836927.2 mailed Mar. 1, 2018, 9 pages.
Extended European Search Report in counterpart European Patent Application No. 16825005.8 mailed Feb. 19, 2019, 8 pages.
Extended European Search Report in counterpart European Patent Application No. 16833973.7 mailed Dec. 13, 2018, 6 pages.
Extended European Search Report in counterpart European Patent Application No. 18173218.1 mailed Jan. 7, 2019, 6 pages.
Extended European Search Report in counterpart European Patent Application No. 18744685.1 mailed Sep. 7, 2020, 8 pages.
Extended European Search Report in counterpart European Patent Application No. 19201998.2 mailed Apr. 21, 2020, 7 pages.
Extended European Search Report in counterpart European Patent Application No. 19211738.0 mailed May 27, 2020, 8 pages.
Extended European Search Report in counterpart European Patent Application No. 19851613.0 mailed Apr. 19, 2022, 9 pages.
Extended European Search Report in counterpart European Patent Application No. 19852797.0 mailed Apr. 19, 2022, 6 pages.
Extended European Search Report in counterpart European Patent Application No. 20020190.3 mailed Oct. 5, 2020, 7 pages.
Extended European Search Report in counterpart European Patent Application No. 20163794.9 mailed Sep. 18, 2020, 7 pages.
Extended European Search Report in counterpart European Patent Application No. 20164082.8 mailed Jul. 21, 2020, 7 pages.

(56) References Cited

OTHER PUBLICATIONS

Extended European Search Report in counterpart European Patent Application No. 20175385.2 mailed Jan. 22, 2021, 8 pages.

Extended European Search Report in counterpart European Patent Application No. 21166801.7 mailed Aug. 17, 2021, 11 pages.

Extended European Search Report in counterpart European Patent Application No. 23189900.6 mailed Jan. 15, 2024, 7 pages.

Extended European Search Report in counterpart European Patent Application No. EP12847885.6 mailed May 6, 2015, 7 pages.

Extended European Search Report in counterpart European Patent Application No. 19211698.6 mailed May 28, 2020, 6 pages.

Feng, G. H. et al., "Universal concept for fabricating micron to millimeter sized 3-D parylene structures on rigid and flexible substrates", in Proc. IEEE 15th Internal Conference on Micro Electro Mechanical System, Kyoto, Japan, (2003), pp. 594-597.

Fleshman, J. et al., "Electronic Architecture of Type-Identified a-Motoneurons in in the Cat Spinal Cord", Journal of Neurophysiology, (1988), vol. 60, No. 1, pp. 60-85.

Fong, A J. et al., "Recovery of control of posture and locomotion after a spinal cord injury: solutions staring us in the face", Progress in Brain Research, Elsevier Amsterdam, Netherlands, (2009), vol. 175, Chapter 25, pp. 393-418.

Frey, M. et al., "A Novel Mechatronic Body Weight Support System", IEEE Transactions on Neural Systems and Rehabilitation Engineering, (2006), vol. 14, No. 3, pp. 311-321.

Fuentes, R. et al., "Spinal Cord Stimulation Restores Locomotion in Animal Models of Parkinson's Disease," Science, (2009), vol. 323, No. 5921, pp. 1578-1582.

Ganley, K. J. et al., "Epidural Spinal Cord Stimulation Improves Locomotor Performance in Low Asia C, Wheelchair-Dependent, Spinal Cord-Injured Individuals: Insights from Metabolic Response", Topics in Spinal Cord Injury Rehabilitation, (2005), vol. 11, No. 2, pp. 50-63.

Gerasimenko, Y. et al., "Initiation and modulation of locomotor circuitry output with multisite transcutaneous electrical stimulation of the spinal cord in noninjured humans", Journal of Neurophysiology, (2015), vol. 113, No. 3, pp. 834-842.

Gerasimenko, Y. et al., "Noninvasive Reactivation of Motor Descending Control after Paralysis", Journal of Neurotrauma, (2015), vol. 32, No. 24, pp. 1968-1980.

Gerasimenko, Y. et al., "Novel and Direct Access to the Human Locomotor Spinal Circuitry", Journal of Neuroscience, (2010), vol. 30, No. 10, pp. 3700-3708.

Gerasimenko, Y. et al., "Spinal cord reflexes induced by epidural spinal cord stimulation in normal awake rats", Journal of Neuroscience Methods, (2006), vol. 157, No. 2, pp. 253-263.

Gerasimenko, Y. et al., "Transcutaneous electrical spinal-cord stimulation in humans", Annals of Physical and Rehabilitation Medicine, (2015), vol. 58, No. 4, pp. 225-231.

Gerasimenko, Y. P. et al., "Control of Locomotor Activity in Humans and Animals in the Absence of Supraspinal Influences", Neuroscience and Behavioral Physiology, (2002), vol. 32, No. 4, pp. 417-423.

Gerasimenko, Y. P. et al., "Epidural Spinal Cord Stimulation Plus Quipazine Administration Enable Stepping Complete Spinal Adult Rats", Journal of Neurophysiology, (2007), vol. 98, No. 5, pp. 2525-2536.

Gilja, V. et al., "A high-performance neural prosthesis enabled by control algorithm design—with supplementary materials", Nature Neuroscience, (2012), vol. 15, No. 12, pp. 1-56.

Ginsbourger, D. et al., "Kriging is well-suited to parallelize optimization", Computational Intelligence in Expensive Optimization Problems, Berlin, Heidelberg: Springer Berlin Heidelberg, (2010), Ch. 6, pp. 131-162.

Gittins, J.C., "Bandit Processes and Dynamic Allocation Indices", Journal of the Royal Statistical Society B, (1979), vol. 41, No. 2, pp. 148-164.

Giuliano, F. et al., "Neural Control of Erection", Physiology & Behavior, (2004), vol. 83, No. 2, pp. 189-201.

Graf, N. et al., "Electrochemically Stimulated Release from Liposomes Embedded in a Polyelectrolyte Multilayer", Advanced Functional Materials, (2011), vol. 21, No. 9, pp. 1666-1672.

Graz, I. et al., "Flexible ferroelectret field-effect transistor for large-area sensor skins and microphones", Applied Physics Letters, American Institute of Physics, (2006), vol. 89, No. 7, pp. 73501-1-73501-3.

Aching knee or sore back? New app helps doctors treat pain, medicalxpress.com. May 8, 2017, Retrieved from the Internet: <URL: https://medicalxpress.com/news/2017-05-aching-knee-sore-app-doctors.html>, 1 page.

Back pain and body posture infographic, Alamy.com. Apr. 11, 2017, Retrieved from the Internet: <URL:https://www.alamy.com/stock-photo-back-pain-and-body-posture-infographic-with-anatomical-illustrations-141494074.html?imageid=27CC5905-F123-4DSC-847A4C76D50631C1&p=313080&pn=1&search Id=526c9d4db7f91a3e259d7b785fa370c3&searchtype=0>, 2 pages.

Extended European Search Report in EP25165562.7, mailed Sep. 2, 2025, 9 pages.

Ichiyama et al. "Step training reinforces specific spinal locomotor circuitry in adult spinal rats." Journal of Neuroscience 28.29 (2008): 7370-7375.

Male and female muscle and skeletal systems, Shutterstock.com. Jan. 15, 2021, Retrieved from the Internet: <URL: https://www.shutterstock.com/image-illustration/male-female-muscle-skeletal-systems-xray-1895443960>, 2 pages.

Office Action in U.S. Appl. No. 16/953,322, mailed Aug. 29, 2025, 12 pages.

Office Action in U.S. Appl. No. 18/339,085, mailed Sep. 4, 2025, 15 pages.

Office Action in U.S. Appl. No. 29/874,320, mailed Aug. 18, 2025, 9 pages.

Screenshots of the electric patient-reported outcome app final prototype, Researchgate.net. Oct. 2020, Retrieved from the Internet: <URL:https://www.researchgate.net/figure/Screenshots-of-the-electronic-patient-reported-outcome-app-final-prototype_fig>, 1 page.

Office Action in U.S. Appl. No. 17/206,007, mailed Dec. 15, 2025, 18 pages.

Office Action in U.S. Appl. No. 17/511,496, mailed Oct. 3, 2025, 17 pages.

Office Action in U.S. Appl. No. 18/297,222, mailed Feb. 12, 2026, 7 pages.

Office Action in U.S. Appl. No. 19/334,188, mailed Jan. 15, 2026, 21 pages.

Office Action in U.S. Appl. No. 19/335,824, mailed Feb. 19, 2026, 10 pages.

Office Action in U.S. Appl. No. 16/953,322, mailed Feb. 2, 2026, 8 pages.

* cited by examiner

*FIG. 3*
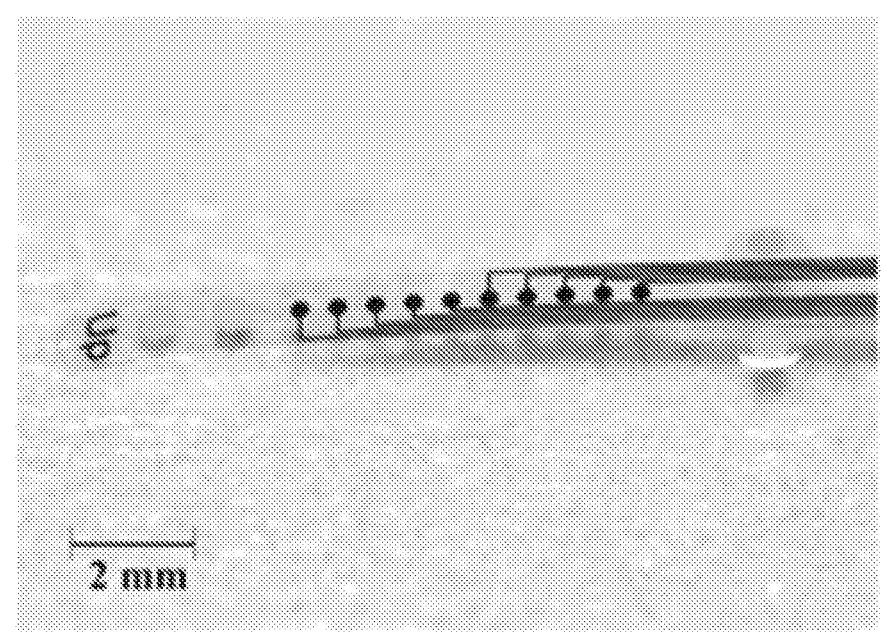
2 mm
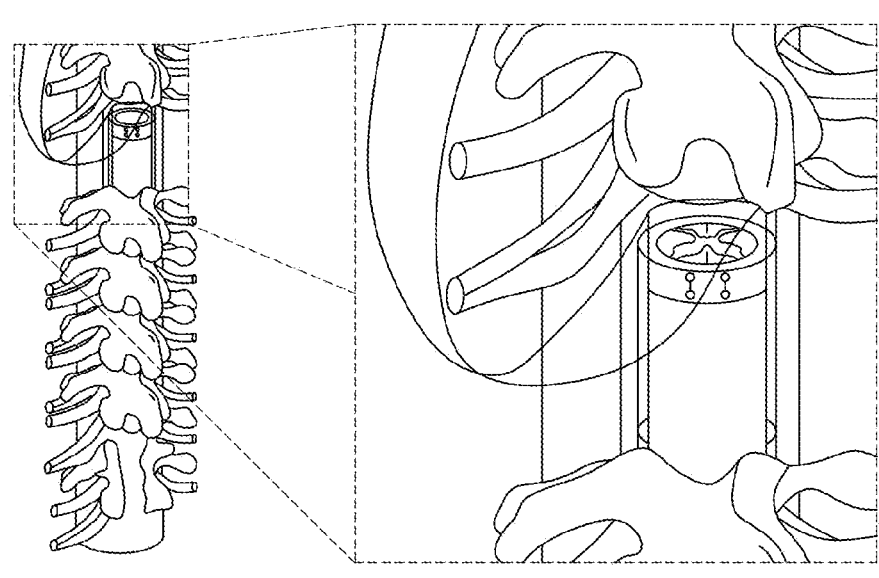
*FIG. 4*

| AIS Evaluation | | | |
|---|---|---|---|
| Neuro Level | T2 | Grade | B |
| Motor Score | | Sensory Score | |
| Right Upper Extremity | Left Upper Extremity | Right Light Touch | Left Light Touch |
| 25 | 25 | 50 | 50 |
| Right Lower Extremity | Left Lower Extremity | Right Pin Prick | Left Pin Prick |
| 0 | 0 | 38 | 33 |

Caudal Stimulation

L VL

L MH

L TA

L SOL

L MG

R VL

R MH

R TA

R SOL

R MG

Stim 1.6 mV 3 sec 0.04 sec
(15 Hz; 9V)

HIGH DENSITY EPIDURAL STIMULATION FOR FACILITATION OF LOCOMOTION, POSTURE, VOLUNTARY MOVEMENT, AND RECOVERY OF AUTONOMIC, SEXUAL, VASOMOTOR, AND COGNITIVE FUNCTION AFTER NEUROLOGICAL INJURY

CROSS REFERENCE TO RELATED APPLICATION(S)

This application is a continuation of U.S. patent application Ser. No. 17/473,406, filed Sep. 13, 2021, now U.S. Pat. No. 11,957,910, which is a continuation of U.S. patent application Ser. No. 15/878,325, filed Jan. 23, 2018, now U.S. Pat. No. 11,116,976, which is a continuation of U.S. patent application Ser. No. 14/790,729, filed Jul. 2, 2015, now U.S. Pat. No. 9,907,958, which is a continuation of U.S. patent application Ser. No. 13/978,035, filed Feb. 17, 2014, now U.S. Pat. No. 9,101,769, which is a national phase entry of PCT/US2012/020112, filed Jan. 3, 2012, which claims the benefit of U.S. Provisional Application No. 61/429,368, filed Jan. 3, 2011; U.S. Provisional Application No. 61/437,418, filed Jan. 28, 2011; and U.S. Provisional Application No. 61/469,555, filed Mar. 30, 2011, each of which is incorporated herein by reference in its entirety.

STATEMENT REGARDING FEDERALLY SPONSORED RESEARCH OR DEVELOPMENT

This invention was made with Government support under Grant No. W81XWH-09-2-0024, awarded by the United States Army, Medical Research and Materiel Command; and Grant No. EB007615, awarded by the National Institutes of Health. The Government has certain rights in this invention.

BACKGROUND

Field of the Invention

The present invention relates to the field neurological rehabilitation including traumatic spinal cord injury, non-traumatic spinal cord injury, stroke, movement disorders, brain injury, and other diseases or injuries that result in paralysis and/or nervous system disorder. Devices, pharmacological agents, and methods are provided to facilitate recovery of posture, locomotion, and voluntary movements of the arms, trunk, and legs, and recovery of autonomic, sexual, vasomotor, and cognitive function, in a human subject having spinal cord injury, brain injury, or any other neurological disorder.

Description of the Related Art

Serious spinal cord injuries (SCI) affect approximately 250,000 people in the United States, and roughly 11,000 new injuries occur each year. Of these injuries, approximately 50% are complete spinal cord injuries in which there is essentially total loss of sensory motor function below the level of the spinal lesion.

For chronic SCI humans, impressive levels of standing and stepping recovery has been demonstrated in certain incomplete SCI subjects with task specific physical rehabilitation training. A recent clinical trial demonstrated that 92% of the subjects regained stepping ability to almost a functional speed of walking three months after a severe yet incomplete injury (Dobkin et al., *Neurology*, 66(4): 484-93 (2006)) and in chronic subjects months to years after injury (Harkema et. al., *Archives of Physical Medicine and Rehabilitation:* 2011 epub). Furthermore, improved coordination of motor pool activation can be achieved with training in patients with incomplete SCI (Field-Fote et al., *Phys. Ther.,* 82 (7): 707-715 (2002)). On the other hand, there is no generally accepted evidence that an individual with a clinically complete SCI can be trained to the point where they could stand or locomote even with the aid of a "walker" (Wernig, *Arch Phys Med Rehabil.,* 86 (12): 2385-238 (2005)) and no one has shown the ability to regain voluntary movements and/or to recover autonomic, sexual, vasomotor, and/or improved cognitive function after a motor complete spinal cord injury.

To date, the consistently most successful intervention for regaining weight-bearing stepping in humans is weight-bearing step training, but that has been the case primarily in subjects with incomplete injuries.

The most effective future strategies for improving motor and autonomic functions that improve the quality of life post-SCI will likely involve the combination of many different technologies and strategies, as neurological deficits such as spinal cord injuries are complex, and there is a wide variability in the deficit profile among patients. In the long run, neuro-regenerative strategies hold significant promise for functional sensory-motor recovery from traumatic and progressive neurological deficits. Progress is already being made particularly in the case of acute treatment of incomplete spinal injuries. However, even when these strategies are perfected, other remedies will be needed. It is naive to think that neuro-regenerative approaches will recover fully functional postural and locomotor function as well as voluntary control of lower limb, and voluntary upper limb movement following a motor complete spinal injury.

SUMMARY OF THE INVENTION

Embodiments of the invention are for use with a human patient (or subject) who has a spinal cord with at least one selected spinal circuit and a neurologically derived paralysis in a portion of the patient's body. By way of non-limiting examples, when activated, the selected spinal circuit may (a) enable voluntary movement of muscles involved in at least one of standing, stepping, reaching, grasping, voluntarily changing positions of one or both legs, voiding the patient's bladder, voiding the patient's bowel, postural activity, and locomotor activity; (b) enable or improve autonomic control of at least one of cardiovascular function, body temperature, and metabolic processes; and/or (c) help facilitate recovery of at least one of an autonomic function, sexual function, vasomotor function, and cognitive function.

The paralysis may be a motor complete paralysis or a motor incomplete paralysis. The paralysis may have been caused by a spinal cord injury classified as motor complete or motor incomplete. The paralysis may have been caused by an ischemic or traumatic brain injury. The paralysis may have been caused by an ischemic brain injury that resulted from a stroke or acute trauma. By way of another example, the paralysis may have been caused by a neurodegenerative brain injury. The neurodegenerative brain injury may be associated with at least one of Parkinson's disease, Huntington's disease, Alzheimer's, ischemia, stroke, amyotrophic lateral sclerosis (ALS), primary lateral sclerosis (PLS), and cerebral palsy.

One exemplary embodiment is a method that includes positioning the human patient in a training device. The training device is configured to assist with physical training (e.g., at least one of standing, stepping, reaching, moving one or both legs, moving one or both feet, grasping, and stabilizing sitting posture) that is configured to induce neurological signals (e.g., at least one of postural proprioceptive signals, locomotor proprioceptive signals, and supraspinal signals) in the portion of the patient's body having the paralysis. The training device may include a robot training device configured to move automatically at least a portion of the portion of the patient's body having the paralysis. By way of non-limiting example, the training device may include a treadmill and a weight-bearing device configured to support at least a portion of the patient's body weight when the patient is positioned to use the treadmill. By way of another non-limiting example, the training device may include a device configured to bear at least a portion of the patient's body weight when the patient transitions between sitting and standing.

The selected spinal circuit has a first stimulation threshold representing a minimum amount of stimulation required to activate the selected spinal circuit, and a second stimulation threshold representing an amount of stimulation above which the selected spinal circuit is fully activated and adding the induced neurological signals has no additional effect on the at least one selected spinal circuit. The induced neurological signals are below the first stimulation threshold and insufficient to activate the at least one selected spinal circuit.

The method also includes applying electrical stimulation to a portion of a spinal cord of the patient. The electrical stimulation may be applied by an electrode array that is implanted epidurally in the spinal cord of the patient. Such an electrode array may be positioned at at least one of a lumbosacral region, a cervical region, and a thoracic region of the spinal cord. The electrical stimulation is below the second stimulation threshold such that the at least one selected spinal circuit is at least partially activatable by the addition of at least one of (a) a second portion of the induced neurological signals, and (b) supraspinal signals. While not a requirement, the first portion of the induced neurological signals may be the same as the second portion of the induced neurological signals. While also not a requirement, the electrical stimulation may not directly activate muscle cells in the portion of the patient's body having the paralysis. The electrical stimulation may include at least one of tonic stimulation and intermittent stimulation. The electrical stimulation may include simultaneous or sequential stimulation of different regions of the spinal cord.

If the paralysis was caused by a spinal cord injury at a first location along the spinal cord, the electrical stimulation may be applied by an electrode array that is implanted epidurally on the spinal cord of the patient at a second location below the first location along the spinal cord relative to the patient's brain.

Optionally, the method may include administering one or more neuropharmaceutical agents to the patient. The neuropharmaceutical agents may include at least one of a serotonergic drug, a dopaminergic drug, a noradrenergic drug, a GABAergic drug, and glycinergic drugs. By way of non-limiting examples, the neuropharmaceutical agents may include at least one of 8-0HDPAT, Way 100.635, QUIPAZINE® (a piperazine drug), KETANSERIN® (an antihypertensive agent), SR 57227A, ONDANSETRON® (an anti nausea drug), SB 269970, METHOXAMINE® (an α1 adrenergic receptor agonist), PRAZOSIN® (a sympatholytic drug), CLONIDINE® (an α2 adrenergic agonist and imidazoline receptor agonist), YOHIMBINE® (an indole alkaloid), SKF-81297, SCH-23390, QUINPIROLE® (a psychoactive drug), and ETICLOPRIDE® (a selective dopamine antagonist).

The electrical stimulation is defined by a set of parameter values, and activation of the selected spinal circuit may generate a quantifiable result. Optionally, the method may be repeated using electrical stimulation having different sets of parameter values to obtain quantifiable results generated by each repetition of the method. Then, a machine learning method may be executed by at least one computing device. The machine learning method builds a model of a relationship between the electrical stimulation applied to the spinal cord and the quantifiable results generated by activation of the at least one spinal circuit. A new set of parameters may be selected based on the model. By way of a non-limiting example, the machine learning method may implement a Gaussian Process Optimization.

Another exemplary embodiment is a method of enabling one or more functions selected from a group consisting of postural and/or locomotor activity, voluntary movement of leg position when not bearing weight, voluntary voiding of the bladder and/or bowel, return of sexual function, autonomic control of cardiovascular function, body temperature control, and normalized metabolic processes, in a human subject having a neurologically derived paralysis. The method includes stimulating the spinal cord of the subject using an electrode array while subjecting the subject to physical training that exposes the subject to relevant postural proprioceptive signals, locomotor proprioceptive signals, and supraspinal signals. At least one of the stimulation and physical training modulates in real time the electrophysiological properties of spinal circuits in the subject so the spinal circuits are activated by at least one of supraspinal information and proprioceptive information derived from the region of the subject where the selected one or more functions are facilitated.

The region where the selected one or more functions are facilitated may include one or more regions of the spinal cord that control (a) lower limbs; (b) upper limbs; (c) the subject's bladder; and/or (d) the subject's bowel. The physical training may include standing, stepping, sitting down, laying down, reaching, grasping, stabilizing sitting posture, and/or stabilizing standing posture.

The electrode array may include one or more electrodes stimulated in a monopolar configuration and/or one or more electrodes stimulated in a bipolar configuration. The electrode array includes a plurality of electrodes that may have an interelectrode spacing between adjacent electrodes of about 500 μm to about 1.5 mm. The electrode array may be an epidurally implanted electrode array. Such an epidurally implanted electrode array may be placed over at least one of a lumbosacral portion of the spinal cord, a thoracic portion of the spinal cord, and a cervical portion of the spinal cord.

The stimulation may include tonic stimulation and/or intermittent stimulation. The stimulation may include simultaneous or sequential stimulation of different spinal cord regions. Optionally, the stimulation pattern may be under control of the subject.

The physical training may include inducing a load bearing positional change in the region of the subject where locomotor activity is to be facilitated. The load bearing positional change in the subject may include standing, stepping, reaching, and/or grasping. The physical training may include robotically guided training.

The method may also include administering one or more neuropharmaceuticals. The neuropharmaceuticals may include at least one of a serotonergic drug, a dopaminergic drug, a noradrenergic drug, a GABAergic drug, and a glycinergic drug.

Another exemplary embodiment is a method that includes implanting an electrode array on the patient's spinal cord, positioning the patient in a training device configured to assist with physical training that is configured to induce neurological signals in the portion of the patient's body having the paralysis, and applying electrical stimulation to a portion of a spinal cord of the patient. The induced neurological signals is below the first stimulation threshold and insufficient to activate the at least one selected spinal circuit. The electrical stimulation is below the second stimulation threshold such that the at least one selected spinal circuit is at least partially activatable by the addition of at least one of (a) a second portion of the induced neurological signals, and (b) supraspinal signals. Optionally, the electrode array may be implanted on the dura of the patient's spinal cord.

Another exemplary embodiment is a system that includes a training device configured to assist with physically training of the patient, an implantable electrode array configured to be implanted on the dura of the patient's spinal cord, a stimulation generator connected to the implantable electrode array. When undertaken, the physical training induces neurological signals in the portion of the patient's body having the paralysis. The stimulation generator is configured to apply electrical stimulation to the implantable electrode array. Electrophysiological properties of at least one spinal circuit in the patient's spinal cord is modulated by the electrical stimulation and at least one of (1) a first portion of the induced neurological signals and (2) supraspinal signals such that the at least one spinal circuit is at least partially activatable by at least one of (a) the supraspinal signals and (b) a second portion of the induced neurological signals. The induced neurological signals and supraspinal signals are below the first stimulation threshold and insufficient to activate the at least one selected spinal circuit, and the electrical stimulation applied to the implantable electrode array is below the second stimulation threshold.

Another exemplary embodiment is a system that includes means for physically training the patient to induce neurological signals in the portion of the patient's body having the paralysis, and means for applying electrical stimulation to a portion of a spinal cord of the patient. Electrophysiological properties of at least one spinal circuit in the patient's spinal cord being modulated by the electrical stimulation and at least one of a first portion of the induced neurological signals and supraspinal signals such that the at least one spinal circuit is at least partially activatable by at least one of (a) the supraspinal signals and (b) a second portion of the induced neurological signals.

BRIEF DESCRIPTION OF THE SEVERAL VIEWS OF THE DRAWING(S)

FIG. 1 summarizes recent experiments in rats that were carried out to assess the effectiveness of epidural stimulation coupled with combined drug therapy in the treatment of complete spinal cord injuries. The combination of QUI-PAZINE and 8-0HDPAT with simultaneous epidural stimulation at spinal sites L2 and S1 results in robust coordinated stepping as early as one week after a complete spinal cord transection. Locomotor behavior observed from a typical rat before the injury and one week after a complete mid-thoracic spinal cord transection. The amount of body weight support provided to the rat is shown in red. One week post-injury, no spontaneous stepping activity is observed. Administration of QUIPAZINE (a 5-HT$_2$ receptor agonist) and 8-0HDPAT (a 5-HT$_{1/7}$ receptor agonist) results in erratic movements. Epidural stimulation simultaneously at L2 plus S1 in combination with either QUIPAZINE or 8-0HDPAT enables plantar stepping. The combination of epidural stimulation at L2 plus S1 with the administration of QUI-PAZINE plus 8-0HDPAT clearly has a synergistic effect, resulting in coordinated, plantar stepping with features resembling those observed pre-lesion. Sol, soleus; TA, tibialis anterior; MTP, metatarsal-phalangeal.

FIG. 2 illustrates step training with epidural stimulation at both L2 and S1 spinal sites in combination with use of QUIPAZINE and 8-0HDAPT (5-HT agonists) prevents degradation of neuronal function and promotes improvement of the stepping ability of spinal rats transected as adults. From top to bottom: Representative stick diagrams of left and right hindlimb movements during gait swing phase, recorded 8 weeks post-injury. The successive trajectories of the left and right limb endpoint (MTP) during a 10 s stepping sequence are shown. Blue, red, and black trajectories represent stance, drag, and swing phases. The gait diagrams reconstructed from the displacement of the left and right hindlimbs during stepping are displayed conjointly with the EMG activity of left and right soleus ("Sol") and tibialis anterior ("TA") muscles. Compared to a rat with no rehabilitation, the rat that received step training every other day for 7 weeks shows consistent hindlimb movements, coordination between the left and right sides, and increased recruitment of both extensor and flexor leg muscles.

FIG. 3 shows a photograph of an illustrative 1st generation high density epidural stimulating array comprising 10 electrodes.

FIG. 4 shows a schematic diagram of an illustrative laminectomy procedure for placing an epidural stimulating array over the lumbosacral spinal cord.

Figures 5A, 5B, 5C, 5D:
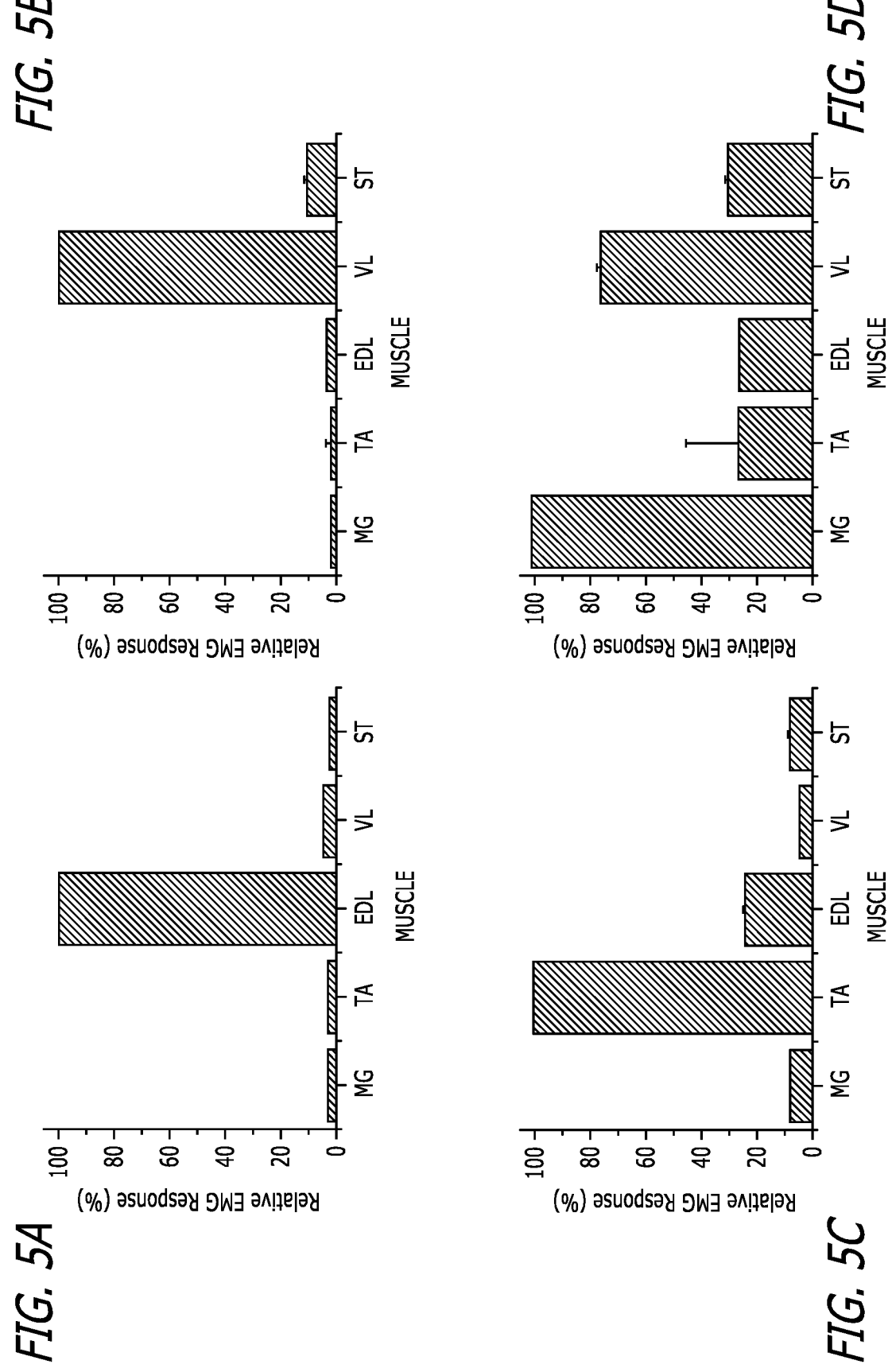

FIG. 5 panels A-D illustrates results for site-specific selective muscle activation. The extensor digitorum longus (EDL, panel A), vastus lateralis (VL, panel B), and tibialis anterior (TA, panel C) muscles were selectively activated using low-current stimulation at specific spinal sites. Preferential activation of the medial gastrocnemius (MG, panel D) muscle also was obtained, but occurred with co-activation of the VL. Data represent normalized peak-to-peak amplitudes of 10 averaged responses.

Figure 6:
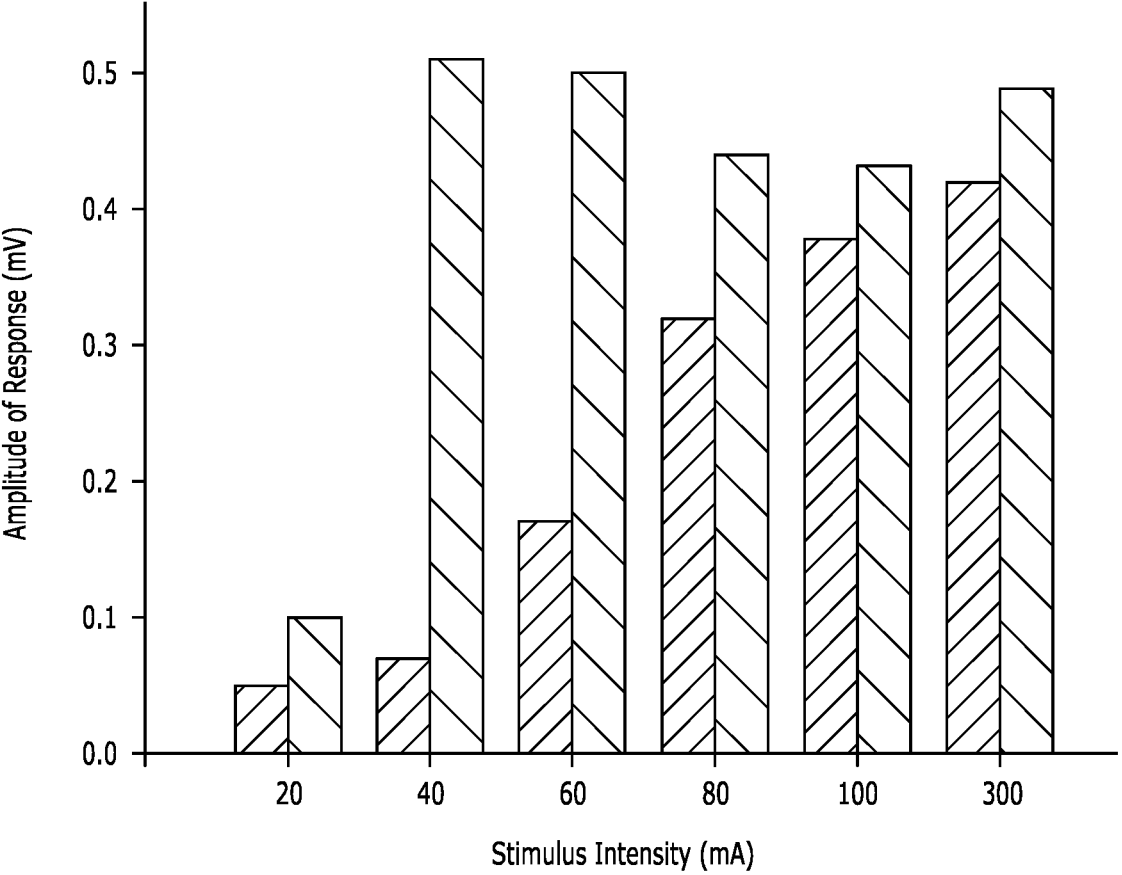

FIG. 6 shows that interelectrode distance modulates muscle recruitment. Using a smaller spacing (1500 μm, filled bars) bipolar configuration, graded muscle activation was achieved. With larger spacing (4500 μm, unfilled bars), approaching a monopolar configuration, a muscle quickly attained maximal activation at low currents. Thus, the specific goal and sensitivity requirements of a particular motor task may dictate optimal interelectrode spacing and whether a monopolar or bipolar configuration is chosen.

Figure 7:
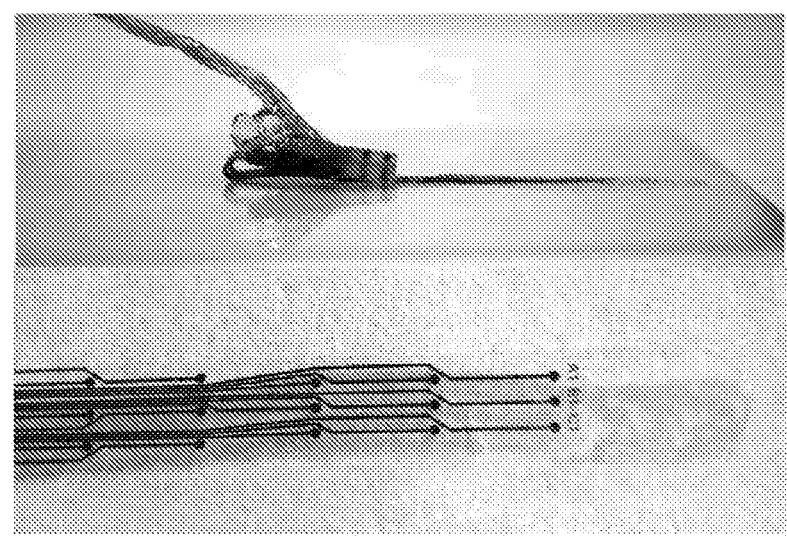

FIG. 7 shows a photograph of an illustrative 27 electrode rat epidural stimulation array (in a 9×3 configuration), including head-connector.

Figure 8:
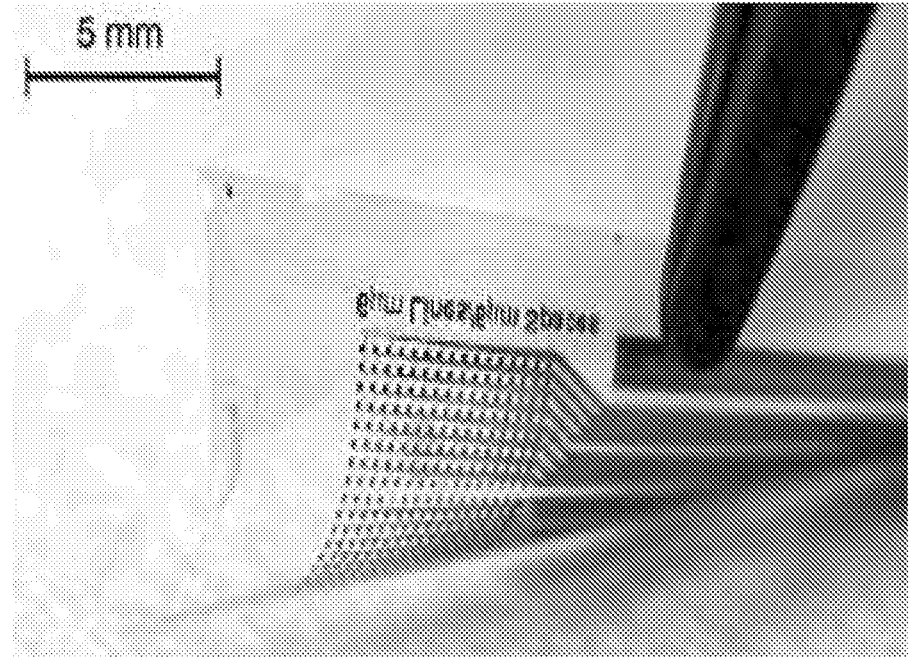

FIG. 8 shows a photograph of an illustrative 256 electrode array.

Figure 9:
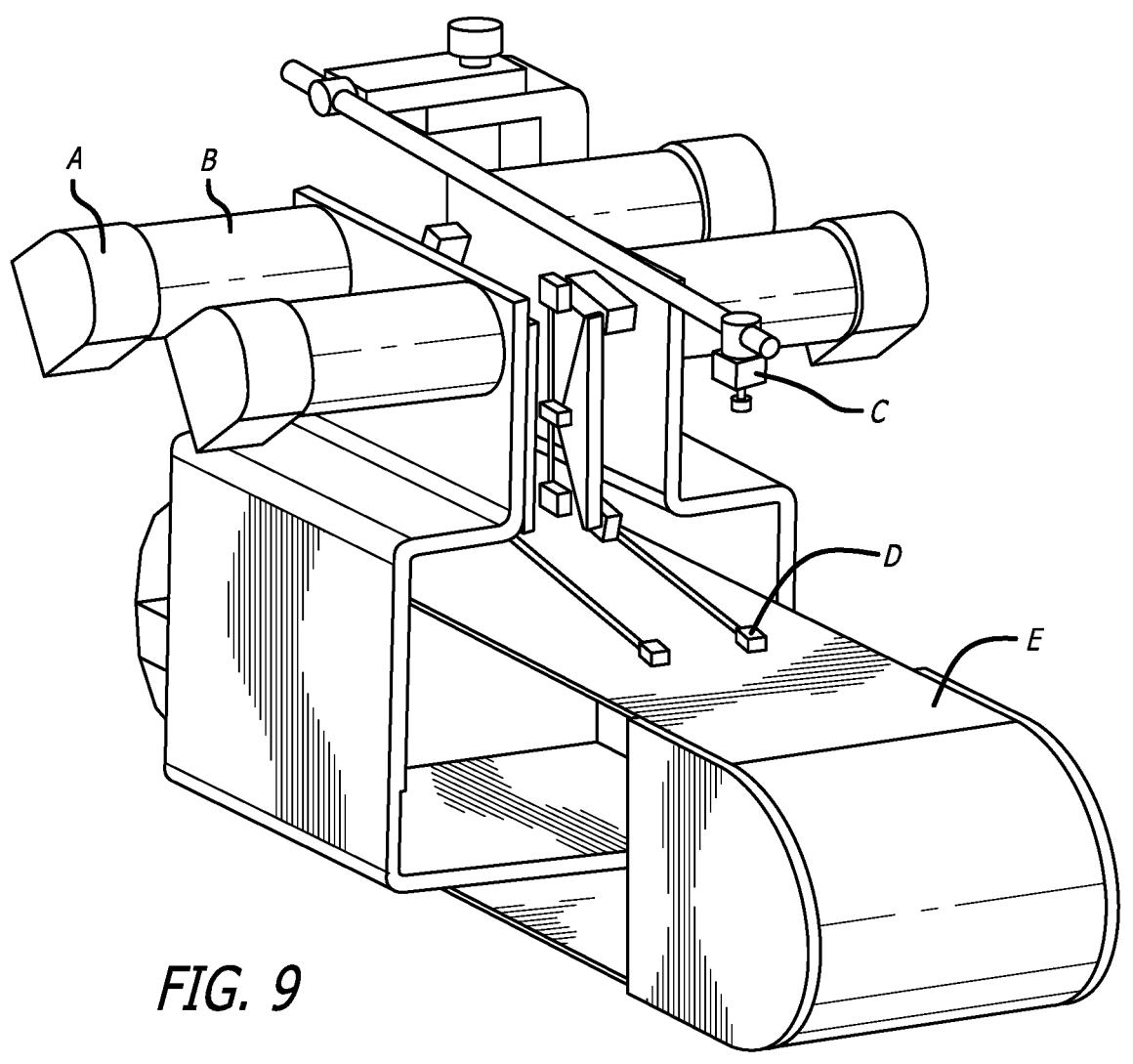

FIG. 9 illustrates a schematic of a step training robot. Illustrative components include: A) Optical encoder; B) Motor; C) Weight support; D) Manipulators; and E) Motorized treadmill.

Figures 10A, 10B:

FIGS. 10A and 10B show radiographic and clinical characteristics of an individual with motor complete, but sensory incomplete SCI. FIG. 10A: T2 weighted sagittal Magnetic Resonance Image of cervical spine at subject's injury site (C7-T1). Hyperintensity and myelomalacia noted at site of injury. FIG. 10B: AIS evaluation of the subject.

Figure 11A:
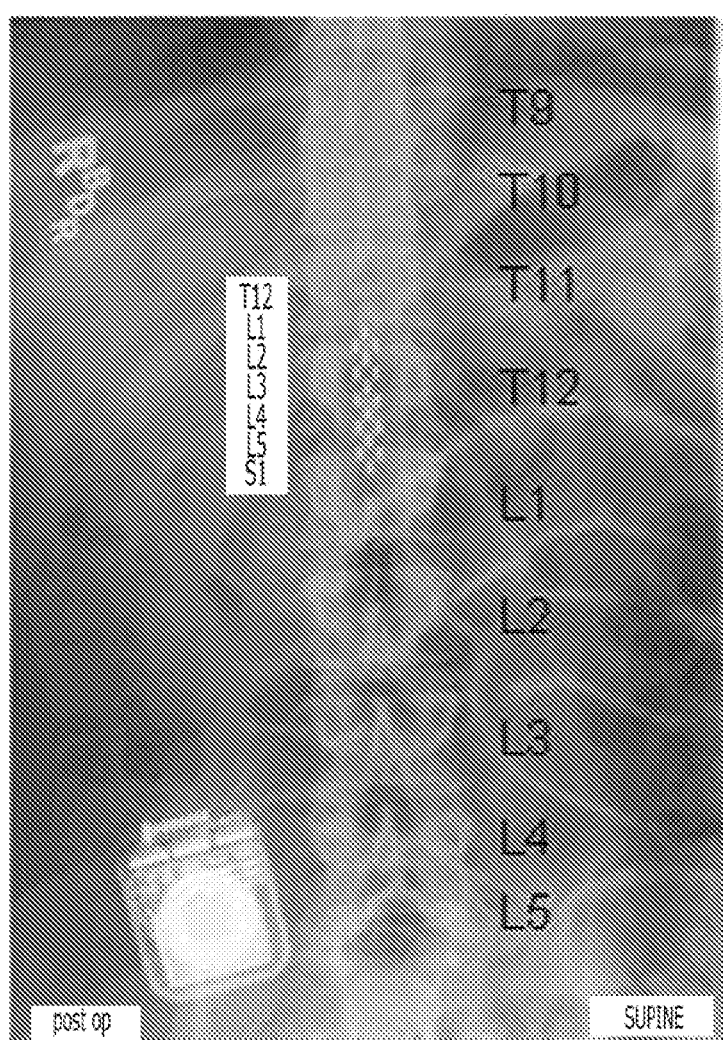

FIGS. 11A-11D illustrate localization of electrode array relative to motoneuron pools as identified with motor evoked potentials during surgical implantation. The voltage thresholds for evoked potentials of proximal muscles are lower when stimulating the more rostral electrodes. The voltage thresholds for motor evoked potentials of the distal muscles are lower when stimulating the caudal electrodes. FIG. 11A: Post-operative fluoroscopy of the thoracolumbar spine showing the location of the implanted electrode array and neurostimulator.

Figure 11B:
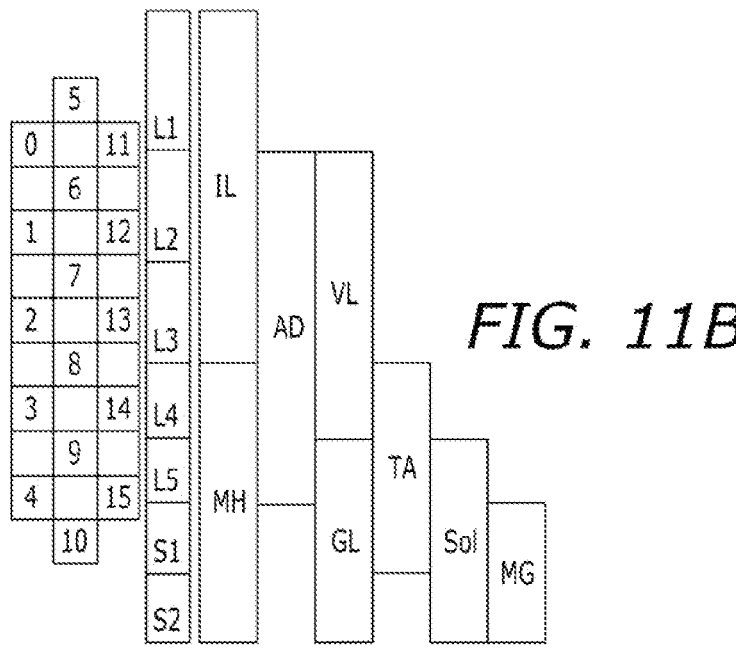
Figure 11C:
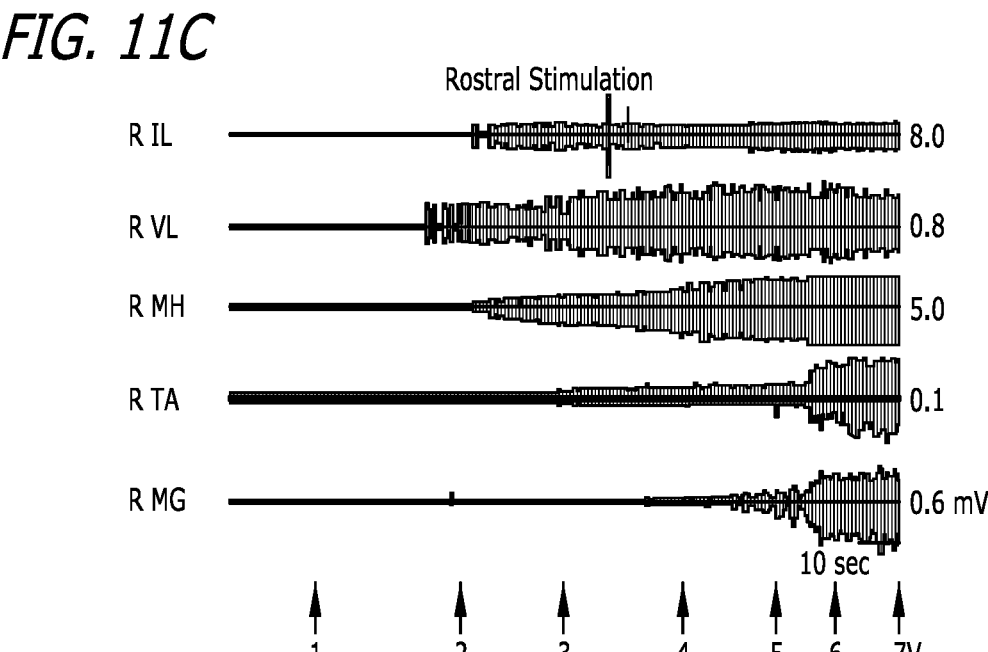
Figure 11D:
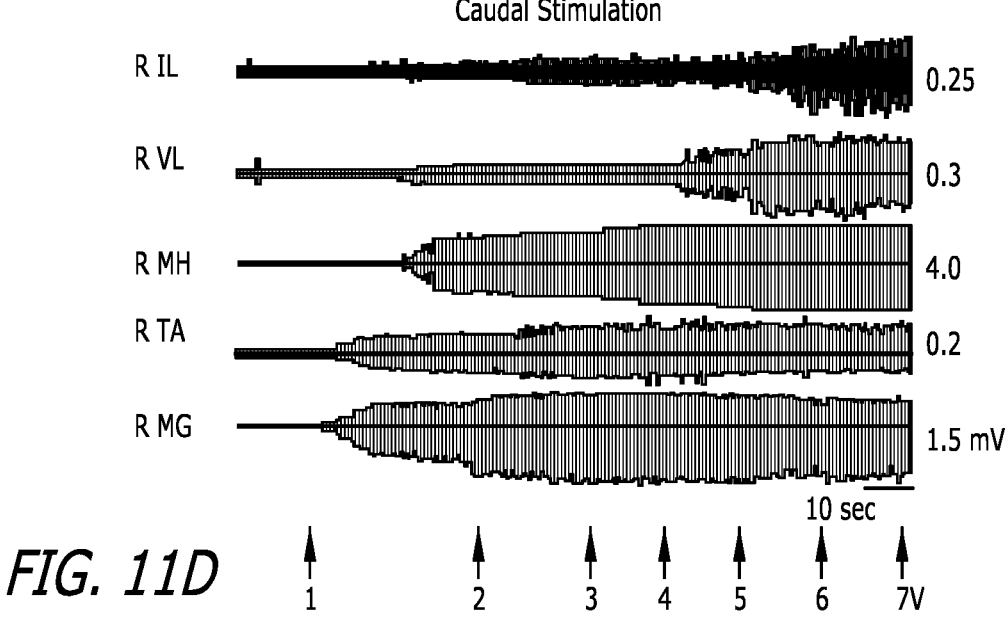

FIG. 11B: Depiction of 16-electrode array configuration relative to spinal dorsal roots and corresponding motoneuron pools identified using EMG recorded from leg muscles. FIGS. 11C and 11D: Motor evoked potentials elicited using epidural stimulation at 2 Hz, 210 us from 0.0 to 7 V with rostral electrodes, (5–: 6+) and caudal electrodes (10–: 9+) respectively. Muscles: IL: iliopsoas, AD: adductor magnus, VL: vastus lateralis, MH: medial hamstrings, TA: tibialis anterior, GL: gluteus maximus, SL: soleus, MG: medial gastrocnemius.

Figure 12:
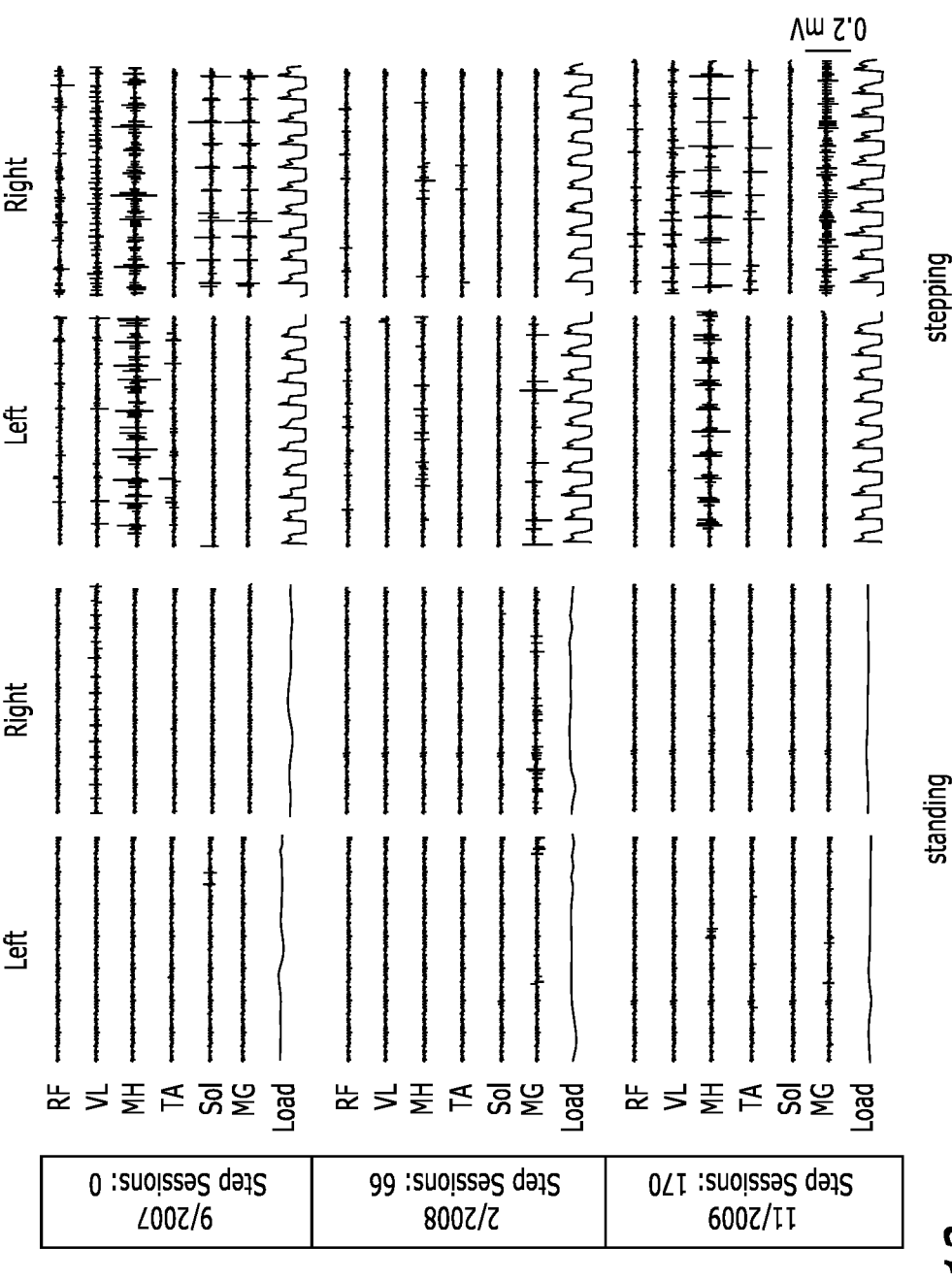

FIG. 12 illustrates lower extremity EMG activity during standing with BWST (panel A), and stepping with body weight support ("BWST") (panel B). Three different time points over a two-year period and 170 training sessions showed no change in the EMG pattern during standing or stepping.

Figures 13A, 13B:
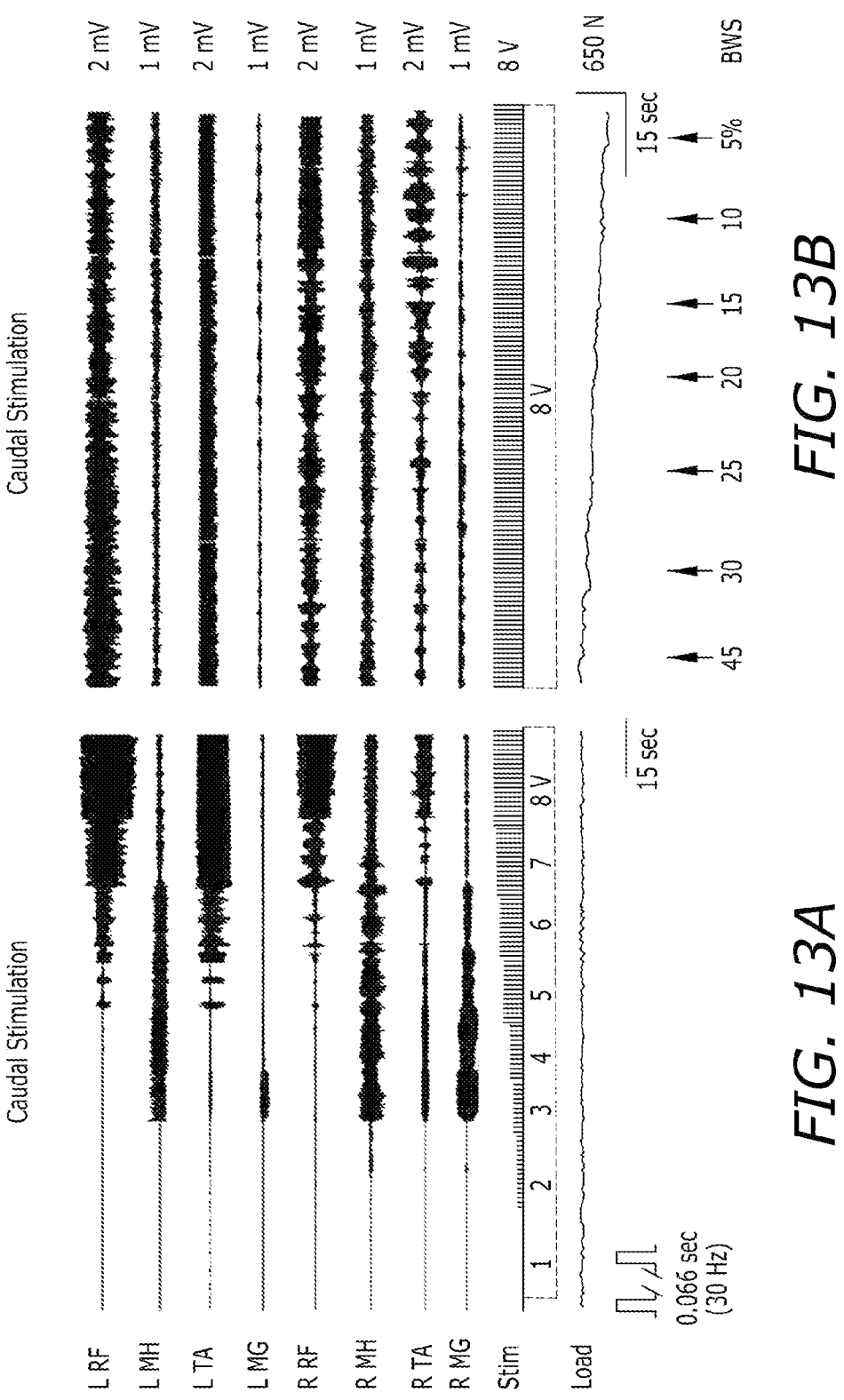

FIG. 13 shows EMG activity with epidural stimulation during independent standing. These data demonstrate that the output of the spinal circuitry can be sufficiently modulated by the proprioceptive input to sustain independent stepping. EMG activity increases in amplitude and becomes more constant bilaterally in most muscles with independent standing occurring at 8 V. Reducing BWS changed the EMG amplitudes and oscillatory patterns differently among muscles. EMG activity during standing with BWS and with epidural stimulation (15 Hz) of caudal lumbosacral segments (4/10/15–: 3/9+) (panel A) from 1-8V and 65% BWS and (panel B) at 8V while reducing the BWS from 45% to 5%. Muscle: rectus femoris (RF), medial hamstrings (MH), tibialis anterior (TA), and medial gastrocnemius (MG). Left (L) and right (R).

Figures 14A, 14B, 14C:
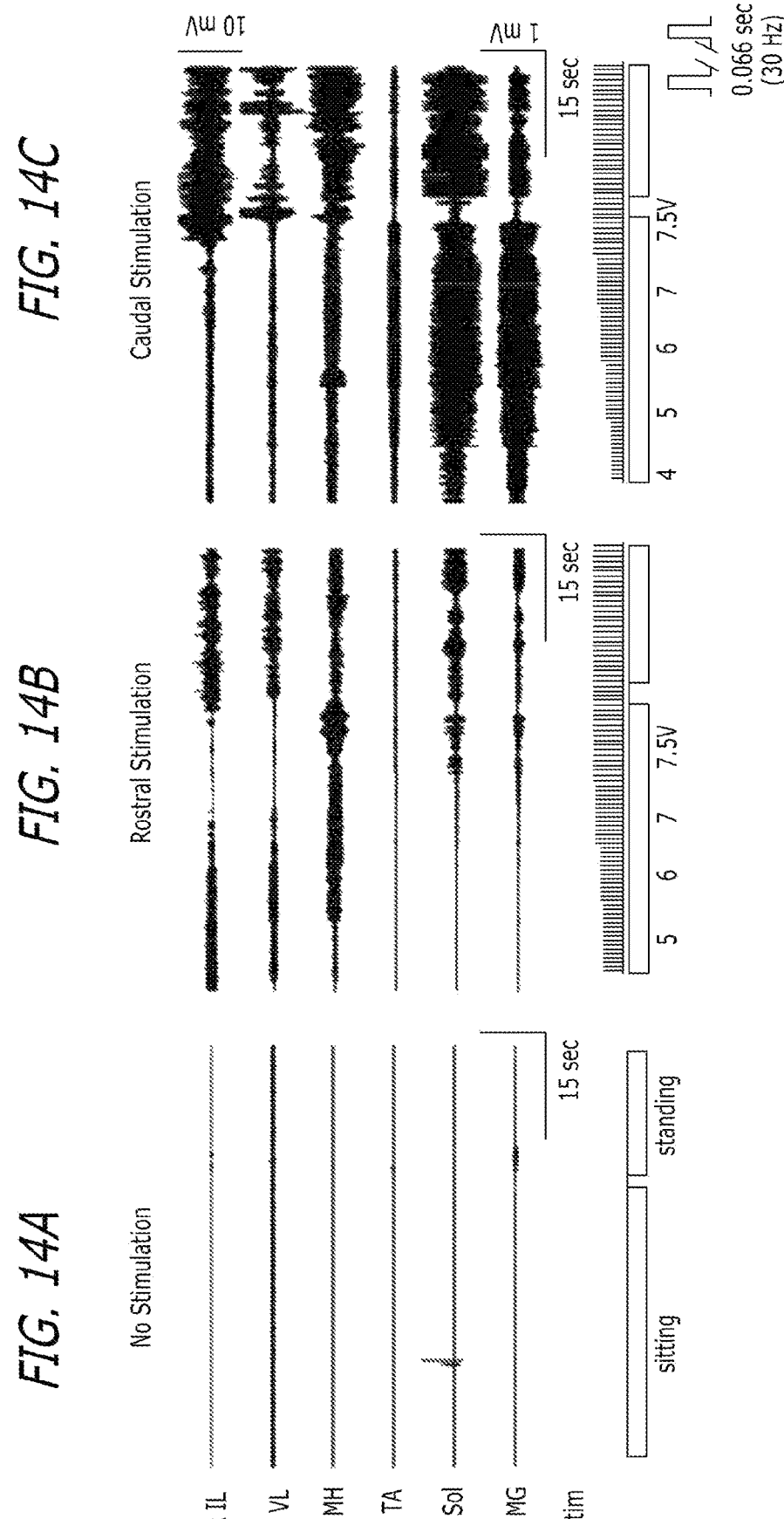
Figure 14E:
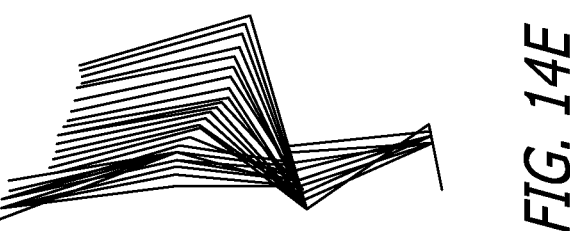
Figure 14D:
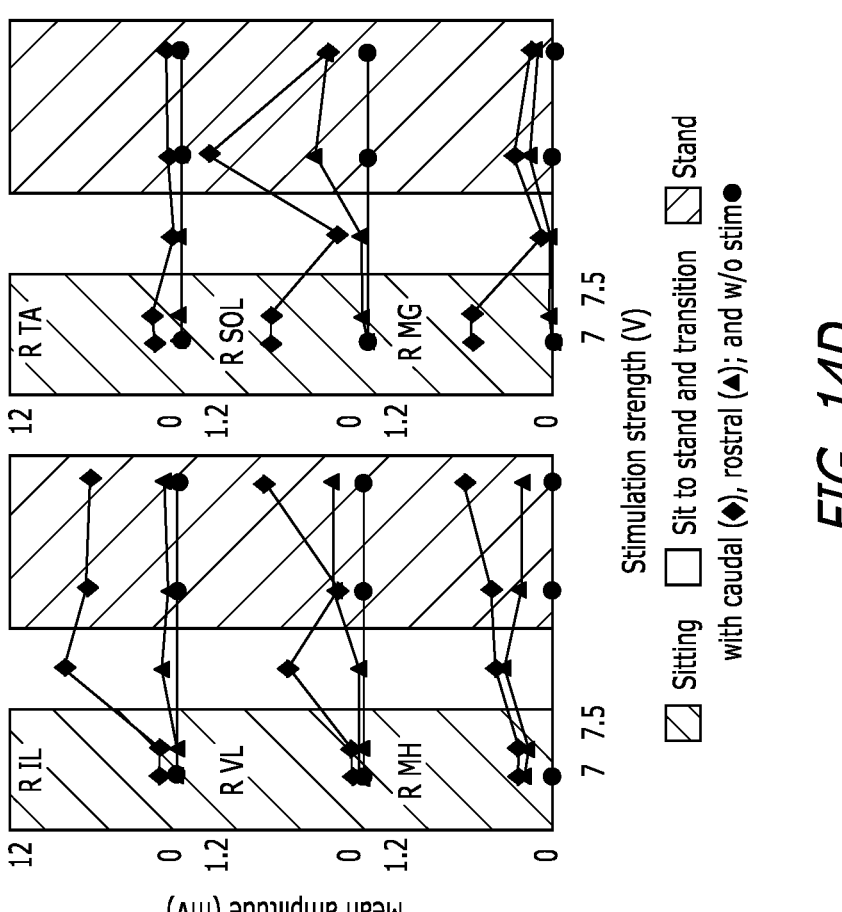

FIG. 14 illustrates lower extremity EMG activity during sitting and standing with and without epidural stimulation. There was little or no EMG activity without stimulation, but with epidural stimulation there was significant EMG activity that was modulated during the transition from sitting to standing. Panel A: EMG activity during sitting (green) and standing (yellow) with no epidural stimulation. Panel B: EMG activity during sitting (green) and standing (yellow) with 4V to 7.5 V, 15 Hz stimulation of the rostral lumbar segments (0/5/11–: Jan. 6, 2012+). Panel C: EMG activity during sitting (green) and standing (yellow) with epidural stimulation (15 Hz) of the caudal lumbosacral segments (4/10/15–: Mar. 9, 2014+). Panel D: Averaged mean amplitude (mV) of right side motor evoked responses during sitting and standing elicited from epidural stimulation (b) or rostal stimulation is represented by "▲" (c) or caudal stimulation is represented by "," and no stimulation is represented by opened circles (o). No stimulation values are only shown for sitting and standing. Panel E: Kinematic representation of transition from sitting to standing with caudal stimulation. Muscles: iliopsoas (IL), vastus lateralis (VL), medial hamstrings (MH), tibialis anterior (TA), soleus (Sol), and medial gastrocnemius (MO). Left side muscles (L), right side muscles (R).

Figure 15A:
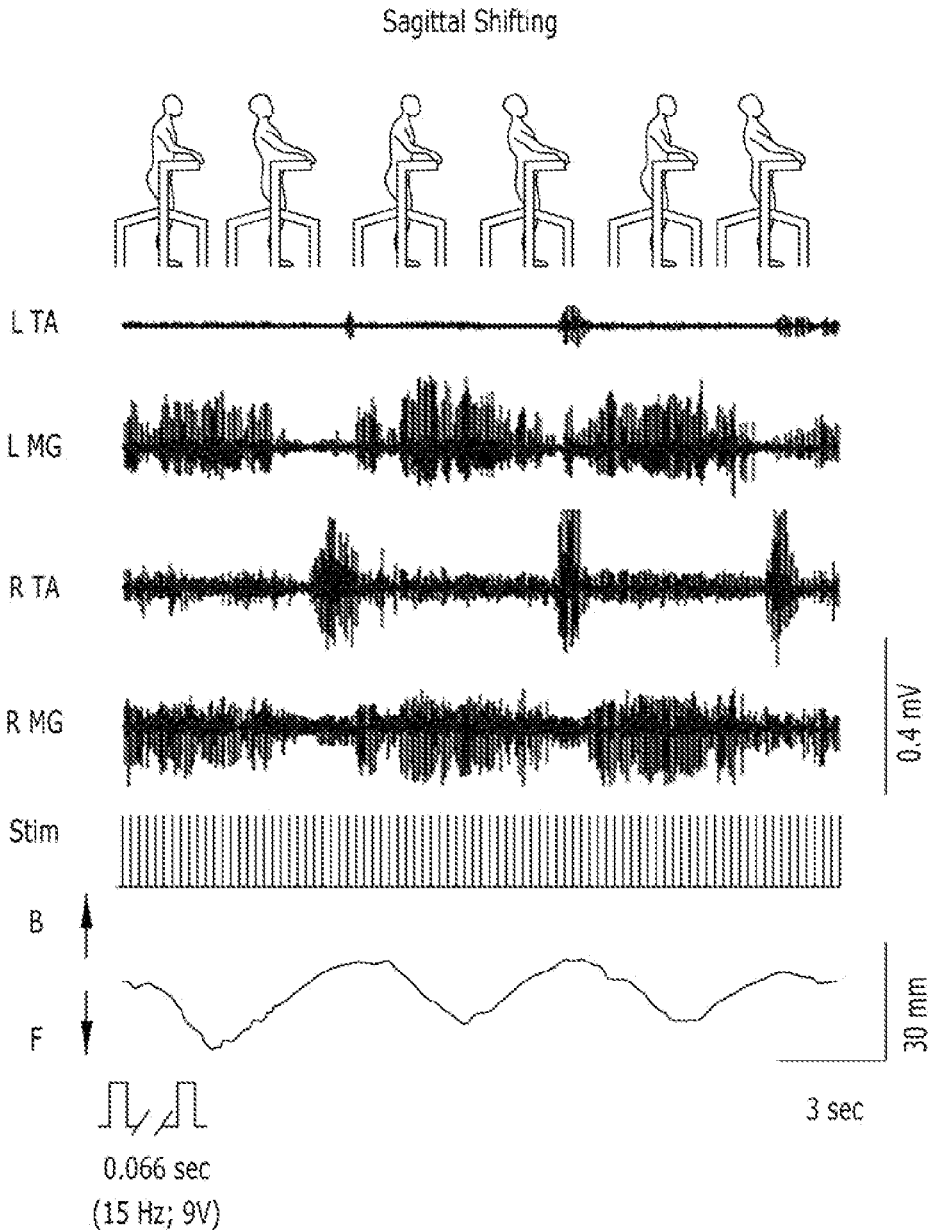
Figure 15B:
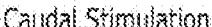
Figure 16B:
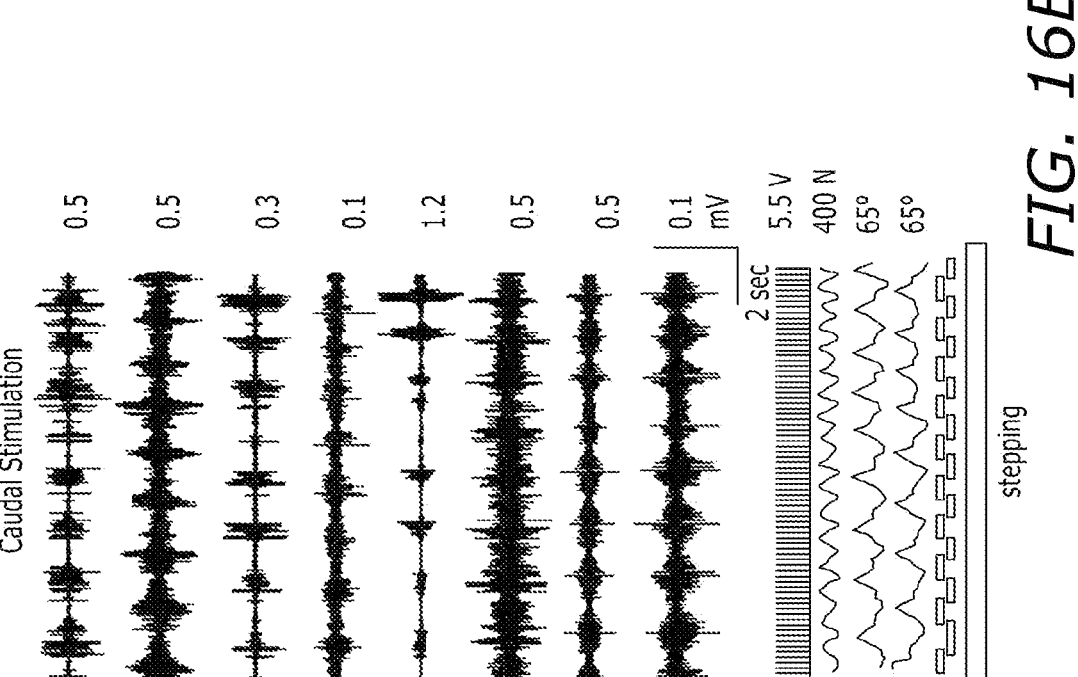
Figure 16A:
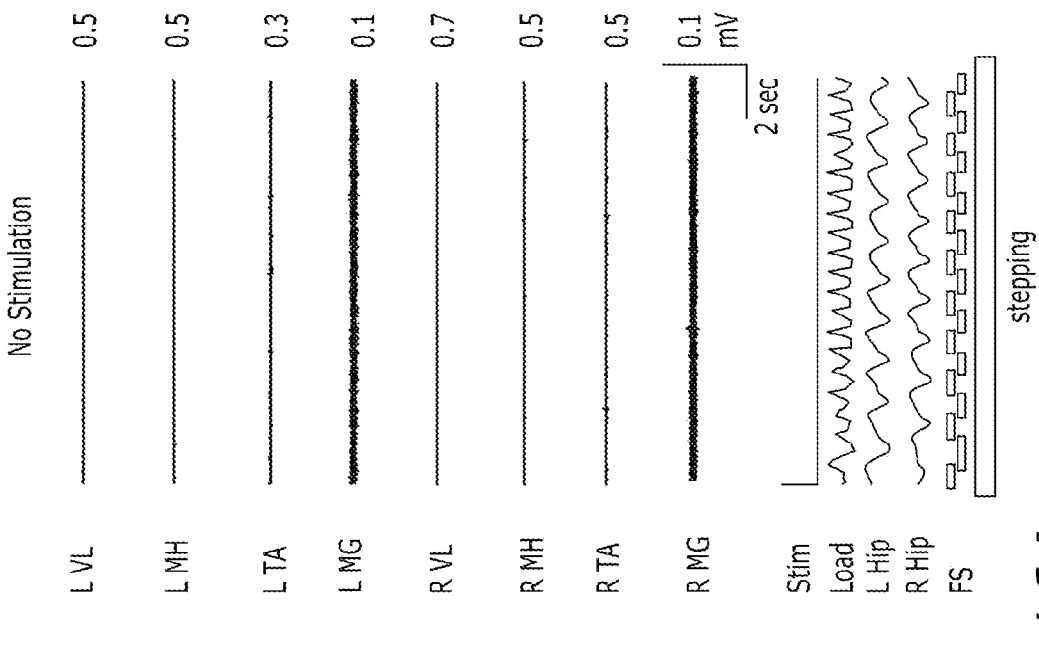
Figure 16D:
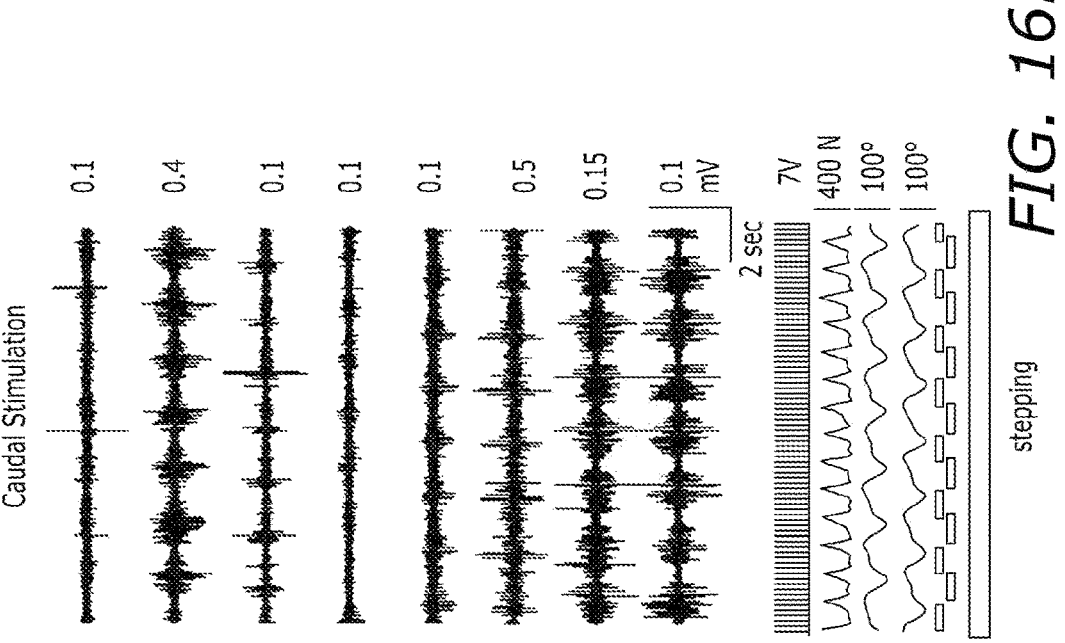
Figure 16C:
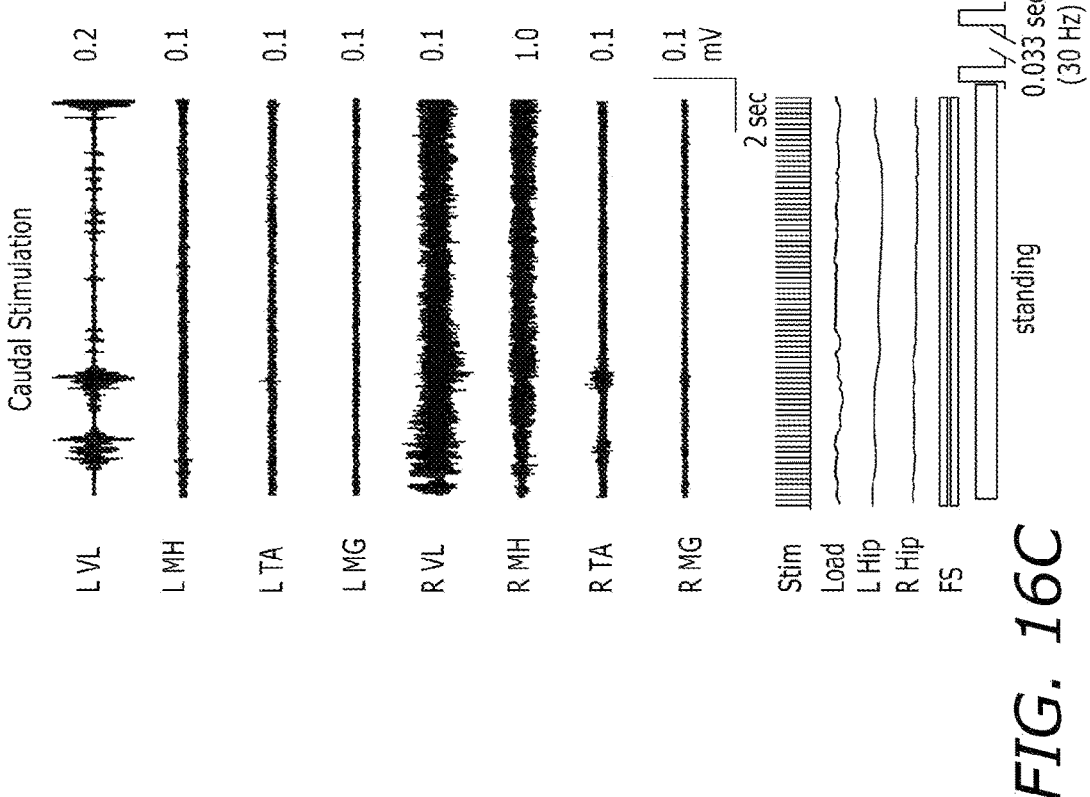

FIG. 15 illustrates EMG activity with epidural stimulation during independent standing. Panel A: EMG activity with epidural stimulation (8 V, 15 Hz) of the caudal lumbosacral segments (4/10/15–: Mar. 9, 2014+) during weight shifting.

Body movements are depicted in the top panel as displacement of the center of gravity (CGX) lateral shifting (CGY) to the right (R)) and left (L) sides in the bottom panels. Panel B: EMG activity with epidural stimulation during independent standing. Interpulse interval depicting stimulation frequency is shown on the lower right of the top and bottom graphs. Red line indicates initiation of independent standing as subject counted backwards from 3, blue line indicates when independent standing was obtained. Muscle: iliopsoas (IL), rectus femoris (RF), medial hamstrings (MH), tibialis anterior (TA), Soleus (SOL) and medial gastrocnemius (MG). Left (L) and right (R).

FIG. 16 shows lower extremity EMG activity during standing and stepping with body weight support and manual facilitation with and without epidural stimulation of caudal lumbosacral segments. The EMG patterns were modified by the intensity of stimulation and by different patterns of sensory input. EMG activity during stepping (50% BWS, 1.07 m/s) (panel A) without stimulation and (panel B) (45% BWS, 0.8 m/s) with epidural stimulation (5.5 V, 30 Hz) of caudal lumbosacral segments (4/10/15–: 3/9+). EMG activity during (panel C) standing (25% BWS) and (panels B, D) stepping (50% BWS, 1.07 m/s) with epidural stimulation (7.0 V, 30 Hz) of caudal lumbosacral segments (4/10/15–: 3/9+) (panel C). For stepping (panels B, C, and D) data were selected from 5 consecutive cycles. Muscles: vastus lateralis (VL), medial hamstrings (MH), tibialis anterior (TA), and medial gastrocnemius (MG). Left (L) and right (R) side muscles. Load is load cell reading in Newtons (N). Left (LHip) and Right (RHip) are sagittal joint angles for the hip joint. Left (LFS) and right (RFS) footswitches reflect stance phase.

Figure 17A:
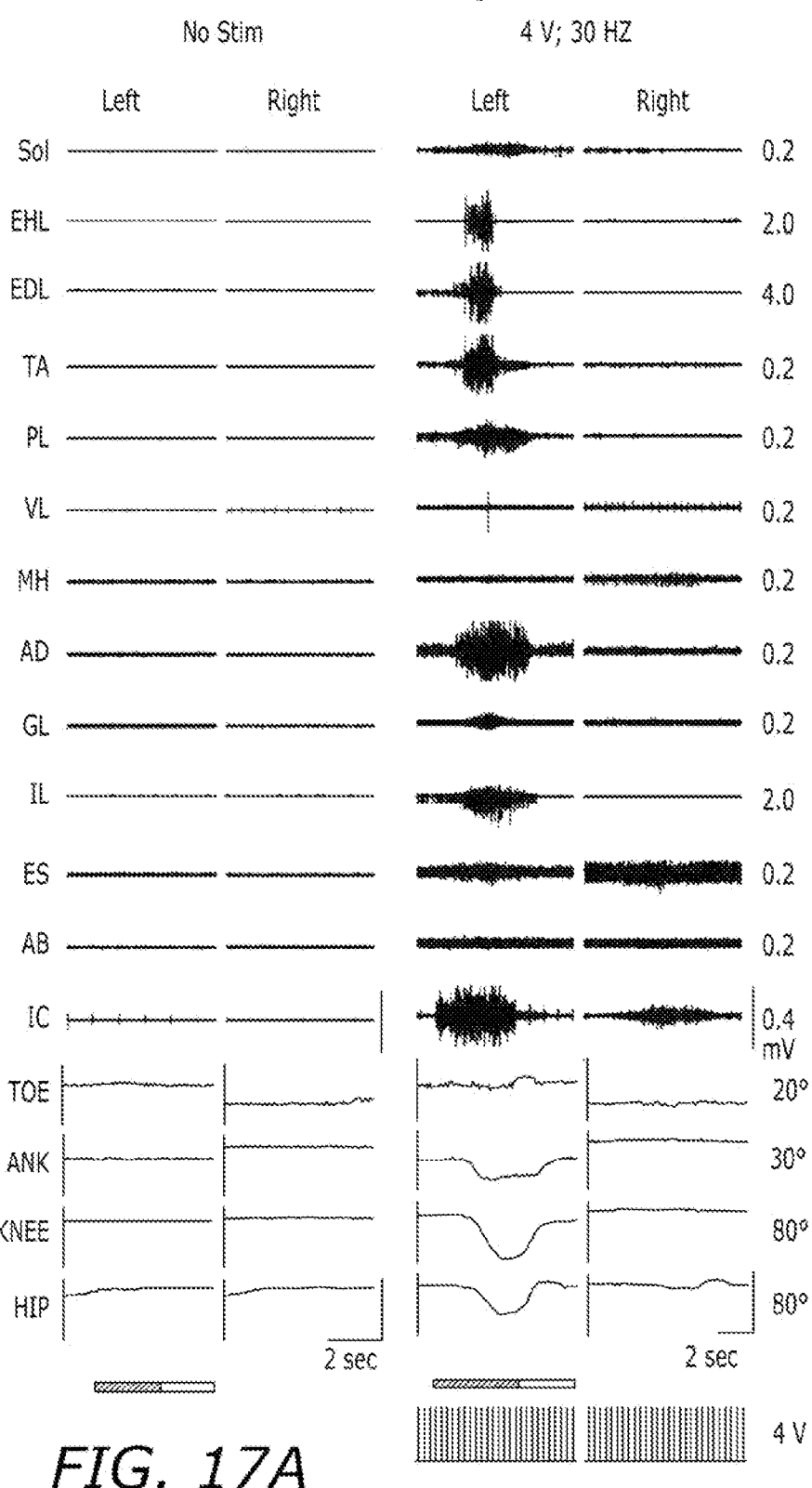
Figure 17B:
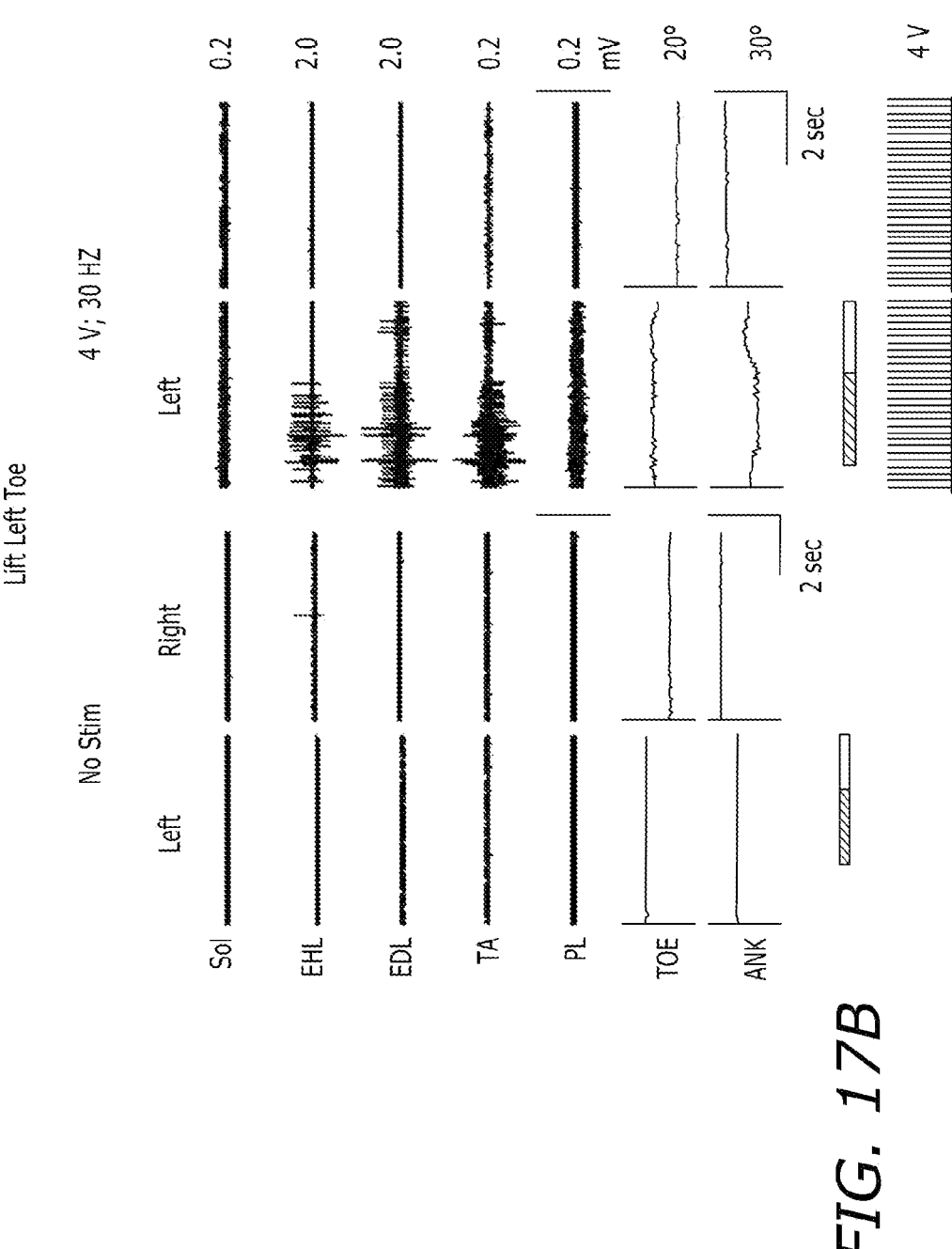
Figure 17C:
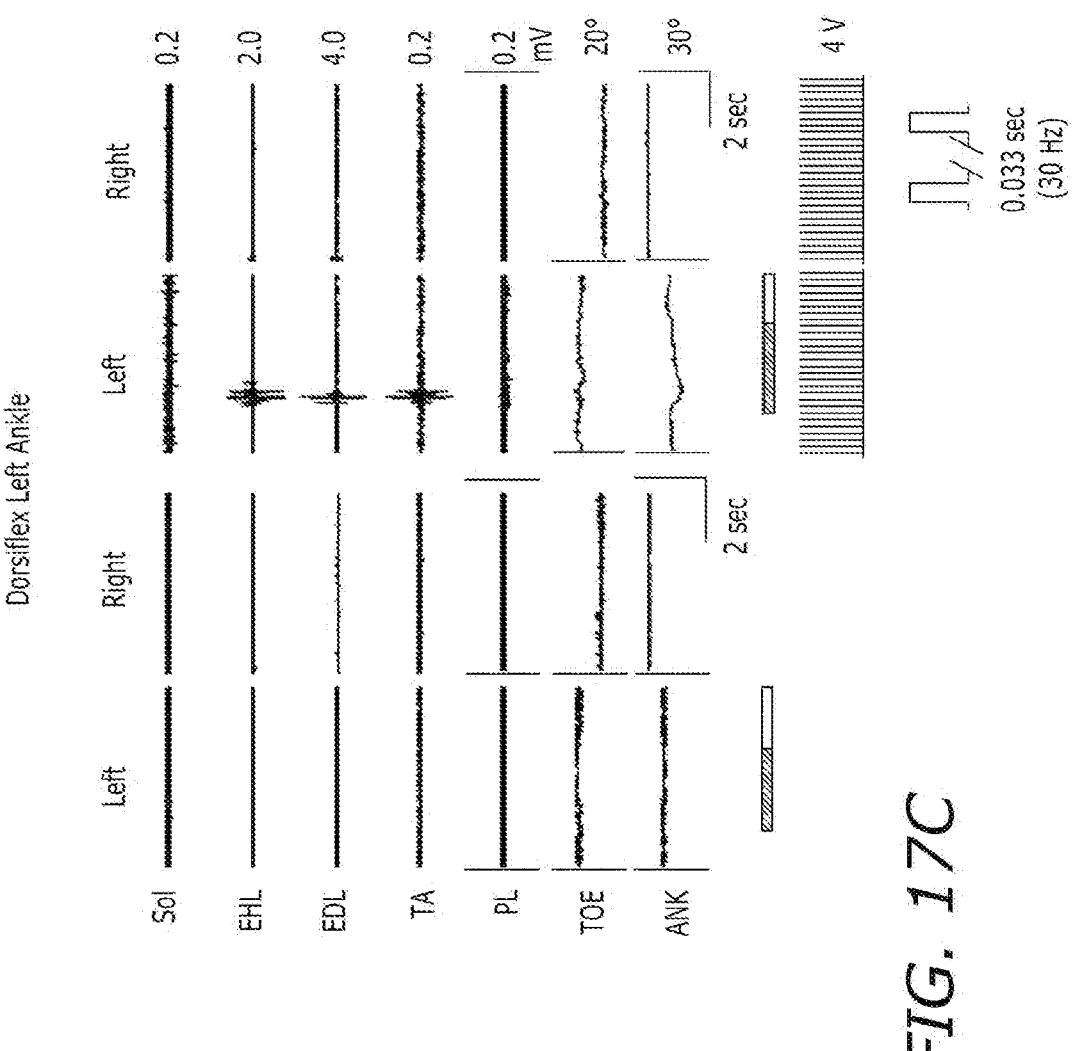
Figure 17D:
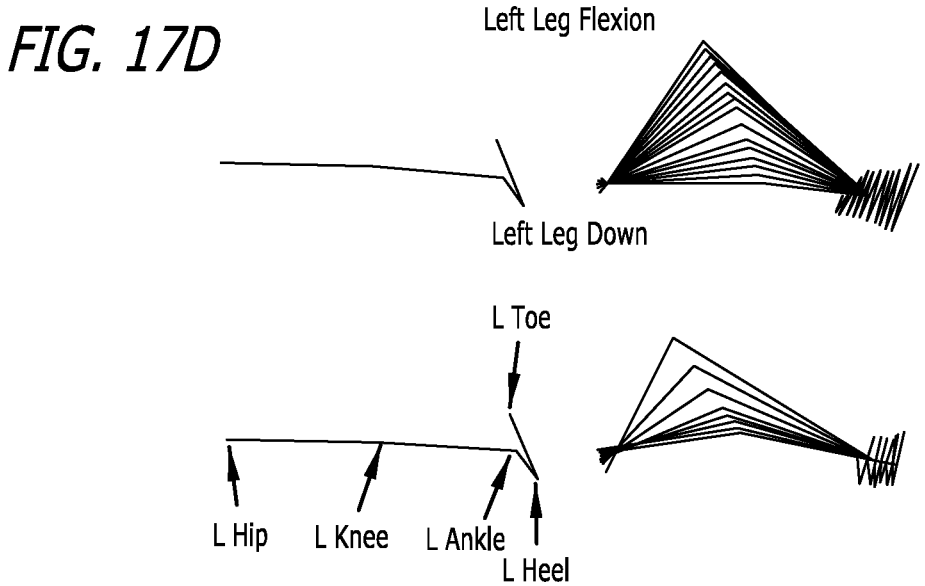
Figure 17E:
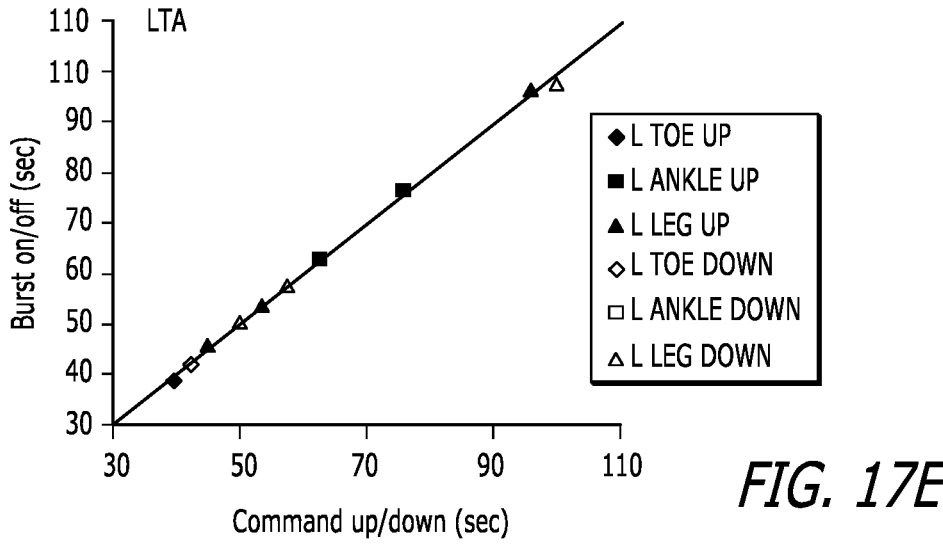

FIGS. 17A-17E show lower extremity EMG activity during voluntary control in a supine position with and without stimulation. The black bar indicates the command to generate flexion and move the left leg up (FIG. 17A), left ankle dorsiflexion (FIG. 17B), and left toe extension (FIG. 17C), and the white bar indicates the command to relax the leg. Left and right sides are shown to emphasize the isolated control of the left side following the command. The right and left intercostals (IC) are activated during the voluntary attempt of the leg, as the subject inhales as he attempts to perform the movement. Muscles: soleus (SOL), extensor digitorum longus (EDL), extensor hallucis longus (EHL), tibialis anterior (TA), peroneus longus (PL), vastus lateralis (VL), medial hamstrings (MH), adductor magnus (AD), gluteus maximus (GL), iliopsoas (IL), erector spinae (ES), rectus abdominus (AB), intercostals (IC). Sagittal joint angles for the toe (1st metatarsal relative to foot), ankle, knee, and hip joints. FIG. 17D: Stick figures were generated from the kinematics during the up and down commands for both trials with and without epidural stimulation. FIG. 17E: Relationship between onset (solid)/offset (open) of EMG burst for TA muscle and command up/down. Three trials were performed for the toe and leg voluntary movements and two trials for the ankle. All commands were given to move the left leg. The dotted line represents the line of identity (x=y).

Figure 18A:
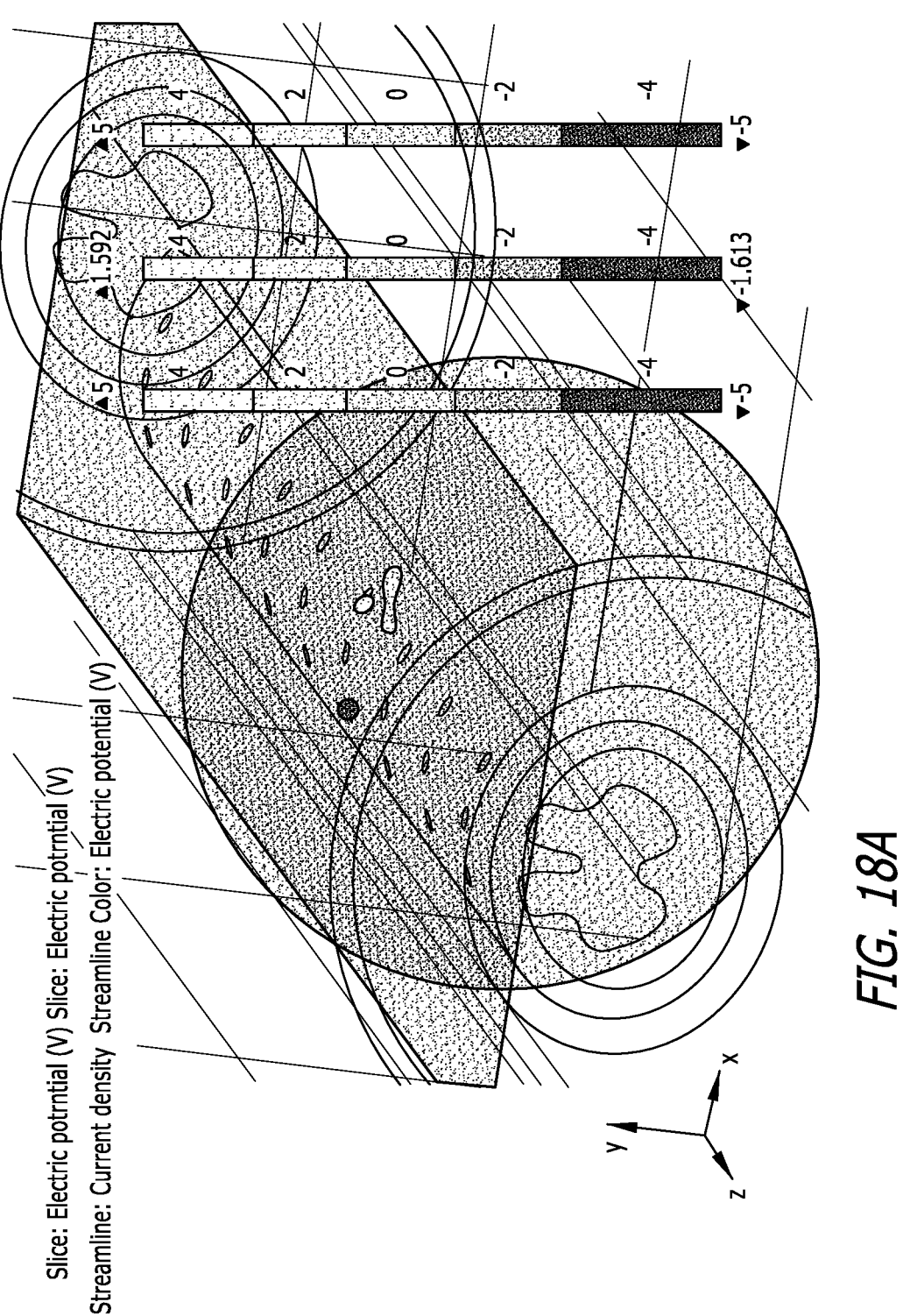

FIG. 18A shows a 3D view of epidural spinal electrode (with 2 of 27 electrodes activated) placed in the epidural space of a simulated spinal cord.

Figure 18B:
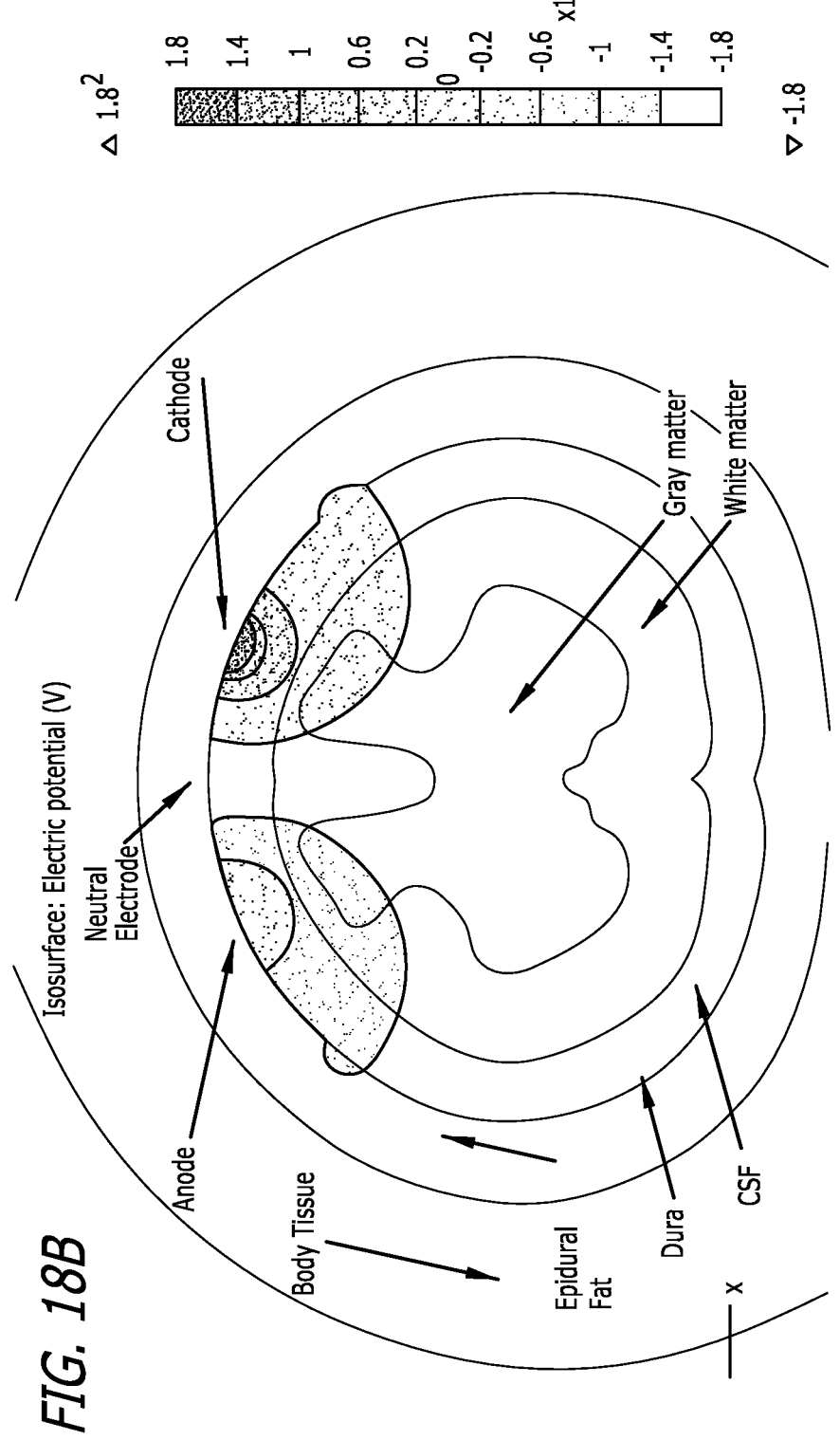

FIG. 18B shows isopotential contours of electrical field (in slice through center of bipolarly activated electrodes). Model compartments include gray matter, white matter, CSF, epidural fat, and surrounding body tissue.

Figure 19A:
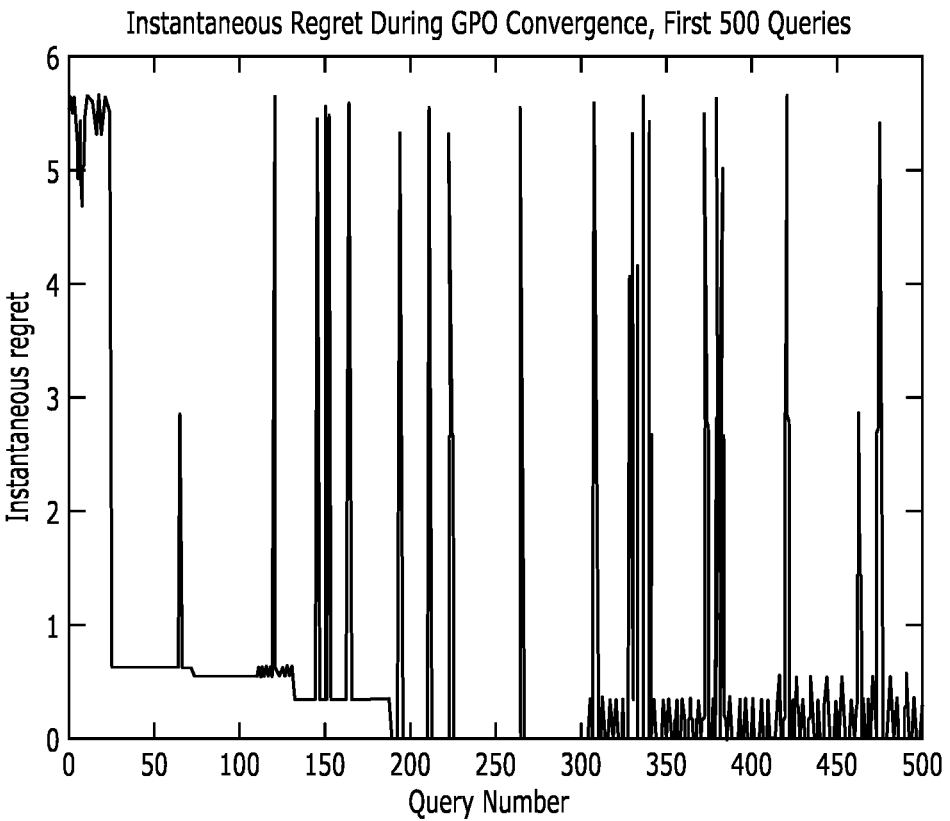
Figure 19B:
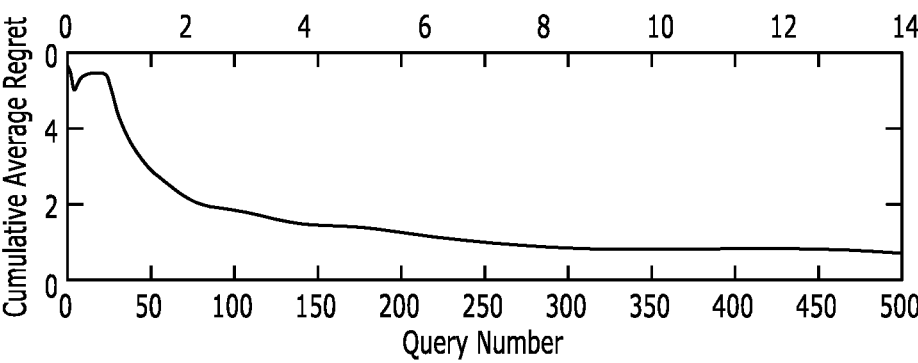

FIG. 19 (top) shows instantaneous regret (a measure of machine learning error) vs. learning iteration (labeled as "query number") for Gaussian Process Optimization of array stimulation parameters in the simulated spinal cord of FIGS. 18A and 18B. The "bursts" of poor performance corresponds to excursions of the learning algorithm to regions of parameter space that are previously unexplored, but which are found to have poor performance. FIG. 19 (bottom) shows the average cumulative regret vs. learning iteration. The average cumulative regret is a smoothed version of the regret performance function which better shows the algorithm's overall progress in selecting optimal stimulation parameters.

DETAILED DESCRIPTION OF THE INVENTION

Unless defined otherwise, technical and scientific terms used herein have the same meaning as commonly understood by one of ordinary skill in the art to which this invention belongs.

The term "motor complete" when used with respect to a spinal cord injury indicates that there is no motor function below the lesion, (e.g., no movement can be voluntarily induced in muscles innervated by spinal segments below the spinal lesion (e.g., as described below in Example 1).

The term "bipolar stimulation" refers to stimulation between two closely spaced electrodes.

The term "monopolar stimulation" refers to stimulation between a local electrode and a common distant return electrode.

The term "autonomic function" refers to functions controlled by the peripheral nervous system that are controlled largely below the level of consciousness, and typically involve visceral functions. Illustrative autonomic functions include, but are not limited to control of bowel, bladder, and body temperature.

The term "sexual function" refers to the ability to sustain a penile erection, have an orgasm (male or female), generate viable sperm, and/or undergo an observable physiological change associated with sexual arousal.

The term "cognitive function" refers to awareness of one's surrounding environment and the ability to function effectively, behaviorally, and mentally in a given environment.

In various embodiments, methods, devices, and optional pharmacological agents are provided to facilitate movement in a mammalian subject (e.g., a human) having spinal cord injury, brain injury, or other neurological disease or injury. In certain embodiments, the methods involve stimulating the spinal cord of the subject using an electrode array where the stimulation modulates the electrophysiological properties of selected spinal circuits in the subject so they can be activated by proprioceptive derived information and/or input from supraspinal. In various embodiments, the stimulation is typically accompanied by physical training (e.g., movement) of the region where the sensory-motor circuits of the spinal cord are located.

In particular illustrative embodiments, the devices, optional pharmacological agents, and methods described herein stimulate the spinal cord with, e.g., electrode arrays, that modulate the proprioceptive and supraspinal information which controls the lower limbs during standing and/or stepping and/or the upper limbs during reaching and/or grasping conditions. It is the sensory information that guides the activation of the muscles in a coordinated manner and in a manner that accommodates the external conditions, e.g., the amount of loading, speed, and direction of stepping or whether the load is equally dispersed on the two lower limbs, indicating a standing event, alternating loading indicating stepping, or sensing postural adjustments signifying the intent to reach and grasp.

Unlike approaches that involve specific stimulation of motor neurons to directly induce a movement, the methods described herein enable the spinal circuitry to control the movements. More specifically, the devices, optional pharmacological agents, and methods described herein exploit the spinal circuitry and its ability to interpret proprioceptive information and to respond to that proprioceptive information in a functional way. In various embodiments, this is in contrast to other approaches where the actual movement is induced/controlled by direct stimulation (e.g., of particular motor neurons).

In one illustrative embodiment, the subject is fitted with one or more implantable electrode arrays that afford selective stimulation and control capability to select sites, mode(s), and intensity of stimulation via electrodes placed epidurally over, for example, the lumbosacral spinal cord and/or cervical spinal cord to facilitate movement of the arms and/or legs of individuals with a severely debilitating neuromotor disorder.

The subject receives the implant (a standard procedure when used for pain alleviation), and typically about two weeks post implant, the subject is tested to identify the most effective subject specific stimulation paradigms for facilitation of movement (e.g., stepping and standing and/or arm and/or hand movement). Using these stimulation paradigms, the subject practices standing and stepping and/or reaching or grabbing in an interactive rehabilitation program while being subject to spinal stimulation.

Depending on the site/type of injury and the locomotor activity it is desired to facilitate, particular spinal stimulation protocols include, but are not limited to specific stimulation sites along the lumbosacral and/or cervical spinal cord; specific combinations of stimulation sites along the lumbosacral and/or cervical spinal cord; specific stimulation amplitudes; specific stimulation polarities (e.g., monopolar and bipolar stimulation modalities); specific stimulation frequencies; and/or specific stimulation pulse widths.

In various embodiments, the system is designed so that the patient can use and control it in the home environment.

In various embodiments, the approach is not to electrically induce a walking pattern or standing pattern of activation, but to enable/facilitate it so that when the subject manipulates their body position, the spinal cord can receive proprioceptive information from the legs (or arms) that can be readily recognized by the spinal circuitry. Then, the spinal cord knows whether to step or to stand or to do nothing. In other words, this enables the subject to begin stepping or to stand or to reach and grasp when they choose after the stimulation pattern has been initiated.

Moreover, as demonstrated in Example 1 (described below), the methods and devices described herein are effective in a spinal cord injured subject that is clinically classified as motor complete; that is, there is no motor function below the lesion. In various embodiments, the specific combination of electrodes activated/stimulated within an array and/or the desired stimulation of any one or more electrodes and/or the stimulation amplitude (strength) can be varied in real time, e.g., by the subject. Closed loop control can be embedded in the process by engaging the spinal circuitry as a source of feedback and feedforward processing of proprioceptive input and by voluntarily imposing fine tuning modulation in stimulation parameters based on visual, and/or kinetic, and/or kinematic input from selected body segments.

In various embodiments, the devices, optional pharmacological agents, and methods are designed so that a subject with no voluntary movement capacity can execute effective standing and/or stepping and/or reaching and/or grasping. In addition, the approach described herein can play an important role in facilitating recovery of individuals with severe although not complete injuries.

The approach described herein can provide some basic postural, locomotor and reaching and grasping patterns on their own. However, they are also likely to be a building block for future recovery strategies. Based on certain successes in animals and some preliminary human studies (see below), it appears that a strategy combining effective epidural stimulation of the appropriate spinal circuits with physical rehabilitation and pharmacological intervention can provide practical therapies for complete SCI human patients. There is sufficient evidence from our work that such an approach should be enough to enable weight bearing standing, stepping and/or reaching or grasping. Such capability can give complete SCI patients the ability to participate in exercise, which is known to be highly beneficial for their physical and mental health. We also expect our method should enable movement with the aid of assistive walkers. While far from complete recovery of all movements, even simple standing and short duration walking would increase these patients' autonomy and quality of life. The stimulating array technology described herein (e.g., epidural stimulating arrays) paves the way for a direct brain-to-spinal cord interface that could enable more lengthy and finer control of movements.

While the methods and devices described herein are discussed with reference to complete spinal injury, it will be recognized that they can apply to subjects with partial spinal injury, subjects with brain injuries (e.g., ischemia, traumatic brain injury, stroke, and the like), and/or subjects with neurodegenerative diseases (e.g., Parkinson's disease, Alzheimer's disease, Huntington's disease, amyotrophic lateral sclerosis (ALS), primary lateral sclerosis (PLS), cerebral palsy, and the like).

In various embodiments, the methods combine the use of epidural stimulating arrays with physical training (e.g., rigorously monitored (robotic) physical training), optionally in combination with pharmacological techniques. The methods enable the spinal cord circuitry to utilize sensory input as well as newly established functional connections from the brain to circuits below the spinal lesion as a source of control signals. The approach is thus designed to enable and facilitate the natural sensory input as well as supraspinal connections to the spinal cord in order to control movements, rather than induce the spinal cord to directly induce the movement. That is, we facilitate and enhance the intrinsic neural control mechanisms of the spinal cord that exist post-SCI, rather than replace or ignore them.

Processing of Sensory Input by the Lumbosacral Spinal Cord: Using Afferents as a Source of Control In various embodiments the methods and devices described herein exploit spinal control of locomotor activity. For example, the human spinal cord can receive sensory input associated with a movement such as stepping, and this sensory information can be used to modulate the motor output to accommodate the appropriate speed of stepping and level of load that is imposed on lower limbs. Moreover, we have demonstrated that the human lumbosacral spinal cord has central-pattern-generation-like properties. Thus, oscillations of the lower limbs can be induced simply by vibrating the vastus lateralis muscle of the lower limb, by epidural stimulation, and by stretching the hip. The methods described herein exploit the fact that the human spinal cord, in complete or incomplete SCI subjects, can receive and interpret proprioceptive and somatosensory information that can be used to control the patterns of neuromuscular activity among the motor pools necessary to generate particular movements, e.g., standing, stepping, reaching, grasping, and the like. The methods described herein facilitate and adapt the operation of the existing spinal circuitry that generates, for example, cyclic step-like movements via a combined approach of epidural stimulation, physical training, and, optionally, pharmacology.

Facilitating Stepping and Standing in Humans Following a Clinically Complete Lesion Locomotion in mammals is attributed to intrinsic oscillating spinal neural networks capable of central pattern generation interacting with sensory information (Edgerton et al., *J. American Paraplegia Soc,* 14(4) (1991), 150-157; Forssberg, *J. Neurophysiol,* 42(4): 936-953 (1979); *Grillner and Wallen, Annu. Rev. Neurosci.,* 8:233-261 (1985); Grillner and Zangger, *Exp Brain Res,* 34 (2): 241-261 (1979)). These networks play critical roles in generating the timing of the complex postural and rhythmic motor patterns executed by motor neurons.

As indicated above, the methods described herein can involve stimulation of one or more regions of the spinal cord in combination with locomotory activities. It was our discovery that spinal stimulation in combination with locomotor activity results in the modulation of the electrophysiological properties of spinal circuits in the subject so they are activated by proprioceptive information derived from the region of the subject where locomotor activity is to be facilitated. Further, we also determined that spinal stimulation in combination with pharmacological agents and locomotor activity results in the modulation of the electrophysiological properties of spinal circuits in the subject so they are activated by proprioceptive information derived from the region of the subject where locomotor activity is to be facilitated.

Locomotor activity of the region of interest can be accomplished by any of a number of methods known, for example, to physical therapists. By way of illustration, individuals after severe SCI can generate standing and stepping patterns when provided with body weight support on a treadmill and manual assistance. During both stand and step training of human subjects with SCI, the subjects can be placed on a treadmill in an upright position and suspended in a harness at the maximum load at which knee buckling and trunk collapse can be avoided. Trainers positioned, for example, behind the subject and at each leg assist as needed in maintaining proper limb kinematics and kinetics appropriate for each specific task. During bilateral standing, both legs can be loaded simultaneously and extension can be the predominant muscular activation pattern, although co-activation of flexors can also occur. Additionally, or alternatively, during stepping the legs are loaded in an alternating pattern and extensor and flexor activation patterns within each limb also alternated as the legs moved from stance through swing. Afferent input related to loading and stepping rate can influence these patterns, and training has been shown to improve these patterns and function in clinically complete SCI subjects.

Epidural Stimulation of the Lumbosacral Spinal Cord

As indicated above, without being bound by a particular theory, it is believed that epidural stimulation, e.g., over the lumbosacral spinal cord in combination with physical training can facilitate recovery of stepping and standing in human subjects following a complete SCI.

Spinal cord electrical stimulation has been successfully used in humans for suppression of pain and spasticity (see, e.g., Johnson and Burchiel, *Neurosurgery,* 55(1): 135-141 (2004); discussion 141-142; Shealy et al., *Anesth Analg,* 46(4): 489-491 (1967); Campos et al., *Appl. Neurophysiol.* 50(1-6): 453-454 (1987); Dimitrijevic and Sherwood, *Neurology,* 30 (7 Pt 2): 19-27 (1980); Barolat *Arch. Med. Res.,* 31 (3): 258-262 (2000); Barolat, *J. Am. Paraplegia Soc.,* 11(1): 9-13 (1988); Richardson et al., *Neurosurgery,* 5 (3): 344-348). Recent efforts to optimize electrode design and stimulation parameters have led to a number of research studies focusing on the benefits of epidural spinal cord stimulation. We have demonstrated that the location of the electrode array and its stimulation parameters are important in defining the motor response. Use of high density electrode arrays, as described herein, facilitates selection or alteration of particular stimulation sites as well as the application of a wide variety of stimulation parameters.

Figure 1:
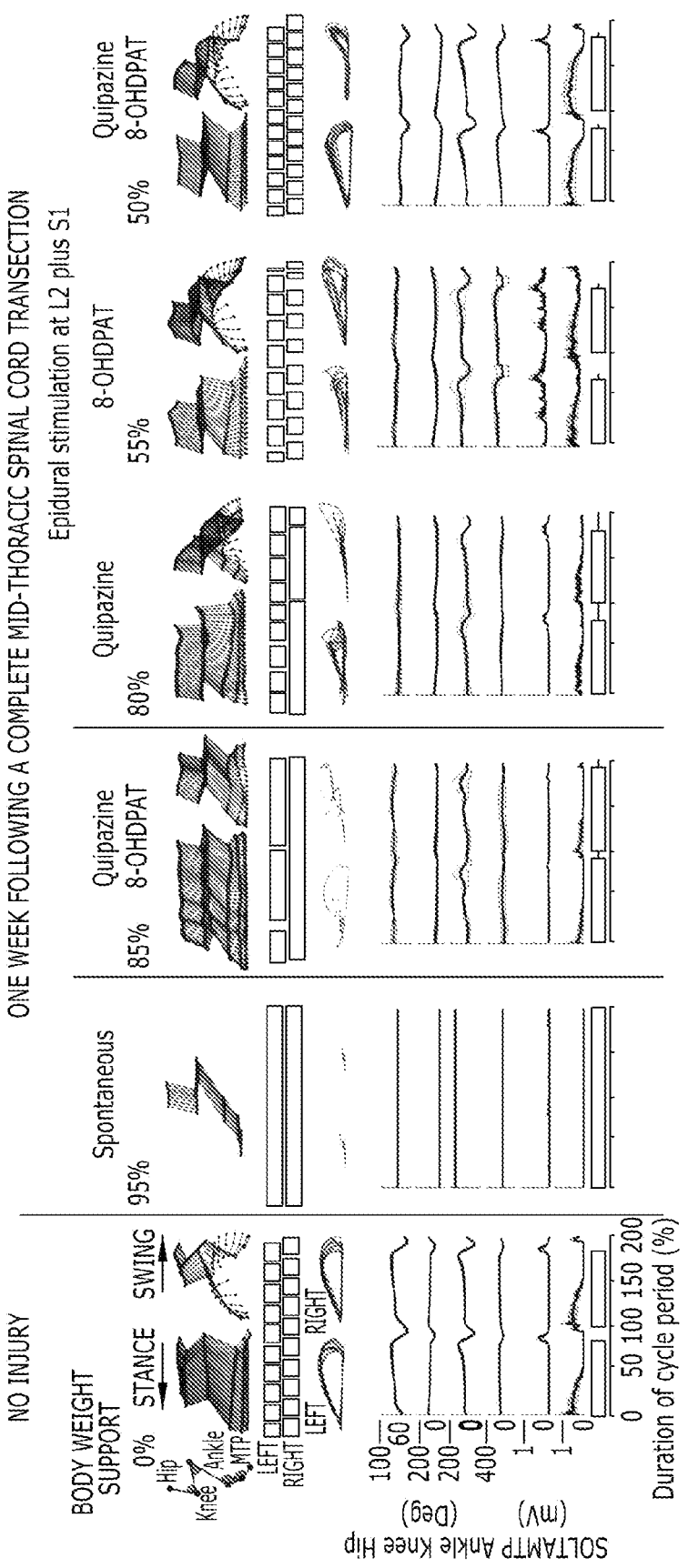

FIG. 1 summarizes experiments in rats that were carried out to assess the effectiveness of epidural stimulation coupled with combined drug therapy in acute treatment of complete spinal cord injury. These experiments also show that pharmacological intervention provides some recovery of stepping function, but that epidural stimulation coupled with drug therapy recovers significant amounts of stepping ability even one week after a complete spinal transaction.

Figure 2:
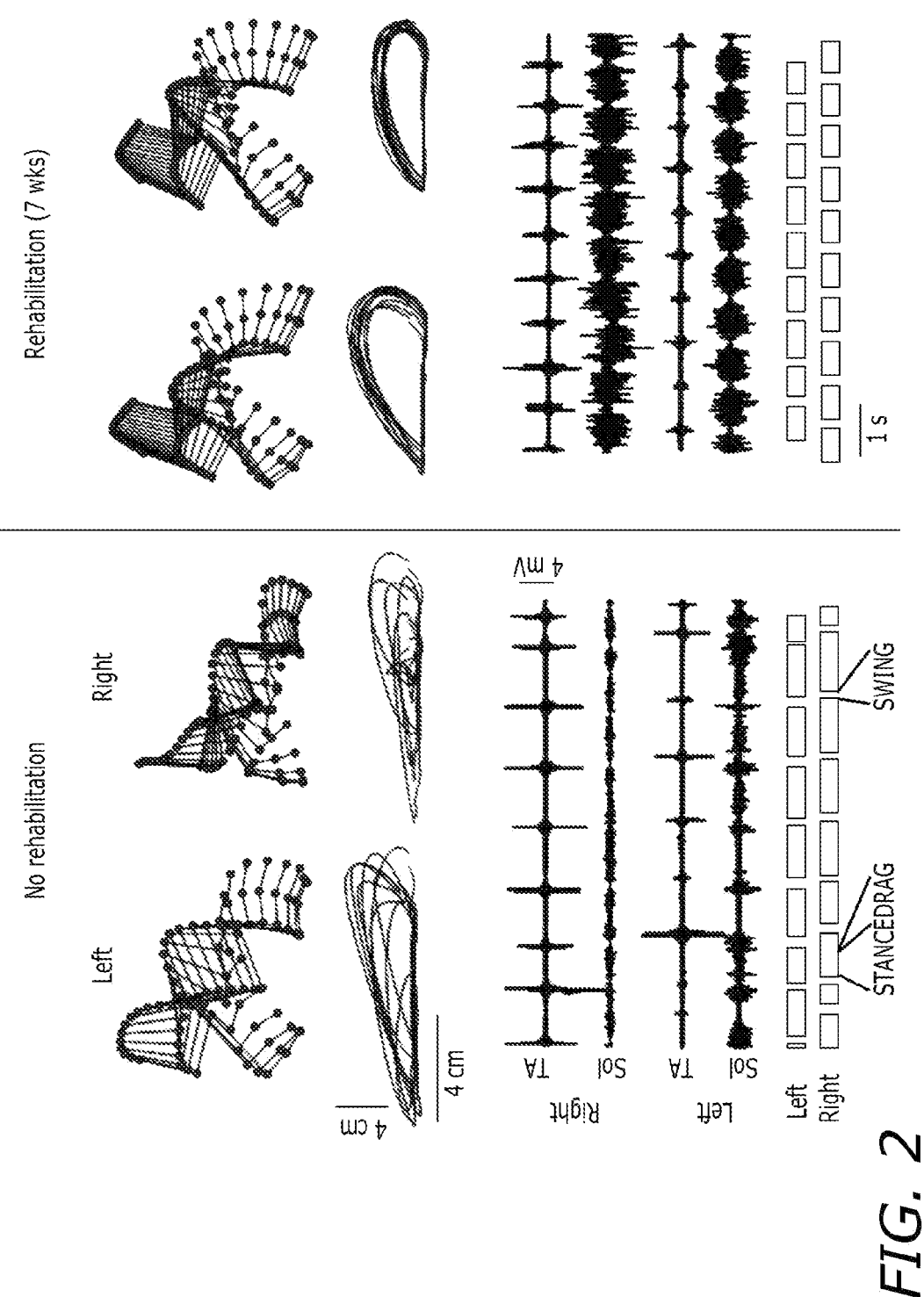

FIG. 2 compares two adult rats with complete spinal cord transections at the end of a 7 week period during which both animals were given both drug therapy as well as epidural stimulation (using conventional rod-electrodes at two spinal sites). The animal which was also given robotically guided physical therapy showed significant improvement over the animal which did not receive physical training. These results provide support for our assertion that a strategy that combines physical therapy with epidural stimulation and, optional, pharmacological modulation of the post-SCI spinal circuits can facilitate standing and stepping recovery in humans.

MicroFabricated High-Density Epidural Stimulating Arrays

In various embodiments, the epidural electrical stimulation is administered via a high density epidural stimulating array. In certain embodiments, the high density electrode arrays use microfabrication technology to place numerous electrodes in an array configuration on a flexible substrate. One suitable epidural array fabrication method was first developed for retinal stimulating arrays (see, e.g., Maynard, *Annu. Rev. Biomed. Eng.,* 3:145-168 (2001); Weiland and Humayun, *IEEE Eng. Med. Biol. Mag.,* 24 (5): 14-21 (2005)), and U.S. Patent Publications 2006/0003090 and 2007/0142878 which are incorporated herein by reference for all purposes (e.g., the devices and fabrication methods disclosed therein). In various embodiments the stimulating arrays comprise one or more biocompatible metals (e.g., gold, platinum, chromium, titanium, iridium, tungsten, and/ or oxides and/or alloys thereof) disposed on a flexible material (e.g., parylene A, parylene C, parylene AM, parylene F, parylene N, parylene D, or other flexible substrate materials). Parylene has the lowest water permeability of available microfabrication polymers, is deposited in a uniquely conformal and uniform manner, has previously been classified by the FDA as a United States Pharmacopeia (USP) Class VI biocompatible material (enabling its use in chronic implants) (Wolgemuth, *Medical Device and Diagnostic Industry,* 22 (8): 42-49 (2000)), and has flexibility characteristics (Young's modulus ~4 GPa (Rodger and Tai, IEEE Eng. Med. Biology, 24 (5): 52-57 (2005))), lying in between those of PDMS (often considered too flexible) and most polyimides (often considered too stiff). Finally, the tear resistance and elongation at break of parylene are both large, minimizing damage to electrode arrays under surgical manipulation (Rodger et al., *Sensors and Actuators B-Chemical,* 117(1): 107-114 (2006)).

The electrode array may be implanted using any of a number of methods (e.g., a laminectomy procedure) well known to those of skill in the art. FIG. 3 shows a first prototype microelectrode array, scaled for mice, in which ten 250 micron diameter platinum electrodes are microfabricated onto a 2 mm wide Parylene backing. The electrodes are dorsally implanted using a laminectomy over the lumbosacral spinal cord, with one electrode placed over each intravertebral segment. In chronic implantation studies (using rat, mice, and pig animal models) of up to 6 months, we have shown high biocompatibility of these arrays with mammalian tissue. Implantation of an array into a human subject is described in Example 1.

Of course, other microarray embodiments are contemplated. In certain embodiments, the number of electrodes formed on an electrode array can vary from one electrode to about 100,000 electrodes or more. In certain embodiments, the electrode microarray comprises at least 10, at least 15, at least 20, at least 25, at least 50, at least 100, at least 250, at least 500, or at least 1000 electrodes. In various embodiments the interelectrode spacing of adjacent electrodes in the electrode array varies from about 100 µm or about 500 µm, or about 1000 µm or about 1500 µm to about 2000 µm, or about 3000 µm, or about 4000 µm, or about 4500 µm, or about 5000 µm. In various embodiments, interelectrode spaking ranges from about 100 µm, about 150 µm, about 200 µm, or about 250 µm up to about 1,000 µm, about 2000 µm, about 3000 µm, or about 4,000 µm. In various illustrative embodiments, individual electrode diameters (or width) range from about 50 µm, 100 µm, 150 µm, 200 µm, or 250 µm up to about 500 µm, about 1000 µm, about 1500 µm, or about 2000 µm.

The electrode array can be formed in any geometric shape such as a square or circular shape; typically the size of the array will be on the order of about 0.1 mm to about 2 cm, square or in diameter, depending in part on the number of electrodes in the array. In various embodiments, the length of an electrode array ranges from about 0.01 mmm, or 0.1 mm up to about 10 cm or greater.

In various embodiments, the arrays are operably linked to control circuitry that permits selection of electrode(s) to activate/stimulate and/or that controls frequency, and/or pulse width, and/or amplitude of stimulation. In various embodiments, the electrode selection, frequency, amplitude, and pulse width are independently selectable, e.g., at different times, different electrodes can be selected. At any time, different electrodes can provide different stimulation frequencies and/or amplitudes. In various embodiments, different electrodes or all electrodes can be operated in a monopolar mode and/or a bipolar mode, using constant current or constant voltage delivery of the stimulation.

In certain embodiments, the electrodes can also be provided with implantable control circuitry and/or an implantable power source. In various embodiments, the implantable control circuitry can be programmed/reprogrammed by use of an external device (e.g., using a handheld device that communicates with the control circuitry through the skin). The programming can be repeated as often as necessary.

FIG. 16 shows EMG responses from different muscle groups to different types of stimulation (monopolor and bipolar) at different spinal sites. These data show that our strategy of spatially selective epidural stimulation of different portions of the lumbosacral spinal cord can focally excite and coordinate the muscle groups that are involved in locomotion.

We have also developed and tested in rats more complex twenty-seven electrode arrays, which are arranged in a 9×3 pattern so that there are 3 electrodes (mid-line, left, and right) at each of 9 intravertebral segments (FIG. 7). These arrays have been tested for up to 6 weeks in vivo, showing biocompatibility as well as stepping capability that betters the previous results we have obtained with conventional electrodes. FIG. 8 shows a 256 electrode array that was fabricated to demonstrate the potential for multi-layer fabrication technology to build an array of hundreds of electrodes.

Embodiments of the electrode arrays described herein may be constructed to offer numerous advantages. For example, flexible parylene electrode arrays are mechanically stable. Their flexibility allows them to conform to the contours of the spinal cord, forming a thin layer (e.g., 10 μm thick) that adheres to the cord. This close fit facilitates connective tissue encapsulation, which also enhances fixation.

The arrays may also offer spatially selective stimulation. Early studies of stimulation protocols to facilitate locomotion in SCI animals delivered stimuli to a single spinal cord region as the ideal stimulation site was hypothesized to be fixed and species-specific. Researchers identified "optimal" stimulation sites for cats (Gerasimenko et al., *Neurosci. Behav. Physiol.*, 33 (3): 247-254 (2003)) and for rats (Gerasimenko et al., *J Neurosci. Meth.*, 157 (2): 253-263 (2006)) at a single time point after injury. However, the optimal stimulation site may not be constant. Rat studies showed that while stimulation at the L2 spinal level facilitated the best stepping soon after a complete transection, S1 stimulation produced more effective stepping several weeks later (Id.). Similarly, clinical data from patients receiving SCS for the treatment of lower back pain indicates that continued pain suppression often requires adjustment of the electrode position (Carter, Anaesth. Intensive Care, 32(1): 11-21 (2004)). These data support the hypothesis that the optimal stimulation pattern is not fixed. After a traumatic injury, the spinal cord is continuously modified by the progression of secondary damage, as well as the post-injury therapies. Our arrays' high electrode density enables ongoing identification of the optimal stimulation patterns. Our arrays' high-density allows adjustment of the stimulating pattern to account for migration, or for initial surgical misalignment.

The electrode arrays described herein also facilitate the use of advanced stimulation paradigms. Given the complex chain of reflexes involved, for example, in stepping, we believe that more sophisticated spatiotemporal stimulation patterns, involving either simultaneous or sequential stimulation of different spinal cord regions, may facilitate improved posture and locomotion and reaching and grasping compared with simple patterns. The high electrode densities allow us to test advanced stimulation paradigms that have previously been infeasible to study.

In addition, the electrode arrays provide for a lower charge injection amplitude and lower power consumption. The close positioning to the spinal cord possible with electrode arrays described herein minimizes the required levels of charge injection and power consumption. Since long-term tissue damage caused by electrical stimulation is proportional to injected charge, our conformal arrays allow longer sustained bouts of stimulation. This is desirable for long-term stimulation therapy and for battery-powered implants.

The electrode arrays described herein facilitate the measurement and evaluation of evoked potentials. Our electrode arrays can record field potentials from the dorsum (or other regions) of the spinal cord. Spinal somatosensory evoked potentials (SSEPs) measured from different levels of the spinal cord can be used to assess the state of the spinal cord and, potentially, to identify and classify the nature of a spinal injury. SSEPs are typically composed of a series of responses. With an array, response latency, amplitude, and conduction velocity can be simultaneously gathered from positions throughout the lumbosacral spinal cord. Examining the SSEPs for different injury types facilitates the generation of an injury-specific atlas of spinal potentials. SSEPs can be used as a measure of recovery and to evaluate the potential effectiveness of different treatment paradigms that might be applied. Monitoring SSEPs at different time points after the start of a treatment provides insight into the synaptic mechanisms that are involved in reacquiring locomotor function, and also serve as a diagnostic of how and if a particular strategy is aiding recovery. For example, recent data collected in our lab suggests that the return of polysynaptic spinal responses may be correlated with regaining the ability to step.

Use of Machine Learning to Select Optimal Electrode Array Stimulation Parameters High density epidural stimulating electrode arrays can provide patient-customized stimuli, compensate for errors in surgical placement of the array, and adapt the stimuli over time to spinal plasticity (changes in spinal cord function and connectivity). However, with this flexibility comes the burden of finding suitable stimuli parameters (e.g., the pattern of electrode array stimulating voltage amplitudes, stimulating currents, stimulating frequencies, and stimulating waveform shapes) within the vast space of possible electrode array operating patterns. It is not practical to exhaustively test all possible parameters within this huge space to find optimal parameter combinations. Such a process would consume a large amount of clinical resources. A machine learning algorithm can employed to more efficiently search for effective parameter combinations. Over time, a machine learning algorithm can also be used to continually, occasionally, and/or periodically adapt the stimulation operating parameters as needed.

A machine learning algorithm that seeks to optimize the stimuli parameters desirably alternates between exploration (searching the parameter space and building a regression model that relates stimulus and motor response) and exploitation (optimizing the stimuli patterns based on the current regression model). Many machine learning algorithms incorporate exploration and exploitation phases, and any learning algorithm that incorporates these two phases can be employed as a procedure to select (e.g., optimize) the electrode array stimulating parameters over time.

One particular embodiment relies upon Gaussian Process Optimization (GPO) (Rasmussen, Gaussian Processes for Machine Learning, MIT Press (2006)), an active learning method whose update rule explores and exploits the space of possible stimulus parameters while constructing an online regression model of the underlying mapping from stimuli to motor performance (e.g., stepping, standing, or arm reaching). Gaussian Process Regression (GPR), the regression modeling technique at the core of GPO, is well suited to online use because it requires fairly minimal computation to incorporate each new data point, rather than the extensive recomputation of many other machine learning regression of models lying within a restricted set, rather than from a single model, allowing it to avoid the over-fitting difficulties inherent in many parametric regression and machine learning methods.

GPR is formulated around a kernel function, k(,), that can incorporate prior knowledge about the local shape of the performance function (obtained from experience and data derived in previous epidural stimulation studies), to extend inference from previously explored stimulus patterns to new untested stimuli. Given a function that measures performance (e.g., stepping, standing, or reaching), GPO is based on two key formulae and the selection of an appropriate kernel function. The core GPO equation describes the predicted mean $\mu_t(x^*)$ and $\sigma_t^2(x^*)$ of the performance function (over the space of possible stimuli), at candidate stimuli $x^*$, on the basis of past measurements (tests of stimuli values $X=\{x_1, x_2, \ldots\}$ which returned noisy performance values $Y_t=\{y_1, y_2, \ldots\}$)

$$\mu_t(x^*) = k(x^*, X)[K_t(X, X) + \sigma_n^2 I]^{-1} Y_t;$$

$$\sigma_n^2(x^*) = k(x^*, x^*) - k(x^*, X)[K_t(X, X) + \sigma_n^2 I]^{-1} k(X, x^*)$$

where $K_t$ is the noiseless covariance matrix of past data, and $\sigma_n^2$ is the estimated noise covariance of the data that is used in the performance evaluation. To balance exploration of regions of the stimuli space where little is known about expected performance with exploitation of regions where we expect good performance, GPO uses an upper confidence bound update rule (Srinivas and Krause, *Gaussian Process Optimization in the bandit setting: No Regret and Experimental Design, Proc. Conf. on Machine Learning*, Haifa Israel (2010)).

$$x_{t+1} = \operatorname{argmax}_{x \varepsilon} x^* [\mu_t(x) + \beta_t \sigma_t(x)].$$

When the parameter $\beta_t$ increase with time, and if the performance function is a Gaussian process or has a low Reproducing Kernel Hilbert Space norm relative to a Gaussian process, GPO converges with high probability to the optimal action, given sufficient time.

The definition of a performance function that characterizes human motor behavior (e.g. standing or stepping behavior) typically depends upon two factors: (1) what kinds of motor performance data is available (e.g., video-based motion capture data, foot pressure distributions, accelerometers, electromyographic (EMG) measurements, etc.); and (2) the ability to quantify motor performance. While more sensory data is preferable, a machine learning approach to parameter optimization can employ various types of sensory data related to motor performance. It should be noted that even experts have great difficulty determining stepping or standing quality from such data without also looking at video or the actual subject as they undertake a motor task. However, given a sufficient number of training examples from past experiments and human grading of the standing or stepping in those experiments, a set of features that characterize performance (with respect to the given set of available sensors) can be learned and then used to construct a reasonable performance model that captures expert knowledge and that uses the available measurement data.

FIGS. 18A-18B depict a multi-compartment physical model of the electrical properties of mammalian spinal cord, along with a 27 electrode array placed in an epidural position. FIGS. 18A-18B also show the isopotential contours of the stimulating electric field for the 2-electrode stimulation example. FIG. 19 shows the instantaneous and average "regret" (a measure of the error in the learning algorithms search for optimal stimuli parameters) when the Gaussian Process Optimization algorithm summarized above is used to optimize the array stimulus pattern that excites neurons in the dorsal roots between segments L2 and S2 in the simulated spinal cord. The instantaneous regret performance shows that the learning algorithm rapidly finds better stimulating parameters, but also continually explores the stimulation space (the "bursts" in the graph of instantaneous regret correspond to excursions of the learning algorithm to regions of stimulus parameter space which were previously unknown, but which have been found to have poor performance).

Use of Robotically Guided Training to Assist Recovery of Standing and Stepping FIG. 2 shows that the use of physical training in combination with epidural stimulation and drug therapy produces better stepping behavior. Similarly, Example 1, herein, shows a similar effect of the combination of epidural stimulation and physical training/loading in a human subject.

While such physical manipulation can be facilitated by the use of trainers, e.g., as described above and in Example 1, in certain embodiments, the use of robotic devices and novel robotic control algorithms to guide and monitor the physical training process is contemplated. Robotic devices have been used successfully to train stepping and standing in complete spinal cord injured laboratory animals (Fong et al., *J Neuroscience*, 25 (50): 11738-11747 (2005); de Leon et al., *Brain Res Brain Res Rev.*, 40(1-3): 267-273 (2002); de Leon et al., *J Neurophysiol.*, 182(1): 359-369 (1999)). However, recovery of effective patterns and levels of neuromuscular activity in humans with SCI (without epidural stimulation) as a result of training with a robotic device has not yet been as successful (Wernig, *Arch Phys Med Rehabil.*, 86 (12): 2385-2386 (2005); author reply 2386-2387).

It is contemplated that "assist-as-needed" control algorithms that mimic the behavior of human therapists during weight supported treadmill step training 1 of human SCI patients can be utilized. When the limb kinematics of the SCI patient are poor, the therapists provides a large amount of physical bias to force the limbs to follow a more normal stepping pattern, as well as cutaneous sensory input to trigger reflex responses. When the limbs are moving close to a normal stepping pattern, the therapist provides little physical bias or sensory input to the patient. We implemented these algorithms on the robot of FIGS. 9, and found that even primitive assist-as-needed algorithms provide significant improvement in the rate and quality of step recovery. In this robotic device, lightweight low-friction robot arms guide the motions of the ankles of a weight-supported spinalized animal (mouse or rat) as it steps at various speeds on the moving treadmill. Because of the arms' low mass, they can also be used in a passive mode for testing locomotion ability—the movements of the animal's ankles are recorded by the robot as it attempts to walk on the treadmill (see, e.g., Cai, et al., *Proc. Int. Conference Rehab. Robotics.*, 9:575-579 (2005)).

Pharmacological Facilitation of Stepping, Standing, Reaching and Grasping

In certain embodiments, the methods described herein are used in conjunction with various pharmacological agents. In particular, the use of various serotonergic, and/or dopaminergic, and/or noradrenergic and/or GABAergic, and/or glycinergic drugs, particularly drugs that have been demonstrated to be effective in facilitating stepping in animals is contemplated. These agents can be used in combination with epidural stimulation and physical therapy as described above. This combined approach can help to put the spinal cord (below the site of lesion) in an optimal physiological state for controlling a range of lower and upper limb movements.

In certain embodiments, the drugs are administered systemically, while in other embodiments, the drugs are administered locally, e.g., to particular regions of the spinal cord. Drugs that modulate the excitability of the spinal neuromotor networks are combinations of noradrenergic, serotonergic, GABAergic, and glycinergic receptor agonists and antagonists. Illustrative pharmacological agents include, but are not limited to agonists and antagonists to one or more combinations of serotonergic: $5\text{-}HT_1A$, $5\text{-}HT_2A$, $5\text{-}HT_3$, and $5HT_7$ receptors; to noradrenergic alpha1 and 2 receptors; and to dopaminergic D1 and D2 receptors (see, e.g., Table 1).

TABLE 1

Illustrative pharmacological agents.

| Name | Target | Action | Route | Optimal Concentration (mg/Kg) | Range of tested concentrations (mg/Kg) |
|---|---|---|---|---|---|
| Serotonergic receptor systems | | | | | |
| 8-OHDPAT | 5-HT1A7 | Agonist | S.C. | 0.05 | 0.045-0.3 |
| Way 100.635 | 5-HT1A | Antagonist | I.P. | 0.5 | 0.4-1.5 |
| QUIPAZINE | 5-HT2A/C | Agonist | I.P. | 0.2 | 0.18-0.6 |
| KETANSERIN | 5-HT2A/C | Antagonist | I.P. | 3 | 1.5-6.0 |
| SR 57227A | 5-HT3 | Agonist | I.P. | 1.5 | 1.3-1.7 |
| ONDANSETRON | 5-HT3 | Antagonist | I.P. | 3 | 1.4-7.0 |
| SB 269970 | 5-HT7 | Antagonist | I.P. | 7 | 2.0-10.0 |
| Noradrenergic receptor systems | | | | | |
| METHOXAMINE | Alpha1 | Agonist | I.P. | 2.5 | 1.5-4.5 |
| PRAZOSIN | Alpha1 | Antagonist | I.P. | 3 | 1.8-3.0 |
| CLONIDINE | Alpha2 | Agonist | I.P. | 0.5 | 0.2-1.5 |
| YOHIMBINE | Alpha2 | Antagonist | I.P. | 0.4 | 0.3-0.6 |
| Dopaminergic receptor systems | | | | | |
| SKF-81297 | D1-like | Agonist | I.P. | 0.2 | 0.15-0.6 |
| SCH-23390 | D1-like | Antagonist | I.P. | 0.15 | 0.1-0.75 |
| QUINPIROLE | D2-like | Agonist | I.P. | 0.3 | 0.15-0.3 |
| ETICLOPRIDE | D2-like | Antagonist | I.P. | 1.8 | 0.9-1.8 |

The foregoing embodiments are intended to be illustrative and not limiting. Using the teachings and examples provided herein, numerous variations 5 on the methods and devices described herein will be available to one of ordinary skill in the art.

EXAMPLES

The following examples are offered to illustrate, but not to limit the claimed invention.

Example 1

Epidural stimulation of the lumbosacral spinal cord enables independent standing, voluntary movement, and assisted stepping in a paraplegic human.

This example demonstrates that the human spinal cord circuitry has the ability to generate postural and locomotor patterns without supraspinal motor input. This capability and voluntary movement can be manifested when the excitability of these networks is modulated by epidural stimulation at a level that enables proprioceptive input to provide a source of neural control to elicit the motor pattern appropriate for the task.

Introduction

The mammalian spinal cord can generate locomotor output in the absence of input from the brain. See Grillner S., Neurobiological bases of rhythmic motor acts in vertebrates, *Science,* 228:143-149 (1985); and Rossignol S, Barriere G, Frigon A, Barthelemy D, Bouyer L, Provencher J, et al., Plasticity of locomotor sensorimotor interactions after peripheral and/or spinal lesions, *Brain Res Rev,* 57(1): 228-240 (January 2008). This capability has been attributed to the phenomenon of central pattern generation. See Grillner S, Wallen Peter, Central pattern generators for locomotion, with special reference to vertebrates, *Ann Rev Neurosci,* 8:233-261 (1985); and Grillner S, Zangger P., On the central generation of locomotion in the low spinal cat, *Exp Brain Res,* 34:241-261 (1979). Functional standing and stepping can be executed by cats with complete transection of the spinal cord when sensory input is provided to the lumbosacral locomotor pattern generator circuitry. See de Leon R D, Hodgson J A, Roy R R, Edgerton V R., Locomotor capacity attributable to step training versus spontaneous recovery after spinalization in adult cats, *J Neurophysiol,* 79:1329-1340 (1998); and Barbeau H, and Rossignol S., Recovery of locomotion after chronic spinalization in the adult cat, *Brain Res,* 412:84-95 (1987). Spinal cats can learn to stand, fully supporting their hindquarters, and to step over a range of speeds and load-bearing levels with task specific training. Adult spinally transected rats, unlike cats, can generate stepping only with additional combined interventions of locomotor training, pharmacological intervention, and/or epidural stimulation. See Courtine G, Gerasimenko Y, van den BR, Yew A, Musienko P, Zhong H, et al., Transformation of nonfunctional spinal circuits into functional states after the loss of brain input, *Nat Neurosci,* 12 (10): 1333-1342 (October 2009); and Ichiyama R M, Courtine G, Gerasimenko Y P, Yang G J, van den BR, Lavrov I A, et al., Step training reinforces specific spinal locomotor circuitry in adult spinal rats, *J Neurosci,* 16; 28 (29): 7370-7375 (July 2008). These observations demonstrate a level of automaticity sufficient to generate locomotion without any supraspinal influence. This evidence leads to the hypothesis that if similar spinal circuits exist in humans then electrically stimulating the lumbosacral spinal cord epidurally should be able to facilitate standing and stepping in an individual with a motor complete spinal cord injury.

Although, rhythmic motor patterns of the legs have been observed, 12-15 sustained independent, full weight-bearing standing and stepping has not been reported in humans after complete motor paralysis. See Calancie B., Spinal myoclonus after spinal cord injury, *J Spinal Cord Med,* 29:413-424 (2006); Dimitrijevic M R, Gerasimenko Y, Pinter M M, Evidence for a spinal central pattern generator in humans, *Ann NY Acad Sci,* 16; 860:360-376 (November 1998); Kuhn R A. Functional capacity of the isolated human spinal cord, *Brain,* 73(1): 1-51 (1950); and Nadeau S, Jacquemin G, Fournier C, Lamarre Y, Rossignol S., Spontaneous motor rhythms of the back and legs in a patient with a complete spinal cord transection, *Neurorehabil Neural Repair,* 24(4): 377-383 (May 2010). However, after a motor incomplete SCI functional improvements occur with intense locomotor training and with epidural stimulation. See Wernig A, and Muller S., Laufband locomotion with body weight support improved walking in persons with severe spinal cord injuries, Para; 30:229-238 (1992); Wernig A, Nanassy A, Muller S., Maintenance of locomotor abilities following Laufband (treadmill) therapy in para- and tetraplegic persons: follow-up studies, *Spinal Cord,* 36:744-749 (1998); and Herman R, He J, D'Luzansky S, Willis W, Dilli S., Spinal cord stimulation facilitates functional walking in a chronic, incomplete spinal cord injured. Spinal Cord, 40 (2): 65-68 (February 2002). Rhythmic efferent activity timed to the step cycle, however, can occur during manually facilitated stepping and bilateral tonic activity can occur during partial weight bearing standing in individuals with a clinically complete SCI after extensive task specific training. See Dietz V, Colombo G, Jensen L., Locomotor activity in spinal man, *The Lancet,* 344:1260-1263 (1994); Harkema S J, Hurley S L, Patel U K, Requejo P S, Dobkin B H, Edgerton V R, Human lumbosacral spinal cord interprets loading during stepping, *J Neurophysiol,* 77 (2): 797-811 (1997); and Harkema S J, Plasticity of interneuronal networks of the functionally isolated human spinal cord, *Brain Res* Rev, 57(1): 255-264 (January 2008). Rhythmic and tonic motor patterns of the legs have been induced via epidural stimulation in humans after motor complete SCI while lying supine. See Dimitrijevic M R, Gerasimenko Y, Pinter M M, Evidence for a spinal central pattern generator in humans, *Ann NY Acad Sci,* 16; 860:360-376 (November 1998); Gerasimenko Y, Daniel O, Regnaux J, Combeaud M, Bussel B., *Mechanisms of locomotor activity generation under epidural spinal cord stimulation,* In: Dengler R, Kossev A, editors, Washington, DC: IOS Press, p. 164-171 (2001); and Minassian K, Jilge B, Rattay F, Pinter M M, Binder H, Gerstenbrand F, et al., Stepping-like movements in humans with complete spinal cord injury induced by epidural stimulation of the lumbar cord: electromyographic study of compound muscle action potentials, *Spinal Cord,* 42 (7): 401-416 (July 2004). This suggests that spinal circuitry for locomotion is present in the human but cannot functionally execute these tasks without some level of excitability from supraspinal centers that may be present after incomplete SCI.

We hypothesized that tonic epidural spinal cord stimulation can modulate the human spinal circuitry into a physiological state that enables sensory input derived from standing and stepping movements to serve as a source of neural control to perform these tasks. We observed that the spinal circuitry was able to generate independent standing in response to task specific sensory cues in the presence of epidural stimulation in a paraplegic subject with a motor complete spinal cord injury. Stepping-like patterns were also generated with epidural stimulation with the subject on a treadmill using body weight support and manual facilitation. The subject also regained some voluntary control of the legs seven months post implantation. We have used epidural stimulation to substitute for descending signals that normally come from the brain to modulate the physiological state of the spinal networks and the sensory information can be used as a source of neural control of the motor task. Unexpectedly, clinical assessments indicated improvements in other physiological functions including bladder, sexual function and temperature regulation.

Methods

Clinical Characteristics Prior to Implantation

The subject is a 23 year old man who had been struck by a motor vehicle 3.4 years prior to implantation. He sustained a C7-T1 subluxation with injury to the lower cervical and upper thoracic spinal cord. Neurological examination revealed paraplegia. The triceps and intrinsic hand muscles exhibited voluntary contraction but were weak. He had no contraction of trunk or leg muscles. He was treated emergently with reduction of the subluxation by anterior interbody fusion and instrumentation. Magnetic resonance imaging of the injury site obtained prior to implantation revealed myelomalacia and atrophy of the cord segment adjacent to the T1 vertebral body (see FIG. 10A).

Prior to the lumbosacral epidural implantation his neurological deficit was classified using the American Spinal Injury Association (ASIA) impairment scale (AIS) as ASIA B (pinprick and light-touch present below the lesion). Marino R J, Barros T, Biering-Sorensen F, Burns S P, Donovan W H, Graves D E, et al., International standards for neurological classification of spinal cord injury, *J Spinal Cord Med,* 26 Suppl 1: S50-S56 (2003). He had no motor function of trunk or leg muscles, a flaccid anal sphincter, and no voluntary bladder contraction (see FIG. 10B). Sensation was abnormal below C7.

Somatosensory evoked potentials showed bilateral delay of cortical responses from posterior tibial nerve stimulation. Latencies of sensory evoked potentials recorded at Erb's point, cervical, and contralateral cortical sites in response to median nerve stimulation at the wrist were within normal ranges. Lower extremity nerve conduction studies were normal. No response was elicited from leg muscles by transcranial magnetic stimulation of the motor cortex using a butterfly coil centered over Cz. He was unable to stand or walk independently or voluntarily move his legs despite standard-of-care rehabilitation and additional intensive locomotor training.

The research subject signed an informed consent for electrode implantation, stimulation, and physiological monitoring studies that was approved by the University of Louisville and the University of California, Los Angeles Institutional Review Boards. To be certain there was no remaining potential for standing and walking, prior to the electrode implantation, the participant received 170 locomotor training sessions over a period of 26 months using body weight support on a treadmill with manual facilitation resulting in 108 hours of step training and 54 hours of stand training with no detectable change in EMG activity (see FIG. 12). During standing, throughout training no observable EMG was evident. During assisted stepping, sporadic EMG activity was observed in the lower leg muscles, most often in the medial hamstrings, however, was never observed EMG activity in all muscles bilaterally. No detect-able improvement in EMG was noted over the course of the training.

Surgical Implantation of Electrode Array and Stimulator

An epidural spinal cord stimulation unit (Medtronics, Restore Advanced) was used to electrically stimulate the lumbar-sacral enlargement. A 16-electrode array was implanted epidurally under fluoroscopic control at T11-L1 over lumbosacral spinal cord segments L1-S1 (see FIG. 11A). The location of the electrode array was evaluated and adjusted during surgery with fluoroscopy and electrophysi-ologically with EMG recorded from leg muscles. See Murg M, Binder H, Dimitrijevic M R, Epidural electric stimula-tion of posterior structures of the human lumbar spinal cord: 1. muscle twitches-a functional method to define the site of stimulation, Spinal Cord, 38:394-402 (2000). EMG responses were elicited by epidural stimulation at 2 Hz during a sequence of increasing voltages and specific elec-trode configurations to determine threshold of muscle acti-vation and amplitude of the response. A midline stimulation configuration was followed using one cathode and one anode electrode, with each electrode pair being 6 mm apart. Multiple stimulation combinations were performed ranging from most rostral to most caudal positions. Symmetry was also tested by using left and right side electrodes within the array. The electrode lead was tunneled to a subcutaneous abdominal pouch where the pulse generator was implanted. Two weeks after implantation the position of the array was reconfirmed with the subject lying supine using the same stimulation protocols (see FIGS. 11C-11D).

Experimental Design

Stimulation parameters were systematically evaluated to identify the optimal stimulation parameters for generating efferent patterns for standing and stepping. Stimulation of the spinal cord was carried out during sessions lasting up to 250 minutes in which physiological parameters were mea-sured. The total duration of stimulation during each experi-mental session ranged from 40 minutes to 120 minutes. Stimulation amplitudes ranged from 0.5 V to 10.0 V and stimulation frequencies from 5 to 40 Hz using either a 210 or 450 us pulse width. The optimal configurations for standing were those with which sustainable tonic co-activa-tion were evoked; for stepping optimal configurations were those in which rhythmic activity was present with alterna-tion of right and left leg and intralimb flexors and extensors. EMG activity of 14 lower extremity muscles and hip, knee, and ankle joint angles were measured.

During experimental sessions on the treadmill, level of body weight support (Innoventor, St. Louis, MO) and amount of body weight load were also measured. Trainers provided manual facilitation, when needed, distal to the patella during the stance phase, and at the popliteal fossa and anterior distal tibia for foot clearance during the swing phase and at the pelvis for stabilization and weight shifting during stepping. Stand training was performed using a custom-made standing device designed to provide full weight-bearing and pelvis support. The device included vertical and horizontal bars positioned about (or surrounding) the subject to allow him to assist balance. Bungees were attached to the device to provide support only if the knees or hips flexed beyond the normal standing posture. The total duration of stimulation during each session averaged 44 minutes (sessions 1-34) and 60 minutes (sessions 35-80). Epidural stimu-lation was not provided outside laboratory sessions. The subject attempted to stand for 60 minutes during each training session. To optimize independent standing stimula-tion parameters (electrode configuration, voltage and fre-quency) were modified approximately once per week.

During sitting, stimulation voltage was increased to a desired level. This voltage was kept constant as the subject went from sitting to standing and throughout the standing bout. The subject initiated the sit to stand transition by positioning his feet shoulder width apart and shifting his weight forward to begin loading the legs. The subject used the bars of the standing device during the transition phase to balance and to partially pull himself into a standing position. Trainers positioned at the pelvis and knees assisted as needed during the sit to stand transition. Elastic bungees posterior to the pelvis were set by one of the trainers after the subject achieved full-weight bearing standing. These bun-gees helped the subject sustain appropriate pelvic tilt and position and allowed him to safely stand with minimal assistance.

During the standing bout, one trainer assisted the subject by applying posteriorly directed gentle pressure at the patel-lar tendon as necessary to maintain knee extension. The subject was encouraged to stand for as long as possible throughout the session.

Seated resting periods occurred when requested by the subject and reduced in frequency and duration as the training progressed. No stimulation was provided during the rest periods.

During the first stand session, the subject required 7 breaks (stand time: 60 min; rest time 67 minutes). By session 35, the subject was able to stand for 1 bout lasting a full 60 minutes. The total duration of stimulation averaged across all sessions was 54±13 minutes per session.

Data Acquisition

EMG, joint angles, footswitch, ground reaction forces and BWS data were collected at 2,000 Hz using a 32-channel hard-wired AD board and custom-written acquisition soft-ware (National Instruments, Austin, TX). Bilateral EMG (Motion Lab Systems, Baton Rouge, LA) from the soleus, medial gastrocnemius, tibialis anterior, medial hamstrings, quadriceps, and gluteus maximus muscles was recorded using bipolar surface electrodes with fixed inter-electrode distance. Harkema S J, Hurley S L, Patel U K, Requejo P S, Dobkin B H, Edgerton V R, Human lumbosacral spinal cord interprets loading during stepping, J Neurophysiol, 77 (2): 797-811 (1997); and Beres-Jones J A, Johnson T D, Harkema S J, Clonus after human spinal cord injury cannot be attributed solely to recurrent muscle-tendon stretch, Exp Brain Res, 149 (2): 222-236 (March 2003). Bilateral EMG from the iliopsoas was recorded with fine-wire electrodes. Two surface electrodes placed symmetrically lateral to the electrode array incision site over the paraspinal muscles were used to record the stimulation artifact. Hip, knee, and ankle joint angles were acquired using a high speed passive marker motion capture system (Motion Analysis, Santa Rosa, CA). Ground reaction forces were collected using shoe-insole pressure sensors FSCAN or HRMAT (TEKSCAN, Boston, MA).

Results

The patient was always aware when the stimulation was on, with the most common sensation being a tingling feeling localized to the thoraco-lumbar electrode implantation site. There was a similar sensation in those muscles that were targeted for activation. Parasthesias were also routinely perceived in the trunk, hips, and legs and varied according to the intensity of stimulation, however were never at a level that produced discomfort or pain and never precluded the use of epidural stimulation.

EMG Activity with Epidural Stimulation for Standing

Epidural stimulation at 15 Hz and 8 V of the caudal segments (L5-S1) of the spinal cord combined with sensory information related to bilateral extension and loading was sufficient to generate standing on day five of stimulation (see FIG. 13). Standing without manual facilitation at the legs was achieved using stimulation (15 Hz, 8 V) with 65% body weight support (see FIG. 13, panel A). The subject was able to sustain standing without any manual facilitation while the level of body weight support was progressively reduced to full weight-bearing (see FIG. 13, panel B).

Transitioning from sitting to standing without body weight support altered the EMG activity during rostral or caudal epidural stimulation even though the parameters remained constant (see FIG. 14). When loading of the legs was initiated, the EMG activity increased dramatically and was sufficient to support the subject's body weight with minimal assistance required by the trainers. During this transition, the stimulation remained constant using the same location, frequency, and intensity parameters (FIG. 14, panels B-E). The EMG activity was also modulated by the site and intensity of stimulation. The EMG activity was dependent on the site and intensity of stimulation with the caudal (L5-S1) stimulation at higher intensities resulting in the most optimal motor pattern for standing (see FIG. 14, panels A-C). During caudal stimulation, there was a more dramatic increase in the EMG amplitude bilaterally in the more proximal muscles while EMG of the more distal muscles was initially markedly reduced (see FIG. 14, panels C and E). Once standing was achieved, there was more co-contraction of both flexors and extensors and proximal and distal muscles with stimulation.

Postural Responses and Independent Standing with Epidural Stimulation

Postural responses were observed in the leg EMG activity when the subject voluntarily shifted his center of gravity sagittally while standing with epidural stimulation and intermittent manual assistance (see FIG. 15, panel A). The EMG burst of the medial gastrocnemius increased with forward deviation, whereas backward deviation induced EMG bursts in the tibialis anterior. Independent standing bouts with tonic bilateral EMG activity routinely occurred for several continuous minutes and increased in frequency and duration as stand training progressed (see FIG. 15, panel B). After 80 sessions, the subject could initiate and maintain continuous independent standing (maximum 4.25 min) with bilateral tonic EMG activity (see FIG. 15, panel B). Oscillatory patterns, often clonic-like, emerged during the latter part of the periods of independent standing and then were followed by little or no EMG activity that corresponded with the loss of independence (requiring a return to manually facilitated standing). These periods of independent standing were repeated during the 60-minute standing sessions.

Thus, independent standing occurred when using stimulation having parameters selected (e.g., optimized) to facilitate standing while providing bilateral load-bearing proprioceptive input.

Locomotor Patterns with Epidural Stimulation

For stepping, epidural stimulation at 30-40 Hz and task-specific sensory cues were used to generate locomotor-like patterns. Sensory cues from manually facilitated stepping included load alternation and leg positioning with appropriate kinematics of the hips, knees, and ankles timed to the step cycle. Stepping with BWST without epidural stimulation produced little or no EMG activity (see FIG. 16, panel A). Stepping with BWST and manual facilitation in conjunction with caudal epidural stimulation resulted in an oscillatory EMG pattern in flexors and extensors (see FIG. 16, panel B). The afferent feedback determined the motor efferent pattern (see FIG. 16, panels C and D). The EMG activity in the legs was dramatically different depending on the loading and kinematic patterns when using the identical stimulation parameters. Oscillatory EMG patterns were evident only when alternating loading and flexion and extension of the lower limbs occurred (see FIG. 16, panels C and D).

Voluntary Control of Leg Movement

Voluntary (or supraspinal) control of the toe extension, ankle flexion, and leg flexion emerged only in the presence of epidural stimulation (see FIG. 17) seven months after the epidural implant that included 80 stand training sessions with epidural stimulation. Voluntary movement was observed in both limbs. However, the epidural stimulation parameters were different for each leg and technical limitations of the stimulator prevented simultaneous movements of the legs bilaterally. When the subject was instructed to flex (draw the leg upward) the toe extended, the ankle dorsi-flexed and the hip and knee flexed with the appropriate muscle activation. When instructed to dorsi-flex the ankle, the foot moved upward with tibialis anterior activation. When instructed to extend the great toe, the toe moved upward with activation of the extensor hallicus longus. For each task, the muscle activation was specific for the movement and the timing of activation was closely linked to the verbal commands (see FIGS. 17C-17E). The subject could consciously activate the appropriate muscles for the intended movement, and the timing of activation was closely linked to the verbal commands (see FIG. 17E). The ability to selectively activate different motor pools demonstrates an important feature of voluntary motor control.

Thus, locomotor-like patterns were observed when stimulation parameters were selected (e.g., optimized) to facilitate stepping. Further, seven months after implantation, the subject recovered supraspinal control of certain leg movements, but only during epidural stimulation.

Subject's Perspective

Given the uniqueness of the epidural stimulation procedures and the unusual level of commitment of the subject to the objectives of the study, the research team asked the subject his perspective on a range of highly personal topics related to changes in his health and daily living after compared to before the implant.

Interpretation of these responses should take into account that the subject received extensive rehabilitation for 170 sessions immediately before the implant. Specifically, the subject provided the following responses as to how (other than demanding so much of his time) the experience affected the specified aspect of his life:

1. sleep patterns: I am sleeping more soundly, and am able to reach a deeper level of sleep (the dream phase) almost every night. I have also noticed that I need more sleep, at least 10 hours a night and sometimes more after a hard or draining workout.
2. daily activity patterns: Besides the issue of being tired from the workouts, I have had more over all energy. I have been more active during the days than before the implant. This has improved since the first few workouts after the surgery, since at first I could not do anything and even had trouble transferring after workouts, but this has continuously gotten better every day.

3. bladder or bowel function: In terms of my bladder, I've been able to empty more often on my own, on command, without a catheter. So far I've had no infections as well. In terms of my bowel function, I'm more regular.
4. sensory function: I've been able to feel more sharp and dull sensations in places where I wasn't able to before the surgery, such as through my stomach and legs. Also I'm having better sensation with light touch throughout my midsection and legs. Refer to most recent ASIA exam where I had mostly zeros before surgery and now have mostly ones.
5. severity and frequency and timing of spasticity: My spasticity has increased only when lying down.
6. frequency and kind of medical care needed: Other than when my stitches opened shortly after surgery no medical care has been needed since surgery.
7. sexual function: Erections have been stronger and more frequent and I am able to reach full orgasm occasionally. I had never before been able to do this before the surgery.
8. diet, appetite: I feel like I get hungrier after working out, but other than that no change.
9. body weight: I've gained about 9 kilograms since surgery.
10. observable changes in muscle: My leg muscles have increased by a few inches and I am able to see definition in my quads and calfs. My upper body (biceps, triceps, shoulders etc.) have also gained inches of muscle and I have not lifted a weight since surgery. My overall core has gotten stronger and more stable.
11. posture and stability when sitting: My posture has improved. I'm more stable and have less need to hold onto things to support myself.
12. skin lesions or sensitivity to infections: I have had no infections or skin lesions.
13. other functions: I feel healthier, I have better self-esteem and confidence. My legs are heavier and more dense.

Clinical Impressions

With training and epidural stimulation, the subject had functional gains in bladder and sexual function, and temperature regulation. The subject has been able to voluntarily void with minimal residual volume, and reports normal sexual response and performance. The subject regained diaphoretic capability and ability to tolerate temperature extremes. In addition, a sense of well-being and increased self-esteem enabled more frequent social interactions. An eighteen percent gain in weight was associated with increased appetite and relative increase in lean body mass and decrease in total body fat as measured using aq DEXA scan.

Discussion

We have used an epidurally implanted electrode array to modulate the physiological state of the spinal circuitry to enable independent standing in a human with a chronic motor complete spinal cord injury. The epidural stimulation did not induce standing by directly activating motor pools, but enabled motor function by engaging populations of interneurons that integrated load-bearing related proprioceptive input to coordinate motor pool activity. This phenomenon was observed within the first week of stimulation. Although motor pool activity occurred in the presence of epidural stimulation during sitting, the functional activity needed for standing required the proprioceptive information associated with load bearing positional changes. Dynamic changes in position during standing were accompanied by motor patterns needed to maintain upright posture without changes in the epidural stimulation parameters. Intensive task specific training combined with epidural stimulation extended the duration of periods of independent standing that could be initiated by the subject.

Robust, consistent rhythmic stepping-like activity emerged during stepping only when tonic epidural stimulation and weight-bearing associated proprioception was present. When standing, the same epidural stimulation parameters elicited primarily tonic bilateral activity; however when stepping it resulted in rhythmic alternating activity. Without being limited by theory, it is believed the epidural stimulation may activate dorsal root afferent fibers and, more likely at higher intensities, dorsal columns and additional spinal structures. The continuous stimulation enabled the spinal cord to process the sensory information that is closely linked to the desired functional task by modulating the physiological state of the spinal cord. This is of great clinical importance and it allows the intervention to become feasible since the task needed can be driven and controlled by intrinsic properties of the nervous system rather than an external control system.

Our study demonstrates that the sensory input can serve as the controller of the spinal circuitry during independent standing and assisted stepping when enabled by epidural stimulation in the absence of supraspinal input in humans.

The present results show that movements of several lower limb joints can be controlled voluntarily. In subjects with a motor incomplete spinal injury, a common phenomenon is the general loss of specificity of control of selected muscles, however, the voluntary nature of these reported movements are selective. See Maegele M, Muller S, Wernig A, Edgerton V R, Harkema S J, Recruitment of spinal motor pools during voluntary movements versus stepping after human spinal cord injury, *J Neurotrauma,* 19 (10): 1217-1229 (October 2002). In Example 1, the activated motor pools were appropriate for the intended movement. Two possible mechanisms that might explain this result include: 1) that the epidural stimulation provided excitation of lumbosacral interneurons and motoneurons (Jankowska E., Spinal interneuronal systems: identification, multifunctional character and reconfigurations in mammals, *J Physiol,* 533 (Pt 1): 31-40 (May 15 2001)) which, combined with the weak excitatory activity of residual motor axons descending through the cervicothoracic injury, achieved a level of excitation that was sufficient to fire the motoneurons and/or 2) axonal regeneration or sprouting may have been induced via activity-dependent mechanisms occurring over a period of months. It is highly significant from a neurobiological as well as a clinical perspective that this voluntary control was manifested only in the presence of continuous tonic epidural stimulation. This demonstrates that by elevating the level of spinal interneuronal excitability to some critical, but sub-threshold level, voluntary movements can be regained. Dimitrijevic MR, Gerasimenko Y, Pinter M M, Evidence for a spinal central pattern generator in humans, *Ann NY Acad Sci,* 16; 860:360-376 (November 1998). These same mechanisms may also explain the improved autonomic function in bladder, sexual, vasomotor, and thermoregulatory activity that has been of benefit to the subject. The areas of lumbosacral spinal cord stimulated included at least parts of the neural circuits that regulate these autonomic functions and may have also resulted in activity-dependent changes. In other words, given that the broad areas of the lumbosacral spinal cord stimulated include at least parts of the neural circuits that regulate these autonomic functions, these changes might have been expected if the neural networks controlling these autonomic functions are activity-dependent.

These data demonstrate that humans have conserved spinal locomotor circuitry as found in other mammals that include: 1) transition from a low level activity state to one that can generate active standing in the presence of tonic epidural stimulation; 2) gate tonic electrically evoked responses according to the task specific sensory input, resulting in specific patterns of coordination within and between the motor pools; 3) use appropriate task specific sensory input to control the level and timing of neural excitation sufficient to generate independent standing and facilitate stepping; and 4) to mediate voluntarily initiated movement of the lower limbs in the presence of epidural stimulation. A higher level of improvement in motor function may be achieved with the addition of pharmacological agents not only in spinal cord injury but also with other neuromotor disorders. See Fuentes R, Petersson P, Siesser W B, Caron M G, Nicolelis M A, Spinal cord stimulation restores locomotion in animal models of Parkinson's disease, *Science*, 323 (5921): 1578-1582 (Mar. 20, 2009).

In Example 1, epidural stimulation of the human spinal cord circuitry combined with task specific proprioceptive input resulted in novel postural and locomotor patterns. After seven months of stimulation and stand training, supraspinally mediated movements of the legs were manifested only in the presence of epidural stimulation. Task specific training with epidural stimulation may have reactivated previously silent spared neural circuits or promoted plasticity. Thus, such interventions may provide a viable clinical approach for functional recovery after severe paralysis.

The above example supports the following. First, it is possible to stimulate the lumbosacral spinal cord with a modest, but sufficient level of intensity to enable the sensory input from the lower limbs to serve as a source of control of standing and to some degree of stepping. Second, the ability to stand for greater durations increases with daily stand training. Third, after months of stand training in the presence of epidural stimulation, there was sufficient supraspinal and spinal reorganization to enable conscious control of movements of the lower limbs. Fourth, extensive reorganization of supraspinal and spinal motor systems can occur in response to activity-dependent interventions in an individual with complete paralysis for more than 3 years after a lower cervical-upper thoracic spinal cord injury. None of these observations in a human subject with this severity of injury have been made previously.

Some additional publications discussing related technologies include the following:

1. Gerasimenko Y, Roy R R, Edgerton V R., Epidural stimulation: comparison of the spinal circuits that generate and control locomotion in rats, cats and humans, *Exp Neurol*, 209 (2): 417-425 (February 2008);
2. Grillner S, Wallen Peter, Central pattern generators for locomotion, with special reference to vertebrates, *Ann Rev Neurosci*, 8:233-261 (1985);
3. Grillner S., The motor infrastructure: from ion channels to neuronal networks, *Nat Rev Neurosci*, 4 (7): 573-586 (July 2003);
4. Grillner S, Zangger P., On the central generation of locomotion in the low spinal cat, *Exp Brain Res*; 34:241-261 (1979);

5. de Leon R D, Hodgson J A, Roy R R, Edgerton V R., Full weight-bearing hindlimb standing following stand training in the adult spinal cat, *J Neurophysiol*, 80:83-91 (1998);
6. Harkema S, Schmidt-Read M, Lorenz D, Edgerton V R, Behrman A., Functional recovery in individuals with chronic incomplete spinal cord injury with intensive activity-based rehabilitation, *Arch Phys Med Rehab*, InPress;
7. Minassian K, Persy I, Rattay F, et al., Human lumbar cord circuitries can be activated by extrinsic tonic input to generate locomotor-like activity, *Hum Mov Sci*, 26:275-95 (2007);
8. Jilge B, Minassian K, Rattay F, et al., Initiating extension of the lower limbs in subjects with complete spinal cord injury by epidural lumbar cord stimulation, *Exp Brain Res*, 154 (3): 308-26 (2004); and
9. Fuentes R, Petersson P, Siesser W B, Caron M G, Nicolelis M A., Spinal cord stimulation restores locomotion in animal models of Parkinson's disease, *Science*, 323 (5921): 1578-1582 (Mar. 20, 2009).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entireties for all purposes.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

We claim:

1. A method of enabling or improving, in a patient having a neurologically derived paralysis, control autonomic functions including at least one of a cardiovascular autonomic function or a vasomotor autonomic function, the method comprising:

receiving, in a processor, data related to the one or more autonomic functions in the patient during postural training to induce postural proprioceptive signals in the patient;

detecting, via the processor, the one or more autonomic functions in the patient during the postural training based on the received data;

selecting, using the processor, electrical stimulation parameters among a plurality of electrical stimulation parameters based on the detected one or more autonomic functions; and applying, via an electrode array that is communicatively coupled to the processor, electrical stimulation using the selected electrical stimulation parameters to a portion of a spinal cord of the patient, the electrode array electrically coupled to the portion of the spinal cord, wherein at least one of the electrical stimulation or the postural training is configured to modulate in real time electrophysiological properties of a spinal circuit in the patient so the spinal circuit is activated by postural proprioceptive signals that are derived from a region of the patient where the one or more autonomic functions are enabled or improved.

2. The method of claim 1, wherein selecting the electrical stimulation parameters includes using, via the processor, a machine learning algorithm including a regression model that relates the one or more autonomic functions of the patient to the selected electrical stimulation parameters, the machine learning algorithm configured to use the regression model to select the electrical stimulation parameters for increasing functional performance of the patient during the postural training.

3. The method of claim 1, wherein the spinal circuit includes a first stimulation threshold representing a minimum amount of stimulation required to activate the spinal circuit and a second stimulation threshold representing an amount of stimulation above which the spinal circuit is fully activated, and wherein the electrical stimulation applied to the portion of the spinal cord of the patient is below the second stimulation threshold such that addition of the postural training activates the spinal circuit by the postural proprioceptive signals that are derived from the region of the patient where the one or more autonomic functions occur.

4. The method of claim 1, wherein the postural training comprises at least one of stabilizing sitting posture or stabilizing standing posture.

5. The method of claim 1, wherein the electrode array comprises one or more electrodes stimulated in a monopolar configuration or bipolar configuration.

6. The method of claim 1, wherein the electrical stimulation comprises at least one of tonic stimulation or intermittent stimulation.

7. The method of claim 1, wherein the postural training comprises inducing a postural change at the region of the patient.

8. The method according to claim 7, wherein the postural change in the patient comprises at least one of standing up or sitting down.

9. The method of claim 1, further comprising causing one or more neuropharmaceutical agents to be administered to the patient before, during, or after the postural training, the one or more neuropharmaceutical agents including at least one of a serotonergic drug, a dopaminergic drug, a noradrenergic drug, a GABAergic drug, a glycinergic drug, or a combination thereof.

10. The method of claim 1, wherein the electrical stimulation parameters define at least one of stimulating voltage amplitudes, stimulating currents, stimulating frequencies, or stimulating waveform shapes for the electrical stimulation.

11. The method of claim 1, wherein receiving the data further comprises detecting, with a sensor, the one or more autonomic functions in the patient during the postural training.

12. A system for enabling or improving, in a patient having a neurologically derived paralysis, control autonomic functions including at least one of a cardiovascular autonomic function or a vasomotor autonomic function, the system comprising:

an electrode array electrically coupled to a portion of a spinal cord of the patient; and a processor communicatively coupled to the electrode array, the processor configured to:

receive data related to the one or more autonomic functions in the patient during postural training using a training device, the training device configured to induce postural proprioceptive signals in the patient, detect the one or more autonomic functions in the patient during the postural training based on the received data, select electrical stimulation parameters among a plurality of electrical stimulation parameters based on the detected one or more autonomic functions, and cause the electrode array to apply electrical stimulation using the selected stimulation parameters to the portion of the spinal cord of the patient, wherein at least one of the electrical stimulation or the postural training is configured to modulate electrophysiological properties of a spinal circuit in the patient so the spinal circuit is activated by the postural proprioceptive signals that are derived from a region of the patient where the one or more autonomic functions are enabled or improved.

13. The system of claim 12, wherein the processor is configured to use a machine learning algorithm including a regression model that relates the one or more autonomic functions of the patient to the selected electrical stimulation parameters, the machine learning algorithm configured to use the regression model to select the electrical stimulation parameters for increasing functional performance of the patient during the postural training.

14. The system of claim 12, wherein the spinal circuit includes a first stimulation threshold representing a minimum amount of stimulation required to activate the spinal circuit and a second stimulation threshold representing an amount of stimulation above which the spinal circuit is fully activated, and wherein the electrical stimulation applied to the portion of the spinal cord of the patient is configured to be below the second stimulation threshold such that addition of the postural training activates the spinal circuit by the postural proprioceptive signals that are derived from the region of the patient where the one or more autonomic functions occur.

15. The system of claim 12, wherein the electrode array comprises one or more electrodes stimulated in a monopolar configuration or bipolar configuration.

16. The system of claim 12, wherein the electrical stimulation comprises at least one of tonic stimulation or intermittent stimulation.

17. The system of claim 12, wherein the electrical stimulation parameters define at least one of stimulating voltage amplitudes, stimulating currents, stimulating frequencies, or stimulating waveform shapes for the electrical stimulation.

18. The system of claim 12, further comprising a sensor communicatively coupled to a sensor, the sensor configured to detect the data corresponding to the one or more autonomic functions in the patient during the postural training.

19. The system of claim 12, wherein the processor is configured to cause the electrode array to apply the electrical stimulation before, during, or after one or more neuropharmaceutical agents is administered to the patient, the one or more neuropharmaceutical agents including at least one of a serotonergic drug, a dopaminergic drug, a noradrenergic drug, a GABAergic drug, a glycinergic drug, or a combination thereof.

20. The system of claim 12, wherein the postural training comprises at least one of standing up, sitting down, laying down, stabilizing sitting posture, or stabilizing standing posture.

21. A method of enabling or improving, in a patient having a nervous system disorder, one or more autonomic function selected from the group consisting of cardiovascular function, body temperature, metabolic processes, sexual function, bladder function, vasomotor function, or cognitive function, the method comprising:

inducing, with a stimulator including a processor connected to at least one electrode, spinal interneuronal excitability to a sub-threshold level within at least one spinal circuit by:

applying, via at least one of the at least one electrode, an electrical stimulation according to selected electrical stimulation parameters to excite neurons in dorsal roots of the patient to the sub-threshold level, wherein the electrical stimulation activates in real time dorsal root afferent fibers in the patient to stimulate a neural circuit regulating the one or more autonomic function, and wherein the at least one autonomic function is enabled or improved.

22. A system for enabling or improving, in a patient having a nervous system disorder, at least one autonomic function selected from a group consisting of cardiovascular function, body temperature, metabolic processes, bladder function, sexual function, vasomotor function, or cognitive function, the system comprising:

at least one electrode; and a stimulator including a processor communicatively coupled to the at least one electrode, the stimulator comprising at least one processor and a memory, the stimulator configured to:

select electrical stimulation parameters from a memory to induce, with the stimulator connected to the at least one electrode, spinal interneuronal excitability to a sub-threshold level within at least one spinal circuit, and cause the at least one electrode to apply electrical stimulation according to the selected stimulation parameters to excite neurons in dorsal roots of the patient to the sub-threshold level, wherein parameters of the electrical stimulation are configured to activate in real time dorsal root afferent fibers in the patient to stimulate a neural circuit regulating the at least one autonomic function, wherein the one or more autonomic function is enabled or improved.

\* \* \* \* \*